US012258592B2

(12) United States Patent
Bai et al.

(10) Patent No.: US 12,258,592 B2
(45) Date of Patent: Mar. 25, 2025

(54) PHYTASE MUTANT

(71) Applicant: Nanjing Bestzyme Bio-engineering Co., Ltd., Jiangsu (CN)

(72) Inventors: Aixi Bai, Jiangsu (CN); Feng Li, Jiangsu (CN)

(73) Assignee: NANJING BESTZYME BIO-ENGINEERING CO., LTD., Nanjing (CN)

( * ) Notice: Subject to any disclaimer, the term of this patent is extended or adjusted under 35 U.S.C. 154(b) by 571 days.

(21) Appl. No.: 17/059,696

(22) PCT Filed: May 30, 2019

(86) PCT No.: PCT/CN2019/089212
§ 371 (c)(1),
(2) Date: Nov. 30, 2020

(87) PCT Pub. No.: WO2019/228441
PCT Pub. Date: Dec. 5, 2019

(65) Prior Publication Data
US 2021/0207112 A1 Jul. 8, 2021

(30) Foreign Application Priority Data
May 30, 2018 (CN) .......................... 201810540167.5

(51) Int. Cl.
*C12N 9/16* (2006.01)
(52) U.S. Cl.
CPC ........ *C12N 9/16* (2013.01); *C12Y 301/03008* (2013.01)
(58) Field of Classification Search
CPC .............. C12N 9/16; C12Y 301/03008; C12Y 301/03026
See application file for complete search history.

(56) References Cited

U.S. PATENT DOCUMENTS

| | | |
|---|---|---|
| 5,436,156 A | 7/1995 | Van Gorcom et al. |
| 7,432,098 B2 | 10/2008 | Short et al. |
| 8,143,046 B2 | 3/2012 | Cervin et al. |
| 8,540,984 B2 | 9/2013 | Lei |
| 8,877,478 B2 | 11/2014 | Steer et al. |
| 9,765,313 B2 | 9/2017 | Yao et al. |
| 2010/0261259 A1 | 10/2010 | Matsui et al. |
| 2013/0017185 A1 | 1/2013 | De Maria et al. |
| 2017/0240872 A1 | 8/2017 | Guo et al. |

FOREIGN PATENT DOCUMENTS

| | | |
|---|---|---|
| CN | 107353327 A | 11/2017 |
| WO | 2011117396 A2 | 9/2011 |
| WO | 2011117397 A1 | 9/2011 |
| WO | 2011117406 A1 | 9/2011 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Garrett, James B., et al. "Enhancing the Thermal Tolerance and Gastric Performance of a Microbial Phytase for Use as a Phosphate-Mobilizing Monogastric-Feed Supplement," Applied and Environmental Microbiology, vol. 70, No. 5, May 2004, pp. 3041-3046.
Wu, Tzu-Hui et al., "Improving specific activity and thermostability of *Escherichia coli* phytase by structure-based rational design," Journal of Biotechnology, vol. 175, Apr. 10, 2014, pp. 1-6.
Nielsen, Anne Veller Friis et al. "Performance of Microbial Phytases for Gastric Inositol Phosphate Degradation," Journal of Agricultural and Food Chemistry, vol. 63, issue 3, Jan. 6, 2015, pp. 943-950.
lim, Daniel et al. "Crystal structures of *Escherichia coli* phytase and its complex with phytate," Nature Structural Biology, vol. 7, No. 2, Feb. 2000, pp. 108-113.
International Search Report (Form PCT/ISA/210) for International Patent Application No. PCT/CN2019/089212, issued from the International Searching Authority, date of mailing Sep. 4, 2019,, with English-language translation, 10 pages.
Written Opinion of the International Searching Authority (Form PCT/ISA/237) for International Patent Application No. PCT/CN2019/089212, issued from the International Searching Authority, dated Sep. 4, 2019, with English-language translation, 8 pages.

* cited by examiner

*Primary Examiner* — Delia M Ramirez
(74) *Attorney, Agent, or Firm* — Ice Miller LLP

(57) ABSTRACT

Disclosed is a thermostable phytase, in which at least one pair of introduced disulfide bonds is included in the amino acid sequence of wild-type *Escherichia coli* phytase or mutant *Escherichia coli* phytase, and after the introduction, the properties of the phytase can be improved, especially the heat stability, steam stability and granulation stability, which are superior to those of the existing wild-type or mutant phytase; compared to the engineered phytase in which disulfide bonds are introduced, the heat stability is also significantly improved.

15 Claims, 5 Drawing Sheets
Specification includes a Sequence Listing.

PHYTASE MUTANT

CROSS-REFERENCE TO RELATED APPLICATION

This application is a Section 371 of International Application No. PCT/CN2019/089212, filed May 30, 2019, which was published in the English language on Dec. 5, 2019, under International Publication No. WO 2019/228441 A1, and claims priority under 35 U.S.C. § 119 (b) to Chinese Patent Application No. 201810540167.5, filed May 30, 2018, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence_Listing" and a creation date of Nov. 24, 2020 and having a size of about 309 kb. The sequence listing submitted via EFS-Web is part of the specification and is herein incorporated by reference in its entirety.

BACKGROUND

Technical Field

The present invention belongs to the field of protein engineering, and relates to a phytase from gram-negative bacteria, more particularly to an *Escherichia coli* phytase. After modification through introduction of a pair or a plurality of pairs of disulfide bonds, its heat stability is improved.

Related Art

Phytase, i.e., myo-Inositol hexakisphosphate phosphohydrolase, belongs to orthophosphate monoacetate phosphohydrolase, catalyzes hydrolysis of phytic acid to produce lower myo-Inositol phosphate derivatives and inorganic phosphoric acid, and can hydrolyze the phytic acid into free myo-Inositol under some conditions. The phytic acid is most abundant in seeds of crops such as grains, beans and oil plants, which accounts for up to 1%-3% of the plants and 60%-80% of the total phosphorus content of the plants. However, the phosphorus in the phytic acid cannot be directly absorbed and utilized, and has to be firstly hydrolyzed into inorganic phosphates in the digestive tract. Studies have shown that monogastric animals (such as pigs, chickens, ducks and geese) have a very low utilization rate of the phosphorus in the phytic acid due to the lack of phytase. Moreover, due to strong electronegativity of the phytic acid, the phytic acid generally forms insoluble salts with divalent or trivalent cations, such as $Ca^{2+}$, $Zn^{2+}$ and $Fe^{2+}$, so as to hinder the absorption of minerals by the small intestines. The phytic acid may further form a complex with protein, amino acid, fatty acid and the like to influence their absorption and utilization. The phytic acid may further be combined with pepsin, chymotrypsin, trypsin and the like to reduce the activity of digestive enzymes. Therefore, by adding the phytase into monogastric animal feed, the utilization rate of phosphorus in the animal feed can be improved, the phosphorus content in animal excreta can be reduced, and the energy utilization rate of the protein and the feed can be improved.

The phytase is used as a feed additive to be added into a feed raw material in advance. Through processes such as high-temperature granulation (70-95° C., time: 30 s-120 s), the feed is produced for animal feeding. Therefore, in order to maximize the effect of the phytase, the phytase needs to resist a high temperature, i.e., the phytase should have good heat resistance. Commercially available phytases are mainly derived from *Aspergillus niger* (as described in U.S. Pat. No. 5,436,156), *Escherichia coli* (as described in U.S. Pat. No. 7,432,098), *Citrobacter braakii* (as described in US20100261259), *Buttiauxella* sp. (as described in U.S. Pat. No. 8,143,046) and the like. These phytases have different acid and heat resistance properties due to their different sources. Nielsen et al (J Agric Food Chem. 2015, 63 (3): 943-50) compared commercial phytase properties, and the result showed that an *Escherichia coli* phytase showed the best characteristics. The *Escherichia coli* phytase products described herein are mutants modified by protein engineering, and thus have better heat stability. U.S. Pat. Nos. 8,540,984, 9,765,313, 7,432,098 and 8,877,478 describe mutant enzymes with improved heat stability obtained by random mutation and site-directed mutation screening on the *Escherichia coli* phytase sequences. Patent Applications No. US20130017185 and US20170240872 mention that the heat stability of the enzyme can also be improved through introduction of specific disulfide bonds according to three-dimensional structures of the *Escherichia coli* phytase protein.

There is also a need in the art to provide more thermostable phytases.

SUMMARY

The inventor has found that through introduction of a pair or a plurality of pairs of disulfide bonds to specific positions in the amino acid sequence of an *Escherichia coli* wild-type phytase (such as one with more than 85% of sequence identity with an *Escherichia coli* wild-type phytase as shown by SEQ ID NO: 1) or an *Escherichia coli* phytase mutant (such as one with more than 75% of sequence identity with an *Escherichia coli* phytase mutant as shown by SEQ ID NO: 2), its stability can be improved, so that the objective of the present invention is achieved.

In some implementations, a pair or a plurality of pairs of disulfide bonds as shown in Table 1 are introduced to specific positions in the amino acid sequence of the *Escherichia coli* phytase mutant with more than 85% of sequence identity with the *Escherichia coli* wild-type phytase as shown by SEQ ID NO: 1. In some preferred implementations, a pair or a plurality of pairs of disulfide bonds as shown in Table 1 are introduced to specific positions in the amino acid sequence of the *Escherichia coli* phytase with more than 88%, 89%, 90%, 91%, 92%, 93%, 94%, 95%, 96%, 97%, 98% or 99% of sequence identity with the *Escherichia coli* wild-type phytase as shown by SEQ ID NO: 1.

In some other implementations, a pair or a plurality of pairs of disulfide bonds as shown in Table 1 are introduced to specific positions in the amino acid sequence of the *Escherichia coli* phytase mutant with more than 75% of sequence identity with the *Escherichia coli* phytase mutant as shown by SEQ ID NO: 2, SEQ ID NO: 3, SEQ ID NO: 79 or SEQ ID NO: 99. In some preferred implementations, a pair or a plurality of pairs of disulfide bonds as shown in Table 1 are introduced to specific positions in the amino acid sequence of the *Escherichia coli* phytase mutant with more than 80%, 82%, 84%, 86%, 88%, 90%, 91%, 92%, 93%, 94%, 95%, 96%, 97%, 98% or 99% of sequence identity with the *Escherichia coli* phytase mutant as shown by SEQ ID NO: 2, SEQ ID NO: 3, SEQ ID NO: 79 or SEQ ID NO: 99.

In some implementations, compared to the wild-type *Escherichia coli* phytase as shown by SEQ ID NO: 1, the mutant *Escherichia coli* phytase has a mutation on at least 1 position: 1, 25, 30, 36, 37, 38, 39, 46, 55, 60, 62, 65, 69, 70, 73, 74, 75, 76, 77, 79, 80, 85, 101, 108, 109, 111, 114, 116, 118, 120, 123, 126, 127, 133, 137, 138, 139, 141, 142, 146, 151, 157, 159, 161, 173, 176, 178, 180, 183, 184, 185, 186, 187, 188, 189, 204, 211, 233, 235, 245, 253, 255, 267, 276, 282, 283, 284, 286, 287, 288, 291, 295, 297, 311, 315, 317, 318, 327, 341, 354, 363, 367, 369, 370, 380, 382, 383, 385, 391, 402 and 408. In some preferred implementations, compared to the wild-type *Escherichia coil* phytase as shown by SEQ ID NO: 1, the mutant *Escherichia coli* phytase has a mutation on at least 1 position: 25, 46, 62, 70, 73, 74, 75, 76, 114, 137, 142, 146, 159, 173, 204, 255, 282, 283 and 284. In some more preferred implementations, compared to the wild-type *Escherichia coli* phytase as shown by SEQ ID NO: 1, the mutant *Escherichia coli* phytase has a mutation on at least 1 position: 25, 46, 62, 70, 73, 74, 75, 76, 114, 137, 142, 146, 159, 173, 204 and 255.

In some specific implementations, compared to the wild-type *Escherichia coli* phytase as shown by SEQ ID NO: 1, the mutant *Escherichia coli* phytase has a mutation on the following positions: 46, 62, 73, 75, 146, 159, 204 and 255. In some other specific implementations, compared to the wild-type *Escherichia coli* phytase as shown by SEQ ID NO: 1, the mutant *Escherichia coli* phytase has a mutation on the following positions: 25, 46, 62, 70, 73, 75, 114, 137, 142, 146, 159 and 255. In some specific implementations, compared to the wild-type *Escherichia coli* phytase as shown by SEQ ID NO: 1, the mutant *Escherichia coli* phytase has a mutation on the following positions: 46, 62, 70, 73, 74, 75, 76, 146, 159, 173, 255, 282, 283 and 284. In some other specific implementations, compared to the wild-type *Escherichia coli* phytase as shown by SEQ ID NO: 1, the mutant *Escherichia coli* phytase has a mutation on the following positions: 25, 46, 62, 70, 73, 74, 75, 114, 137, 142, 146, 159, 173, 255, 282, 283 and 284.

In some implementations, compared to the wild-type *Escherichia coli* phytase as shown by SEQ ID NO: 1, the mutant *Escherichia coli* phytase has at least one of the following mutations: Q1S, Q1V, Q1N, A25F, Q30K, A36K, W37F, P38Y, T39D, W46E, I55V, H60S, H60Q, Q62W, R65H, D69N, G70E, A73P, A73D, A73E, K74D, K74P, K74L, K74N, K75C, K75Q, G76T, C77A, Q79L, Q79R, Q79A, Q79G, Q79F, S80P, I85V, A101L, C108A, A109D, A109E, A109G, A109F, A109P, T111S, T111D, T111Q, T114H, T116A, T118R, T118S, S120R, P123E, N126Y, P127V, P127L, C133A, N137V, N137E, N137S, N137P, A138V, A138H, A138D, A138P, N139P, N139A, N139H, T141R, T141E, T141G, T141A, D142R, S146E, S146R, S151P, G157R, G157Q, G157N, G157L, G157A, R159Y, T161P, P173Y, P173S, N176P, N176K, C178A, K183R, Q184S, D185N, D185L, E186V, E186A, S187P, C188A, S189T, N204C, V211W, G233E, G235Y, T245E, Q253V, Y255D, R267A, H282N, P283G, P284T, K286F, Q287Y, A288E, A288R, A288V, V291I, T295I, V297T, G311S, E315G, E315S, N317L, W318Y, T327Y, L341Y, L341V, F354Y, K363A, K363L, S367F, N369P, T370P, A380P, A380R, A380T, C382A, E383S, R385S, R385V, R385T, C391A, E402R, E402T, E402D, E402P, E402N and C408A.

In some preferred implementations, compared to the wild-type *Escherichia coli* phytase as shown by SEQ ID NO: 1, the mutant *Escherichia coli* phytase has at least one of the following mutations: A25F, W46E, Q62W, G70E, A73P, K74N, K75C, K75Q, G76T, T114H, N137V, D142R, S146E, R159Y, P173S, N204C, Y255D, H282N, P283G and P284T. In some more preferred implementations, compared to the wild-type *Escherichia coli* phytase as shown by SEQ ID NO: 1, the mutant *Escherichia coli* phytase has at least one of the following mutations: A25F, W46E, Q62W, G70E, A73P, K74N, K75C, K75Q, G76T, T114H, N137V, D142R, S146E, R159Y, P173S, N204C and Y255D.

In some implementations, compared to the wild-type *Escherichia coli* phytase as shown by SEQ ID NO: 1, the mutant *Escherichia coli* phytase has at least one of the following mutations: W46E, Q62W, A73P, K75C, S146E, R159Y, N204C and Y255D. In some other implementations, compared to the wild-type *Escherichia coli* phytase as shown by SEQ ID NO: 1, the mutant *Escherichia coli* phytase has at least one of the following mutations: A25F, W46E, Q62W, G70E, A73P, K75C, T114H, N137V, D142R, S146E, R159Y and Y255D. In some implementations, compared to the wild-type *Escherichia coli* phytase as shown by SEQ ID NO: 1, the mutant *Escherichia coli* phytase has at least one of the following mutations: W46E, Q62W, G70E, A73P, K74N, K75Q, G76T, S146E, R159Y, P173S, Y255D, H282N, P283G and P284T. In some other implementations, compared to the wild-type *Escherichia coli* phytase as shown by SEQ ID NO: 1, the mutant *Escherichia coli* phytase has at least one of the following mutations: A25F, W46E, Q62W, G70E, A73P, K74N, K75Q, T114H, N137V, D142R, S146E, R159Y, P173S, Y255D, H282N, P283G and P284T.

In some specific implementations, compared to the wild-type *Escherichia coli* phytase as shown by SEQ ID NO: 1, the mutant *Escherichia coli* phytase has the following mutations: W46E, Q62W, A73P, K75C, S146E, R159Y, N204C and Y255D. In some other specific implementations, compared to the wild-type *Escherichia coli* phytase as shown by SEQ ID NO: 1, the mutant *Escherichia coli* phytase has the following mutations: A25F, W46E, Q62W, G70E, A73P, K75C, T114H, N137V, D142R, S146E, R159Y and Y255D. In some specific implementations, compared to the wild-type *Escherichia coli* phytase as shown by SEQ ID NO: 1, the mutant *Escherichia coli* phytase has the following mutations: W46E, Q62W, G70E, A73P, K74N, K75Q, G76T, S146E, R159Y, P173S, Y255D, H282N, P283G and P284T. In some other specific implementations, compared to the wild-type *Escherichia coli* phytase as shown by SEQ ID NO: 1, the mutant *Escherichia coli* phytase has the following mutations: A25F, W46E, Q62W, G70E, A73P, K74N, K75Q, T114H, N137V, D142R, S146E, R159Y, P173S, Y255D, H282N, P283G and P284T.

Specifically, the inventor has found that through introduction of a pair or a plurality of pairs of disulfide bond combinations as shown in Table 1 to the sequence of the *Escherichia coli* wild-type phytase as shown by SEQ ID NO: 1 or the sequence of the *Escherichia* mutant *coli* phytase as shown by SEQ ID NO: 2, SEQ ID NO: 3, SEQ ID NO: 79 or SEQ ID NO: 99, its heat stability can be improved.

TABLE 1

Name and position of introduced
disulfide bonds (amino acid position
number is subject to SEQ ID NO: 1)

| Disulfide bond name | Disulfide bond site |
|---|---|
| A | P34/Q174 |
| B | A56/G103 |
| C | Y57/L366 |
| D | Y61/L366 |
| E | Q82/S296 |
| F | L128/D203 |
| G | V140/E262 |
| H | T156/T191 |
| I | E165/T245 |
| J | T191/A210 |
| K | S196/V211 |
| L | A264/G312 |
| M | E315/A380 |
| N | G322/T356 |
| O | Q346/L393 |
| P | Q349/M390 |

In some implementations, a pair or a plurality of pairs of disulfide bonds is introduced to the wild-type or mutant *Escherichia coli* phytase. The disulfide bonds are selected from at least one item of (A), (B), (C), (D), (E), (J), (M) or (0), and the condition is that (C) and the (D) items are not met at the same time.

In some implementations, a pair of disulfide bonds is introduced to the wild-type or mutant *Escherichia coli* phytase. The disulfide bonds are selected from (A), (B), (C), (D), (E), (J), (M) or (O) items.

In some implementations, a plurality of pairs of disulfide bonds is introduced to the wild-type or mutant *Escherichia coli* phytase at the same time. Preferably, disulfide bonds (B)+(O), (C)+(O), (M)+(O), (B)+(D)+(O) or (D)+(M)+(O) are introduced to the wild-type or mutant *Escherichia coli* phytase at the same time. More preferably, disulfide bonds (B)+(O) or (C)+(O) are introduced to the wild-type or mutant *Escherichia coli* phytase at the same time.

For the purpose of the present invention, "introduction" does not limit any specific generation mode of the disulfide bonds. For example, "introduction" of the disulfide bonds may include replacement of an amino acid residue on a corresponding position of a phytase sequence to be introduced with the disulfide bonds with an amino acid residue capable of forming the disulfide bonds (including, for example, a cysteine residue Cys and a homocysteine residue Hcy); and insertion of an amino acid residue capable of forming the disulfide bonds on a corresponding position. Such replacement and/or insertion may be, for example, realized by a site-directed mutagenesis method well known in the art. "Introduction" also includes a condition that any one or two amino acid residues for forming the disulfide bonds are generated by natural mutation.

In order to produce a mutant modified in such a way, microbial bacteria such as *Escherichia coli* and fungi such as yeast (*Pichia, Schizosaccharomyces pombe*, etc.), filamentous fungi (such as *Aspergillus niger, Aspergillus oryzae* and *Trichoderma reesei*), and plants (such as corn, soybean and wheat) may be used as hosts for expression.

Expression and production of the mutant can be completed by general and known technologies. For example, APPLIED AND ENVIRONMENTAL MICROBIOLOGY, 2004, 3041-3046 describes expression of an *Escherichia coli* phytase and mutant in *Escherichia coli*. Journal of Biotechnology 175 (2014) 1-6 describes expression of the phytase and the mutant in *Pichia*. The patent application CN107353327 describes expression of the phytase and the mutant in *Aspergillus niger*.

In order to build the above mutation, a conventional site-directed mutation method can be used on the basis of the existing wild-type nucleotide sequence, and de novo synthesis can also be performed by a gene synthesis method. Introduction to a host cell is performed after promoter and terminator connection, and expression is performed under a proper culture condition. The method is a conventional method in the art.

"Wild-type phytase" refers to a phytase discovered in the nature and expressed by natural existing microbes, such as *Escherichia coli* cells.

"Mutant" or "mutant-type" refers to a polypeptide having phytase activity and including change of one or more (a plurality of) amino acid residues on one or more (a plurality of) positions, i.e., substitution, insertion and/or deletion. Substitution refers to replacement of an amino acid occupying a certain position by different amino acids. Deletion refers to removal of an amino acid occupying a certain position. Insertion refers to addition of 1-5 amino acids on and behind an adjoining position of the amino acid occupying a certain position. Mutation on the wild-type phytase also refers to amino acid substitution, insertion and/or deletion on at least one position in comparison to the wild-type phytase, and preferably refers to amino acid substitution on at least one position, such as "A25F", i.e., phenylalanine in a $25^{th}$ alanine substitution position of the wild-type phytase.

"(B)+(O)", "B+O" or "(B) item+(O) item" refers to introduction of two disulfide bonds to the sequence of the wild-type or mutant phytase, i.e., disulfide bonds are formed on two positions of the (B) item, and disulfide bonds are formed on two positions of the (O) item. Similarly, the descriptions with "+", such as the (C) item+(O) item, (M) item+(O) item, (B) item+(D) item+(O) item and (D) item+(M) item+(O) item in the invention have similar interpretations.

"Sequence identity" is defined into percentage of amino acid residues identical to amino acid residues in a specific peptide or polypeptide sequence of a candidate sequence without regarding any conservative substitution as a part of the sequence identity after sequence comparison and gap introduction as necessary so as to obtain the maximum percentage sequence identity. Sequence comparison may be performed in various modes in the technical scope of the art, so as to determine the percentage amino acid sequence identity, for example, by using public available computer software, such as BLAST, BLAST-2, ALIGN or Megalign (DNASTAR) software. Those skilled in the art can determine to measure proper parameters of comparison, including any algorithm required for obtaining maximum comparison on the compared sequence overall length.

Based on the findings, the present application provides the following technical solution.

1. A thermostable phytase, characterized in that at least one pair of introduced disulfide bonds is included in the amino acid sequence of wild-type *Escherichia coli* phytase or mutant *Escherichia coli* phytase, the amino acid sequence of the wild-type *Escherichia coli* phytase is as shown by SEQ ID NO: 1, and compared to the wild-type *Escherichia coli* phytase as shown by SEQ ID NO: 1, the mutant *Escherichia coli* phytase has a mutation on at least 1 position; and the introduced disulfide bonds are selected from:

(A) a disulfide bond formed between an amino acid residue on a position corresponding to a $34^{th}$ position of SEQ ID NO: 1 and an amino acid residue on a position corresponding to a 174$^{th}$ position of SEQ ID NO: 1;

(B) a disulfide bond formed between an amino acid residue on a position corresponding to a 56$^{th}$ position of SEQ ID NO: 1 and an amino acid residue on a position corresponding to a 103$^{rd}$ position of SEQ ID NO: 1;

(C) a disulfide bond formed between an amino acid residue on a position corresponding to a 57$^{th}$ position of SEQ ID NO: 1 and an amino acid residue on a position corresponding to a 366$^{th}$ position of SEQ ID NO: 1;

(D) a disulfide bond formed between an amino acid residue on a position corresponding to a 61$^{st}$ position of SEQ ID NO: 1 and an amino acid residue on a position corresponding to a 366$^{th}$ position of SEQ ID NO: 1;

(E) a disulfide bond formed between an amino acid residue on a position corresponding to an 82$^{nd}$ position of SEQ ID NO: 1 and an amino acid residue on a position corresponding to a 296$^{th}$ position of SEQ ID NO: 1;

(F) a disulfide bond formed between an amino acid residue on a position corresponding to a 128$^{th}$ position of SEQ ID NO: 1 and an amino acid residue on a position corresponding to a 203$^{rd}$ position of SEQ ID NO: 1;

(G) a disulfide bond formed between an amino acid residue on a position corresponding to a 140$^{th}$ position of SEQ ID NO: 1 and an amino acid residue on a position corresponding to a 262$^{nd}$ position of SEQ ID NO: 1;

(H) a disulfide bond formed between an amino acid residue on a position corresponding to a 156$^{th}$ position of SEQ ID NO: 1 and an amino acid residue on a position corresponding to a 191$^{st}$ position of SEQ ID NO: 1;

(I) a disulfide bond formed between an amino acid residue on a position corresponding to a 165$^{th}$ position of SEQ ID NO: 1 and an amino acid residue on a position corresponding to a 245$^{th}$ position of SEQ ID NO: 1;

(J) a disulfide bond formed between an amino acid residue on a position corresponding to a 191$^{st}$ position of SEQ ID NO: 1 and an amino acid residue on a position corresponding to a 210$^{th}$ position of SEQ ID NO: 1;

(K) a disulfide bond formed between an amino acid residue on a position corresponding to a 196$^{th}$ position of SEQ ID NO: 1 and an amino acid residue on a position corresponding to a 211$^{th}$ position of SEQ ID NO: 1;

(L) a disulfide bond formed between an amino acid residue on a position corresponding to a 264$^{th}$ position of SEQ ID NO: 1 and an amino acid residue on a position corresponding to a 312$^{th}$ position of SEQ ID NO: 1;

(M) a disulfide bond formed between an amino acid residue on a position corresponding to a 315$^{th}$ position of SEQ ID NO: 1 and an amino acid residue on a position corresponding to a 380$^{th}$ position of SEQ ID NO: 1;

(N) a disulfide bond formed between an amino acid residue on a position corresponding to a 322$^{nd}$ position of SEQ ID NO: 1 and an amino acid residue on a position corresponding to a 356$^{th}$ position of SEQ ID NO: 1;

(O) a disulfide bond formed between an amino acid residue on a position corresponding to a 346$^{th}$ position of SEQ ID NO: 1 and an amino acid residue on a position corresponding to a 393$^{rd}$ position of SEQ ID NO: 1; and (P) a disulfide bond formed between an amino acid residue on a position corresponding to a 349$^{th}$ position of SEQ ID NO: 1 and an amino acid residue on a position corresponding to a 390$^{th}$ position of SEQ ID NO: 1; and the conditions are as follows:
the (C) item and the (D) item are not met at the same time; and
the (H) item and the (J) item are not met at the same time.

2. The thermostable phytase according to implementation 1, wherein compared to the wild-type *Escherichia coli* phytase as shown by SEQ ID NO: 1, the mutant *Escherichia coli* phytase has a mutation on at least one of the following positions: 1, 25, 30, 36, 37, 38, 39, 46, 55, 60, 62, 65, 69, 70, 73, 74, 75, 76, 77, 79, 80, 85, 101, 108, 109, 111, 114, 116, 118, 120, 123, 126, 127, 133, 137, 138, 139, 141, 142, 146, 151, 157, 159, 161, 173, 176, 178, 180, 183, 184, 185, 186, 187, 188, 189, 204, 211, 233, 235, 245, 253, 255, 267, 276, 282, 283, 284, 286, 287, 288, 291, 295, 297, 311, 315, 317, 318, 327, 341, 354, 363, 367, 369, 370, 380, 382, 383, 385, 391, 402 and 408.

3. The thermostable phytase according to implementation 2, wherein compared to the wild-type *Escherichia coli* phytase as shown by SEQ ID NO: 1, the mutant *Escherichia coli* phytase has at least one of the following mutations: Q1S, Q1V, Q1N, A25F, Q30K, A36K, W37F, P38Y, T39D, W46E, I55V, H60S, H60Q, Q62W, R65H, D69N, G70E, A73P, A73D, A73E, K74D, K74P, K74L, K74N, K75C, K75Q, G76T, C77A, Q79L, Q79R, Q79A, Q79G, Q79F, S80P, I85V, A101L, C108A, A109D, A109E, A109G, A109F, A109P, T111S, T111D, T111Q, T114H, T116A, T118R, T118S, S120R, P123E, N126Y, P127V, P127L, C133A, N137V, N137E, N137S, N137P, A138V, A138H, A138D, A138P, N139P, N139A, N139H, T141R, T141E, T141G, T141A, D142R, S146E, S146R, S151P, G157R, G157Q, G157N, G157L, G157A, R159Y, T161P, P173Y, P173S, N176P, N176K, C178A, K183R, Q184S, D185N, D185L, E186V, E186A, S187P, C188A, S189T, N204C, V211W, G233E, G235Y, T245E, Q253V, Y255D, R267A, H282N, P283G, P284T, K286F, Q287Y, A288E, A288R, A288V, V291I, T295I, V297T, G311S, E315G, E315S, N317L, W318Y, T327Y, L341Y, L341V, F354Y, K363A, K363L, S367F, N369P, T370P, A380P, A380R, A380T, C382A, E383S, R385S, R385V, R385T, C391A, E402R, E402T, E402D, E402P, E402N and C408A.

4. The thermostable phytase according to implementation 3, wherein compared to the wild-type *Escherichia coli* phytase as shown by SEQ ID NO: 1, the mutant *Escherichia coli* phytase has any combination of mutations selected from the following group: W46E, Q62W, A73P, K75C, S146E, R159Y, N204C and Y255D;

A25F, W46E, Q62W, G70E, A73P, K75C, T114H, N137V, D142R, S146E, R159Y and Y255D;

W46E, Q62W, G70E, A73P, K74N, K75Q, G76T, S146E, R159Y, P173S, Y255D, H282N, P283G and P284T; and A25F, W46E, Q62W, G70E, A73P, K74N, K75Q, T114H, N137V, D142R, S146E, R159Y, P173S, Y255D, H282N, P283G and P284T.

5. The thermostable phytase according to implementation 4, wherein compared to the wild-type *Escherichia coli* phytase as shown by SEQ ID NO: 1, the mutant *Escherichia coli* phytase has any combination of mutations selected from the following group:

W46E, Q62W, A73P, K75C, S146E, R159Y, N204C and Y255D;

A25F, W46E, Q62W, G70E, A73P, K75C, T114H, N137V, D142R, S146E, R159Y and Y255D; and
W46E, Q62W, G70E, A73P, K74N, K75Q, G76T, S146E, R159Y, P173S, Y255D, H282N, P283G and P284T.

6. The thermostable phytase according to implementation 3, wherein the amino acid sequence of the mutant *Escherichia coli* phytase is SEQ ID NO: 2, SEQ ID NO: 3, SEQ ID NO: 79 or SEQ ID NO: 99.

7. The thermostable phytase according to any one of implementations 1-6, wherein the disulfide bonds are selected from at least one item of (A), (B), (C), (D), (E), (J), (M) or (0), and the condition is that the (C) item and the (D) item are not met at the same time.

8. The thermostable phytase according to implementation 7, wherein the amino acid sequence meets any two, three or more items in the follow group: the (A) item, the (B) item, the (C) item, the (D) item, the (E) item, the (J) item, the (M) item and the (O) item, and the condition is that the (C) item and the (D) item are not met at the same time.

9. The thermostable phytase according to implementation 7, wherein the amino acid sequence meets the (A) item, the (B) item, the (C) item, the (E) item, the (J) item or the (M) item.

10. The thermostable phytase according to implementation 7, wherein the amino acid sequence at least meets the (D) item or the (O) item.

11. The thermostable phytase according to implementation 10, wherein the amino acid sequence meets the (D) item.

12. The thermostable phytase according to implementation 10, wherein the amino acid sequence meets the (O) item.

13. The thermostable phytase according to implementation 7, wherein the amino acid sequence meets the (B) item and the (O) item; the (C) item and the (O) item; the (D) item and the (O) item; the (M) item and the (O) item; the (B) item, the (D) item and the (O) item; or the (D) item, the (M) item and the (O) item.

14. The thermostable phytase according to implementation 13, wherein the amino acid sequence meets the (B) item and the (O) item.

15. The thermostable phytase according to implementation 13, wherein the amino acid sequence meets the (C) item and the (O) item.

16. The thermostable phytase according to implementation 13, wherein the amino acid sequence meets the (M) item and the (O) item.

17. The thermostable phytase according to implementation 13, wherein the amino acid sequence meets the (B) item, the (D) item and the (O) item.

18. The thermostable phytase according to implementation 13, wherein the amino acid sequence meets the (D) item, the (M) item and the (O) item.

19. The thermostable phytase according to any one of implementations 1-18, further including at least one pair of introduced disulfide bonds, wherein the disulfide bonds are selected from:
(i) a disulfide bond formed between an amino acid residue on a position corresponding to a $31^{st}$ position of SEQ ID NO: 1 and an amino acid residue on a position corresponding to a $176^{th}$ position of SEQ ID NO: 1;
(ii) a disulfide bond formed between an amino acid residue on a position corresponding to a $31^{st}$ position of SEQ ID NO: 1 and an amino acid residue on a position corresponding to a $177^{th}$ position of SEQ ID NO: 1;
(iii) a disulfide bond formed between an amino acid residue on a position corresponding to a $52^{nd}$ position of SEQ ID NO: 1 and an amino acid residue on a position corresponding to a $99^{th}$ position of SEQ ID NO: 1;
(iv) a disulfide bond formed between an amino acid residue on a position corresponding to a $59^{th}$ position of SEQ ID NO: 1 and an amino acid residue on a position corresponding to a $100^{th}$ position of SEQ ID NO: 1;
(v) a disulfide bond formed between an amino acid residue on a position corresponding to a $91^{st}$ position of SEQ ID NO: 1 and an amino acid residue on a position corresponding to a $46^{th}$ position of SEQ ID NO: 1;
(vi) a disulfide bond formed between an amino acid residue on a position corresponding to a $141^{st}$ position of SEQ ID NO: 1 and an amino acid residue on a position corresponding to a $200^{th}$ position of SEQ ID NO: 1;
(vii) a disulfide bond formed between an amino acid residue on a position corresponding to a $162^{nd}$ position of SEQ ID NO: 1 and an amino acid residue on a position corresponding to a $248^{th}$ position of SEQ ID NO: 1; and
(viii) a disulfide bond formed between an amino acid residue on a position corresponding to a $205^{th}$ position of SEQ ID NO: 1 and an amino acid residue on a position corresponding to a $257^{th}$ position of SEQ ID NO: 1; and the condition is that the (i) item and the (ii) item are not met at the same time.

20. The thermostable phytase according to implementation 1, wherein the thermostable phytase has any amino acid sequence selected from the following group: SEQ ID NOs: 4-40, SEQ ID NOs: 80-88 and SEQ ID NOs: 100-108.

21. The thermostable phytase according to any one of the above implementations, wherein the thermostable phytase is obtained through heterologous expression in a *Pichia* or *Aspergillus niger* host.

22. The thermostable phytase according to any one of the above implementations, wherein the amino acid residue capable of forming the disulfide bonds is a cysteine residue or a homocysteine residue.

23. A polynucleotide, coding the thermostable phytase according to any one of implementations 1-22.

24. The polynucleotide according to implementation 23, wherein a coding sequence of the polynucleotide is subjected to codon optimization so as to realize expression in *Pichia* or *Aspergillus niger*.

25. The polynucleotide according to implementation 23, having a nucleotide sequence as shown by any one of SEQ ID NOs: 41-77, SEQ ID NOs: 90-98 and SEQ ID NOs: 110-118.

26. A host cell, including the polynucleotide according to any one of implementations 23-25.

27. The host cell according to implementation 26, wherein the host cell is a fungus cell, a bacterium cell or a plant cell.

28. The host cell according to implementation 27, being a yeast cell or a filamentous fungus cell.

29. The host cell according to implementation 28, being a *Pichia* cell or an *Aspergillus niger* cell.

30. A method for improving heat stability of a phytase, including: changing the amino acid sequence of a phytase of interest or the coded nucleotide sequence thereof so that a disulfide bond is capable of being formed between amino acid residues on two positions of at least one item selected from the following (A) to (P) in the amino acid sequence of the phytase:
(A) a position corresponding to a $34^{th}$ position of SEQ ID NO: 1, and a position corresponding to a $174^{th}$ position of SEQ ID NO: 1;

(B) a position corresponding to a 56$^{th}$ position of SEQ ID NO: 1, and a position corresponding to a 103$^{rd}$ position of SEQ ID NO: 1;

(C) a position corresponding to a 57$^{th}$ position of SEQ ID NO: 1, and a position corresponding to a 366$^{th}$ position of SEQ ID NO: 1;

(D) a position corresponding to a 61$^{st}$ position of SEQ ID NO: 1, and a position corresponding to a 366$^{th}$ position of SEQ ID NO: 1;

(E) a position corresponding to an 82$^{nd}$ position of SEQ ID NO: 1, and a position corresponding to a 296$^{th}$ position of SEQ ID NO: 1;

(F) a position corresponding to a 128$^{th}$ position of SEQ ID NO: 1, and a position corresponding to a 203$^{rd}$ position of SEQ ID NO: 1;

(G) a position corresponding to a 140$^{th}$ position of SEQ ID NO: 1, and a position corresponding to a 262$^{nd}$ position of SEQ ID NO: 1;

(H) a position corresponding to a 156$^{th}$ position of SEQ ID NO: 1, and a position corresponding to a 191$^{st}$ position of SEQ ID NO: 1;

(I) a position corresponding to a 165$^{th}$ position of SEQ ID NO: 1, and a position corresponding to a 245$^{th}$ position of SEQ ID NO: 1;

(J) a position corresponding to a 191$^{st}$ position of SEQ ID NO: 1, and a position corresponding to a 210$^{th}$ position of SEQ ID NO: 1;

(K) a position corresponding to a 196$^{th}$ position of SEQ ID NO: 1, and a position corresponding to a 211$^{th}$ position of SEQ ID NO: 1;

(L) a position corresponding to a 264$^{th}$ position of SEQ ID NO: 1, and a position corresponding to a 312$^{th}$ position of SEQ ID NO: 1;

(M) a position corresponding to a 315$^{th}$ position of SEQ ID NO: 1, and a position corresponding to a 380$^{th}$ position of SEQ ID NO: 1;

(N) a position corresponding to a 322$^{nd}$ position of SEQ ID NO: 1, and a position corresponding to a 356$^{th}$ position of SEQ ID NO: 1;

(O) a position corresponding to a 346$^{th}$ position of SEQ ID NO: 1, and a position corresponding to a 393$^{rd}$ position of SEQ ID NO: 1; and (P) a position corresponding to a 349$^{th}$ position of SEQ ID NO: 1, and a position corresponding to a 390$^{th}$ position of SEQ ID NO: 1; and the conditions are as follows:

the (C) item and the (D) item are not selected at the same time; and the (H) item and the (J) item are not selected at the same time.

31. The method according to implementation 30, wherein through the change, the disulfide bond is capable of being formed between the amino acid residues on two positions of at least one item selected from the (A) item, the (B) item, the (C) item, the (D) item, the (E) item, the (J) item, the (M) item or the (O) item in the amino acid sequence of the phytase of interest, and the condition is that the (C) item and the (D) item are not selected at the same time.

32. The method according to implementation 31, wherein through the change, the disulfide bond is capable of being formed between the amino acid residues on two positions of any two, three or more items selected from the following group of the amino acid sequence: the (A) item, the (B) item, the (C) item, the (D) item, the (E) item, the (J) item, the (M) item and the (O) item, and the condition is that the (C) item and the (D) item are not selected at the same time.

33. The method according to implementation 31, wherein through the change, the disulfide bond is capable of being formed between the amino acids on two positions of the (A) item, the (B) item, the (C) item, the (E) item, the (J) item or the (M) item in the amino acid sequence.

34. The method according to implementation 31, wherein through the change, the disulfide bond is capable of being formed between the amino acids on two positions of at least the (D) item or the (O) item in the amino acid sequence.

35. The method according to implementation 34, wherein through the change, the disulfide bond is capable of being formed between the amino acids on two positions of the (D) item in the amino acid sequence.

36. The method according to implementation 34, wherein through the change, the disulfide bond is capable of being formed between the amino acids on two positions of the (O) item in the amino acid sequence.

37. The method according to implementation 31, wherein through the change, the disulfide bond is capable of being formed between the amino acids on two positions respectively of the (B) item and the (O) item in the amino acid sequence.

38. The method according to implementation 31, wherein through the change, the disulfide bond is capable of being formed between the amino acids on two positions respectively of the (C) item and the (O) item in the amino acid sequence.

39. The method according to implementation 31, wherein through the change, the disulfide bond is capable of being formed between the amino acids on two positions respectively of the (M) item and the (O) item in the amino acid sequence.

40. The method according to implementation 31, wherein through the change, the disulfide bond is capable of being formed between the amino acids on two positions respectively of the (B) item, the (D) item and the (O) item in the amino acid sequence.

41. The method according to implementation 31, wherein through the change, the disulfide bond is capable of being formed between the amino acids on two positions respectively of the (D) item, the (M) item and the (O) item in the amino acid sequence.

42. The method according to any one of implementations 30-41, wherein the phytase of interest is from *Escherichia coli*, and has an amino acid sequence with at least 75% of sequence identity with an amino acid sequence as shown by SEQ ID NO: 1, SEQ ID NO: 2, SEQ ID NO: 3, SEQ ID NO: 79 or SEQ ID NO: 99.

43. The method according to implementation 42, wherein the phytase of interest is wild-type *Escherichia coli* phytase, and preferably has an amino acid sequence as shown by SEQ ID NO: 1.

44. The method according to implementation 42, wherein the phytase of interest is mutant *Escherichia coli* phytase, and preferably has an amino acid sequence as shown by SEQ ID NO: 2, SEQ ID NO: 3, SEQ ID NO: 79 or SEQ ID NO: 99.

45. The method according to any one of implementations 30-44, wherein the changed phytase has an amino acid sequence selected from the following group, or its coded nucleic acid has a nucleotide sequence coding the amino acid sequence selected from the following group: SEQ ID NOs: 4-40, SEQ ID NOs: 80-88 and SEQ ID NOs: 100-108.

46. The method according to any one of implementations 30-45, wherein the method further includes generating a phytase having the modified amino acid sequence, and putting the phytase into an environment allowing formation of disulfide bonds.

47. The method according to implementation 46, wherein the generating a phytase having the modified amino acid sequence includes expressing polynucleotide coding the phytase in a host cell.

48. The method according to implementation 47, wherein the host cell is a fungus cell, is preferably a yeast cell or a filamentous fungus cell, and is more preferably a *Pichia* cell or an *Aspergillus niger* cell.

The present invention has the following beneficial effects:
As described in the present invention, a pair or a plurality of pairs of disulfide bonds is introduced to a phytase and a mutant. Particularly, a plurality of pairs of disulfide bonds is introduced at the same time. At least one pair of disulfide bonds is introduced to the wild-type or mutant phytase in the present invention, which has its residual activity improved by about 1-8 times compared to that of the wild-type phytase. Therefore, the technical solution of the present invention can improve enzyme activity of the phytase. The phytase is significantly superior to the existing wild-type or mutant phytase especially in aspects of heat stability, steam stability and granulation stability. Its heat stability is also significantly improved compared to that of the existing engineered phytase in which disulfide bonds are introduced.

DETAILED DESCRIPTION

Embodiment 1 Disulfide bond mutant building, and wild-type and mutant expression in *Pichia*

A 3D structure of an *Escherichia coli* phytase has been published (referring to Lim D et al, Nat Struct Biol. 2000, 7(2):108-13), and with reference to a 3D structure document PDB ID 1DKO, disulfide bonds as described in the table below were designed and introduced.

| Disulfide bond name | Disulfide bond site |
| --- | --- |
| A | P34C/Q174C |
| B | A56C/G103C |
| C | Y57C/L366C |
| D | Y61C/L366C |
| E | Q82C/S296C |
| F | L128C/D203C |
| G | V140C/E262C |
| H | T156C/T191C |
| I | E165C/T245C |
| J | T191C/A210C |
| K | S196C/V211C |
| L | A264C/G312C |
| M | E315C/A380C |
| N | G322C/T356C |
| O | Q346C/L393C |
| P | Q349C/M390C |
| Q | T33C/L170C |
| R | I55C/A99C |
| S | A268C/N309C |
| T | I85C/G97C |
| U | P123C/T130C |
| V | A226C/M360C |
| W | W243C/P324C |
| X | W347C/M390C |
| Y | I348C/F396C |

Figure 1:
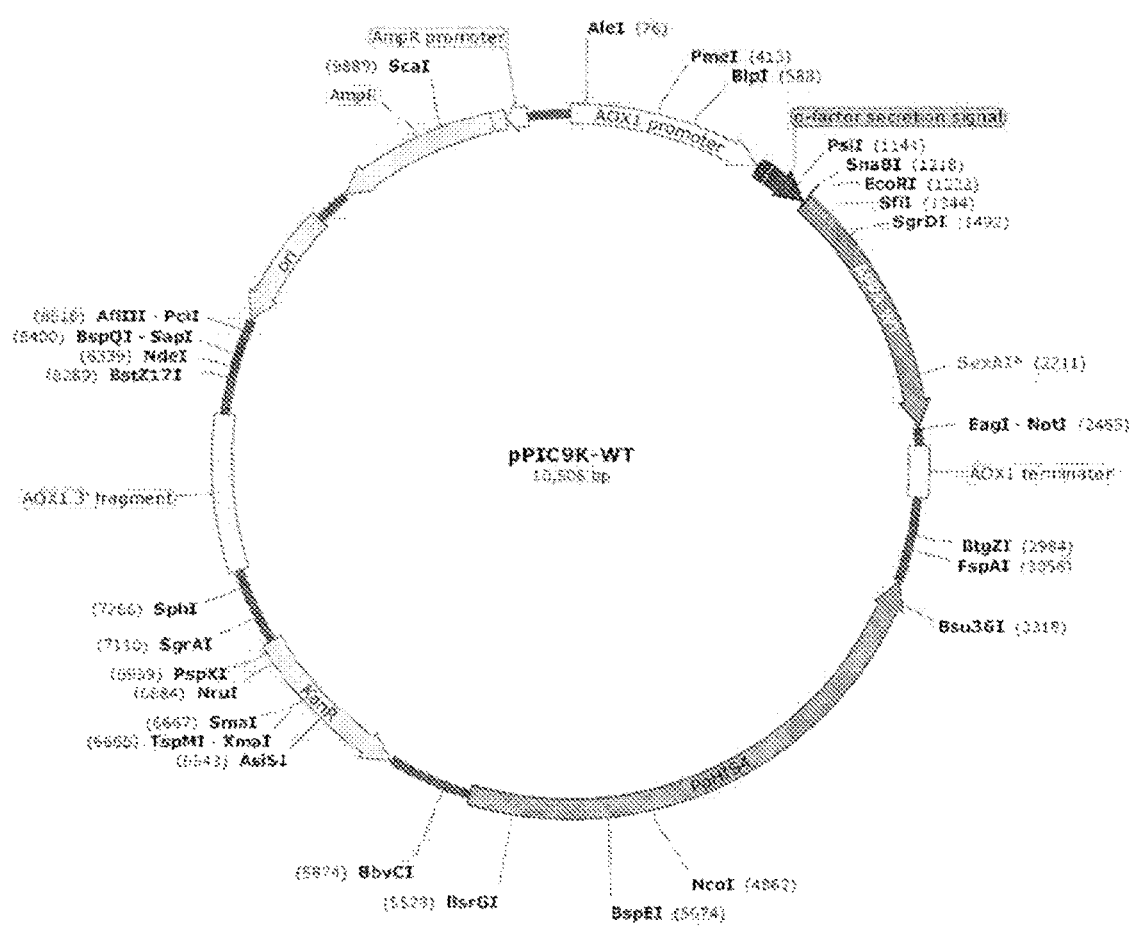
FIG. 1 is a pPIC9K-WT plasmid profile.

The amino acid sequence of a wild-type phytase was as shown by SEQ ID NO: 1. A nucleotide sequence thereof expressed in the *Pichia* was as shown by SEQ ID NO: 78. An expression vector was pPIC9K. A *Saccharomyces cerevisiae* Alpha factor was used as a signal peptide. An expression plasmid pPIC9K-WT of the wild-type phytase was as shown in FIG. 1.

In order to build the mutant in the above table, primers were respectively designed for Polymerase Chain Reaction (PCR). The primers were as shown by the table below.

```
Disulfide
bond       Disulfide bond
name       site              Mutation primer A          P34C/Q174C        A-F1 GATGTCACCtgtGACGCTTGGCCAACCTGGA-
                             F2 AACTTCCCAtgtTCAAACTTGTGCTTGAAG
                             A-R1 CCAAGCGTCacaGGTGACATCTTGCATAAG
                             A-R2 CAAGTTTGAacaTGGGAAGTTAAGAACTCT B          A56C/G103O        B-F1 GAGCTCATTtgtTACTTGGGTCACTACCAA
                             B-F2 TTCGCCGCCtgtCTTGCTCCTGACTGTGCC
                             B-R1 ACCCAAGTAacaAATGAGCTCACCACCTCT
                             B-R2 AGGAGCAAGacaGGCGGCGAAGGCTTCACC C          T57C/L366C        C-F1 CTCATTGCTtgtTTGGGTCACTACCAAAGAC-
                             F2 AAGACTCCAtgtTCTTTGAACACGCCTCCA
                             C-R1 GTGACCCAAacaAGCAATGAGCTCACCACC
                             C-R2 GTTCAAAGAacaTGGAGTCTTGTCTCTCAT D          T61C/L366C        D-F1 TTGGGTCACtgtCAAAGACAGCGTCTTGTT
                             D-F2 AAGACTCCAtgtTCTTTGAACACGCCTCCA
                             D-R1 CTGTCTttgacaGTGACCCAACTAAGCAAT
                             D-R2 GTTCAAAGAacaTGGAGTCTTGTCTCTCAT
```

-continued

| Disulfide bond name | Disulfide bond site | Mutation primer |
|---|---|---|
| E | Q82C/S296C | E-F1 CAATCTGGTtgtGTAGCTATTATTGCTGAC |
| | | E-F2 TTGCCCACTtgtGTCTTGTTCATTGCCGGT |
| | | E-R1 AATAGCTACacaACCAGATTGTGGACAACC |
| | | E-R2 GAACAAGACacaAGTGGGCAAGGTAACACC |
| F | L128C/D203C | F-F1 TTCAACCCTtgtAAGACTGGTGTTTGCCA |
| | | F-F2 GTCTCCGCCtgtAACGTCTCTTTGACCGGTF-R1 ACCAGTCTTacaAGGGTTGAACAATGGATC |
| | | F-R2 AGAGACGTTacaGGCGGAGACCTTCAACTC |
| G | V140C/E262C | G-F1 aacGCTAACtgtACTGACGCTATCTTGTCC |
| | | G-F2 AGAACTCCAtgtGTTGCTAGATCCAGAGCC |
| | | G-R1 AGCGTCAGTacaGTTAGCGTTGTCCAATTG |
| | | G-R2 TCTAGCAAcacATGGAGTTCTCTGCAGCAA |
| H | T156C/T191C | H-F1 GCTGACTTCtgtGGTCACAGACAGACTGCC |
| | | H-F2 TGTTCCTTGtgtCAAGCATTACCATCTGAGH-R1 tctGTGACCacaGAAGTCAGCAATGGATCC |
| | | H-R2 TAATGCTTGacaCAAGGAACAGGATTCGTC |
| I | E165C/T245C | I-F1 GCCTTCAGAtgtTTGGAAAGAGTTCTTAAC |
| | | I-F2 CAATGGAACtgtTTGTTGTCCTTGCACAAC |
| | | I-R1 TCTTTCCAAacaTCTGAAGGCAGTCTGTCT |
| | | I-R2 GGACAACAAacaGTTCCATTGGTGAGAGTC |
| | T191C/A210C | J-F1 TGTTCCTTGtgtCAAGCATTACCATCTGAG |
| | | J-F2 TTGACCGGTtgtGTCAGCTTGGCTTCCATG |
| | | J-RI TAATGCTTGacaCAAGGAACAGGATTCGTC |
| | | J-R2 CAAGCTGACacaACCGGTCAAAGAGACGT |
| K | S196C/V211C | K-F1 GCATTACCAtgtGAGTTGAAGGTCTCCGCC |
| | | K-F2 ACCGGTGCTtgtAGCTTGGCTTCCATGTTG |
| | | K-R1 CTTCAACTCacaTGGTAATGCTTGAGTCAA |
| | | K-R2 AGCCAAGCTacaAGCACCGGTCAAAGAGAC |
| L | A264C/G312C | L-F1 CCAGAGgTTtgtAGATCCAGAGCCACCCCA |
| | | L-F2 AATCTCGGCtgtGCTTTGGAGTTGAACTGG |
| | | L-R1 TCTGGATCTacaAAcCTCTGGAGTTCTCTG |
| | | L-R2 CTCCAAAGCacaGCCGAGATTTGCCAAGTT |
| M | E315C/A380C | M-F1 GGTGCTTTGtgtTTGAACTGGACTCTTCCT |
| | | M-F2 TTGACCTTGtgtGGATGTGAAGAGAGAAAT |
| | | M-R1 CCAGTTCAAacaCAAAGCACCGCCGAGATT |
| | | M-R2 TTCACATCCacaCAAGGTCAATTTGACTTC |
| N | G322C/T356C | N-F1 ACTCTTCCTtgtCAACCTGATAACACTCCA |
| | | N-F2 GTCTTCCAAtgtTTGCAGCAGATGAGAGAC |
| | | N-R1 ATCAGGTTGacaAGGAAGAGTCCAGTTCAA |
| | | N-R2 CTGCTGCAAacaTTGGAAGACCAACGAAAC |
| O | Q346C/L393C | O-F1 GATAACTCTtgtTGGATTCAGGTTTCGTTG |
| | | O-F2 ATGTGTTCCtgtGCTGGTTTCACTCAAATC |
| | | O-R1 CTGAATCCAacaAGAGTTATCAGATAGTCT |
| | | O-R2 GAAACCAGCacaGGAACACATACCCTGAGC |
| P | Q349C/M390C | P-F1 CAATGGATTtgtGTTTCGTTGGTCTTCCAA |
| | | P-F2 GCTCAGGGTtgtTGTTCCTTGGCTGGTTTC |
| | | P-R1 CAACGAAACacaAATCCATTGAGAGTTATC |
| | | P-R2 CAAGGAACAacaACCCTGAGCATTTCTCTC |
| Q | T33C/L170C | Q-F1 CAAGATGTCtgtCCAGACGCTTGGCCAACC |
| | | Q-F2 GAAAGAGTTtgtAACTTCCCACAAtcaAAC |
| | | Q-R1 AGCGTCTGGacaGACATCTTGCATAAGTTG |
| | | Q-R2 TGGGAAGTTacaAACTCTTTCCAACTCTCT |
| R | I55C/A99C | R-F1 GGTGAGCTCtgtGCTTACTTGGGTCACTAC |
| | | R-F2 ACAGGTGAAtgtTTCGCCGCCGGTCTTGCT |
| | | R-R1 CAAGTAAGCacaGAGCTCACCACCTCTAGG |
| | | R-R2 GGCGGCGAAacaTTCACCTGTCTTACGGGT |

-continued

| Disulfide bond name | Disulfide bond site | Mutation primer |
|---|---|---|
| S | A268C/N309C | S-F1 AGATCCAGAtgtACCCCATTGTTGGACTTG<br>S-F2 AACTTGGCAtgtCTCGGCGGTGCTTTGGAG<br>S-R1 CAATGGGGTacaTCTGGATCTAGCAAcCTC<br>S-R2 ACCGCCGAGacaTGCCAAGTTAGTATCGTG |
| T | I85C/G97C | T-F1 CAAGTAGCTtgtATTGCTGACGTCGACGAA<br>T-F2 CGTAAGACAtgtGAAGCCTTCGCCGCCGGT<br>T-R1 GTCAGCAATacaAGCTACTTGACCAGATTG<br>T-R2 GAAGGCTTCACaTGTCTTACGGGTTCTTTC |
| U | P123C/T130C | U-F1 TCTCCAGATtgtTTGTTCAACCCTTTGAAG<br>U-F2 CCTTTGAAGtgtGGTGTTTGCCAATTGGAC<br>U-R1 GTTGAACAAacaATCTGGAGAAGAAGTGTC<br>U-R2 GCAAACACCacaCTTCAAAGGGTTGAACAA |
| V | A226C/M360C | V-F1 CTGCAACAAtgtCAAGGTATGCCTGAGCCA<br>V-F2 TTGCAGCAGtgtAGAGACAAGACTCCACTG<br>V-R1 CATACCTTGAcaTTGTTGCAGAAGAAAGAT<br>V-R2 CTTGTCTCTacaCTGCTGCAAAGTTTGGAA |
| W | W243C/P324C | W-F1 TCTCACCAATGtAACACCTTGTTGTCCTTG<br>W-F2 CCTGGTCAAtgtGATAACACTCCACCAGGT<br>W-R1 CAAGGTGTTacaTTGGTGAGAGTCGGTGAT<br>W-R2 AGTGTTATCacaTTGACCAGGAAGAGTCCA |
| X | W347C/M390C | X-F1 AACTCTCAAtgtATTCAGGTTTCGTTGGTC<br>X-F2 GCTCAGGGTigtTGTTCCTTGGCTGGTTTC<br>X-R1 AACCTGAATaCATTGAGAGTTATCAGATAG<br>X-R2 CAAGGAACAacaACCCTGAGCATTTCTCTC |
| Y | I348C/F396C | Y-F1 TCTCAATGGtgtCAGGTTTCGTTGGTCTTC<br>Y-F2 TTGGCTGGTtgtACTCAAATCGTTAACGAA<br>Y-R1 CGAAACCTGacaCCATTGAGAGTTATCAGA<br>Y-R2 GATTTGAGTacaACCAGCCAAGGAACACAT |

In order to introduce 25 pairs of disulfide bonds of A-Y, plasmid pPIC9K-WT was used as a template. F1/R2 and F2/R1 were used as introduction pairs. Two PCR amplification reactions were respectively performed. The amplification reaction was completed by a Phusion® High-Fidelity DNA polymerase (New England Biolabs, article number: M0530L). Setting was performed with reference to its manual. After the amplification was completed, a Dpnl endonuclease (New England Biolabs) was added for digesting the template. Then, Gibson Assembly® Master Mix Kit (New England Biolabs, article number: E2611) was used for fragment recombination. Through sequencing, successful building of the mutant plasmid was confirmed. The mutant plasmid was respectively named as pPIC9K-A to pPIC9K-Y according to the disulfide bond name in the above table.

In order to express the phytase and the mutant, the *Pichia* GS115 and the plasmid were operated with reference to *Pichia* expression kit (Invitrogen) manual. Specifically, after a *Pichia* GS115 strain was subjected to plate culture at 30° C. for 48 h by a YPD culture medium (1% of yeast extracts, 2% of protein, 2% of glucose and 1.5% of agar), monoclone was selected into a 4 mL YPD liquid culture medium (1% of yeast extracts, 2% of protein, and 2% of glucose), cultured at 30° C. and 200 rpm for 12 h, transferred to an Erlenmeyer flask with 30 mL YPD liquid culture medium, and cultured at 30° C. and 220 rpm for 4-5 h. After an OD600 value was detected to be in a range of 1.1-1.3, culture solution was centrifuged at 4° C. and 9,000 rpm for 2 min. 4 mL of thalli were respectively collected into sterile EP tubes. Supernatants were slightly abandoned. After residual supernatants were thoroughly absorbed by sterile filter paper, 1 mL of precooled sterile water was used for resuspending the thalli. Centrifugation at 4° C. and 9,000 rpm was performed for 2 min. Supernatants were abandoned. The above steps were repeated. The thalli were resuspended by 1 mL of precooled sorbitol (1 mol/L). Centrifugation at 4° C. and 9,000 rpm was performed for 2 min. Supernatants were abandoned. The thalli were resuspended by 100-150 µl of precooled sorbitol (1 mol/L). Hereto, preparation of competent cells was completed. The expression plasmid pPIC9K-WT and the other 25 disulfide bond mutants were linearized by BglII. Linearized fragments were purified and recovered and were then converted into the *Pichia* GS115 competent cells by an electroporation method. A mixture was uniformly coated onto an MD plate to be subjected to 30° C. reverse culture for 2-3 d. All bacterial colonies on the plate were washed down by sterile water and were then coated onto a YPD (0.5 mg/mL-8 mg/mL) plate containing different concentrations of geneticin for screening multicopy converters. *Pichia* recombination strains were obtained through screening on the MD plate, and were named as APPA-WT and APPA-A, APPA-B, APPA-C, APPA-D, APPA-E, APPA-F, APPA-G, APPA-H, APPA-I, APPA-J, APPA-K, APPA-L, APPA-M, APPA-N, APPA-O, APPA-P, APPA-Q, APPA-R, APPA-S, APPA-T, APPA-U, APPA-V, APPA-W, and APPA-X and APPA-Y The above clones obtained through screening were respectively transferred into a BMGY culture medium to be cultured for 24 h in an oscillation table concentrator at 30°

C. and 250 rpm, and were then transferred into a BMMY culture medium. Conditions of 30° C. and 250 rpm were maintained. 0.5% of methanol was added every day. After 120 h of induction expression, 9000-12000 rpm centrifugation was performed for 10 min so as to remove thalli. A fermentation supernatant containing a phytase APPA-WT and its 25 mutants was obtained. An SD S-PAGE result showed that three mutants of APPA-S, APPA-X and APPA-Y were not expressed, and the other 22 mutants were expressed.

Embodiment 2 Heat Stability Determination

Figure 2:
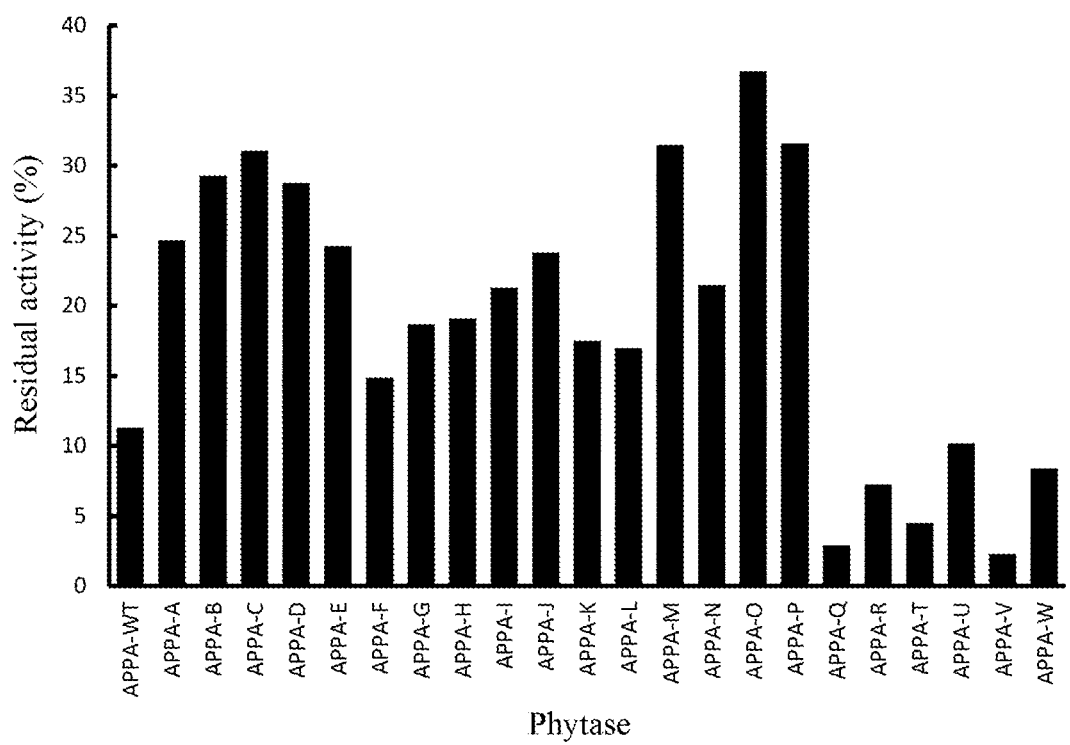
FIG. 2 is a diagram showing a heat stability test result of a wild-type and disulfide bond mutant.

Phytase activity determination conforms to GB/T 18634-2009. 23 samples in Embodiment 1 were diluted to 100 U/mL. 9 mL of water was taken in a 25 mL colorimetric tube to be respectively preheated in an 80° C. constant-temperature water bath. 1 mL of each enzyme sample was sucked by a pipette and were added fast into each corresponding test tube. Fast mixing and blending was performed by a mixing and blending device, followed by standing for 3 min. The temperature was fast cooled to a room temperature. Dilution was performed by water. Residual activity of each sample was determined. Therefore, the enzyme activity residue rates (the enzyme activity before heat treatment was set to be 100%) at different treatment temperatures were calculated. The heat stability data was as shown in FIG. 2. Some mutants showed good heat stability. APPA-B, APPA-C, APPA-D, APPA-M, APPA-O and APPA-P had the best performance, with the residual activity improved by about 20-25%, or about 2-3 times, compared with that of APPA. The above results showed that the introduction of the disulfide bonds had significant influence on the mutants. Some mutations even caused normal expression incapability, such as APPA-S, APPA-X and APPA-Y. Additionally, the introduction of some specified disulfide bonds may cause stability reduction. For example, the two mutants, such as APPA-Q and APPA-V caused heat stability significantly lower than that of the wild type. There were also some introduced disulfide bonds beneficial to the enzyme structure stability, such as APPA-A to APPA-P which can improve the heat resistance capability of the wild type.

Figure 3:
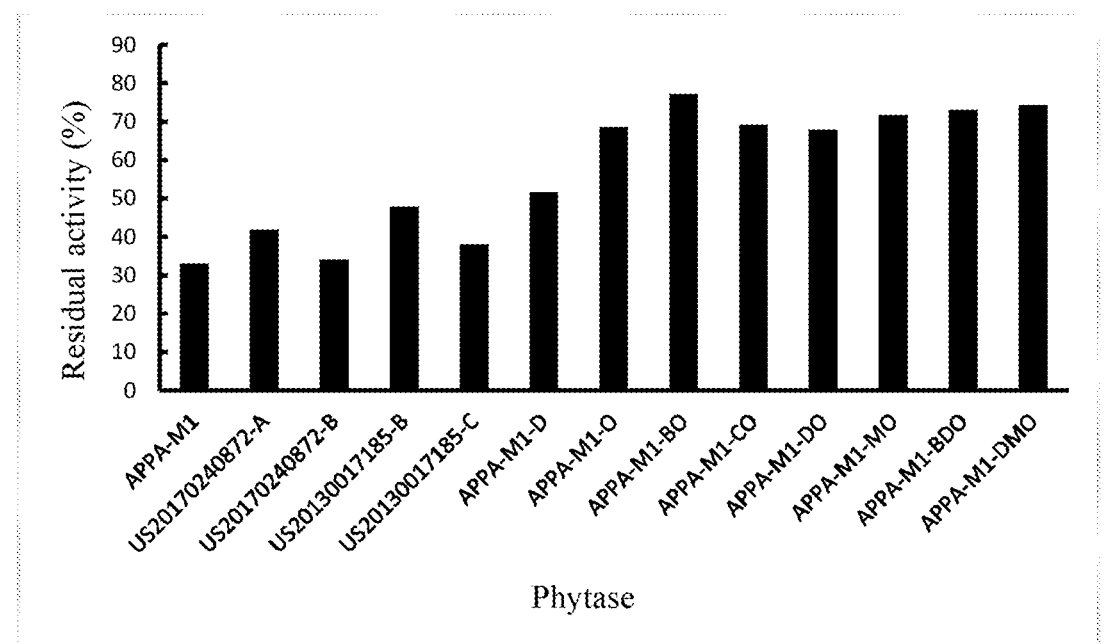
FIG. 3 is a diagram of a heat stability test result of an APPA-M1 and mutant.

Embodiment 3 Introduction of Disulfide Bonds on Basis of Mutant and Determination of its Stability Nov9X is a mutant with good heat resistance obtained through mutation screening by the wild-type phytase (as described in U.S. Pat. No. 7,432,098). 8 mutations were introduced on the basis of the wild type. A specific sequence was as shown by SEQ ID NO: 2. Other mutations were continuously introduced on the basis of the Nov9X sequence. The sequence became one as shown in SEQ ID NO: 3, and the mutant was named as APPA-M1. Its heat stability can be further improved. In order to test whether the disulfide bond mutant described in Embodiment 1 can achieve a function on the phytase mutant or not, the stability was further improved. The disulfide bonds D and O and disulfide bond combinations B+O, C+O, D+O, M+O, B+D+O and D+M+O were introduced on the basis of APPA-M1 according to a method in Embodiment 1. Each mutant was respectively named as APPA-M1-D, APPA-M1-O, APPA-M1-BO, APPA-M1-CO, APPA-M1-DO, APPA-M1-MO, APPA-M1-BDO and APPA-M1-DMO. Meanwhile, according to description in US20170240872 and US20130017185, two best mutant disulfide bonds in each embodiment were introduced on the basis of APPA-M1, and the mutants were respectively named as US20170240872-A, US20170240872-B, US20130017185-B and US20130017185-C. Each mutant was expressed in *Pichia*. Then, heat stability was determined according to a method in Embodiment 2. A different parameter was incubation for 3 min at 85° C. The results were as shown in FIG. 3. The disulfide bonds D and O both further improved the heat stability of the mutant, and the improvement brought by the disulfide bond O on the stability of the APPA-M1 mutant was greater than the improvement brought on the wild-type APPA-WT. The disulfide bond O improved the stability of the APPA-M1 mutant by up to 35.5%. Disulfide bond combined introduced mutants APPA-M1-CO and APPA-M1-DO showed stability similar to APPA-M1-O. Other combination mutants, such as APPA-M1-BO, APPA-M1-MO, APPA-M1-BDO and APPA-M1-DMO had higher stability. The residual activity of APPA-M1-BO with the best stability can reach 77.2%, and was improved by about 1-1.5 times compared with that of APPA-M1, the significant heat resistance characteristic was realized, and APPA-M1-BO was predicted to have good performance in feed granulation. The above results showed that the proper combination can create more stable mutants. The stability of US20170240872-A and US20170240872-B determined by this method was improved by 1.1-8.7% compared with that of APPA-M1. The stability of US20130017185-B and US20130017185-C was improved by 5.0-14.8%. It can be seen that the introduction of the disulfide bonds provided by the inventor showed more effective results.

Figure 4:
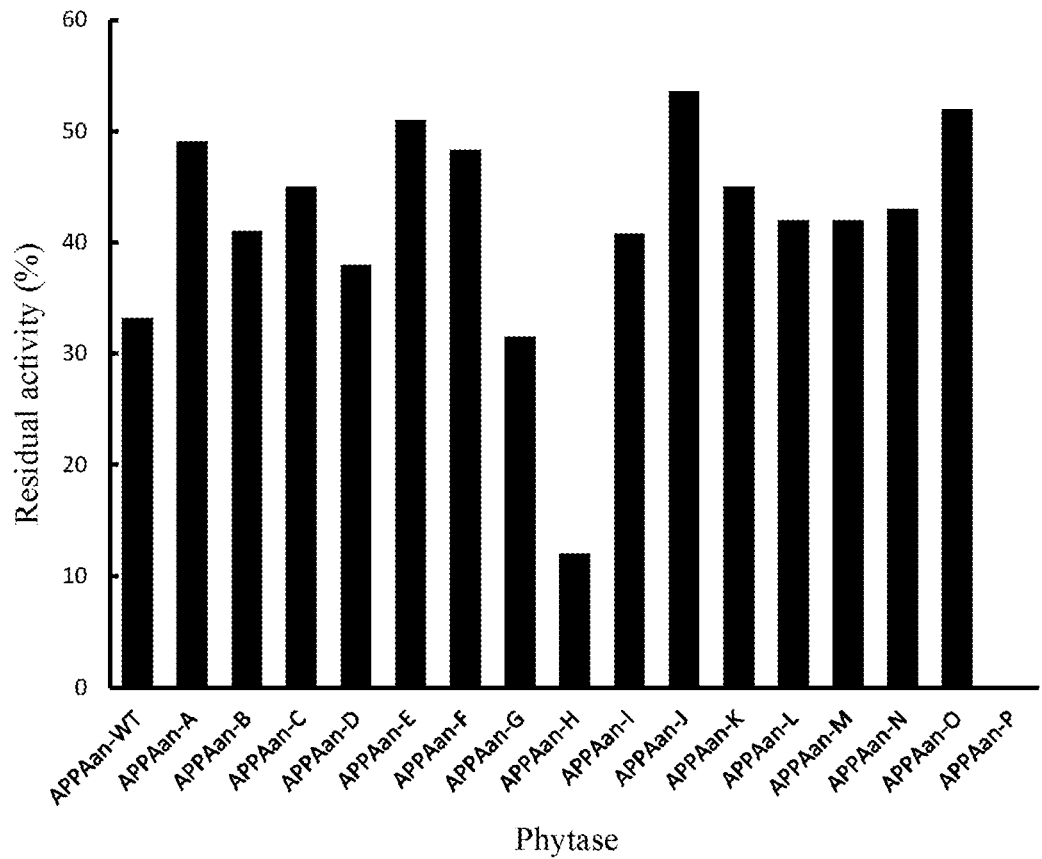
FIG. 4 is a diagram of a heat stability test result of an APPAan-WT and mutant.

Embodiment 4 Expression of *Escherichia coli* Wild-Type Phytase in *Aspergillus niger* and Disulfide Bond Introduced Mutant Phytase According to description of patent application CN107353327, the *Escherichia coli* phytase wild type (SEQ ID NO: 1) and mutants (A to P) were expressed. The wild-type phytase was named as APPAan-WT. Each mutant was named according to APPAan-A to APPAan-P. After shake flask supernatant was obtained, heat stability determination was performed according to description in Embodiment 2. A different parameter was incubation for 3 min at 85° C. The experiment results were as shown in FIG. 4. It is found that the wild-type phytase expressed in *Aspergillus niger* showed more significant stability than that expressed in *Pichia* probably because they had different glycosylation states. Through experiments, it is also found that the mutant APPAan-P cannot be expressed, APPAan-G expressed stability similar to WT, and the stability of APPAan-H was significantly reduced. The other 13 mutants all expressed significant stability performance improvement, and all expressed improvement of 5% to 20.5%, which was different from that of mutants expressed in *Pichia*. The above results showed that 16 mutants expressed in at least one host cell, and showed more excellent stability than the wild type. Through the proper introduction of the disulfide bond combination, mutants with higher stability can be obtained.

Figure 5:
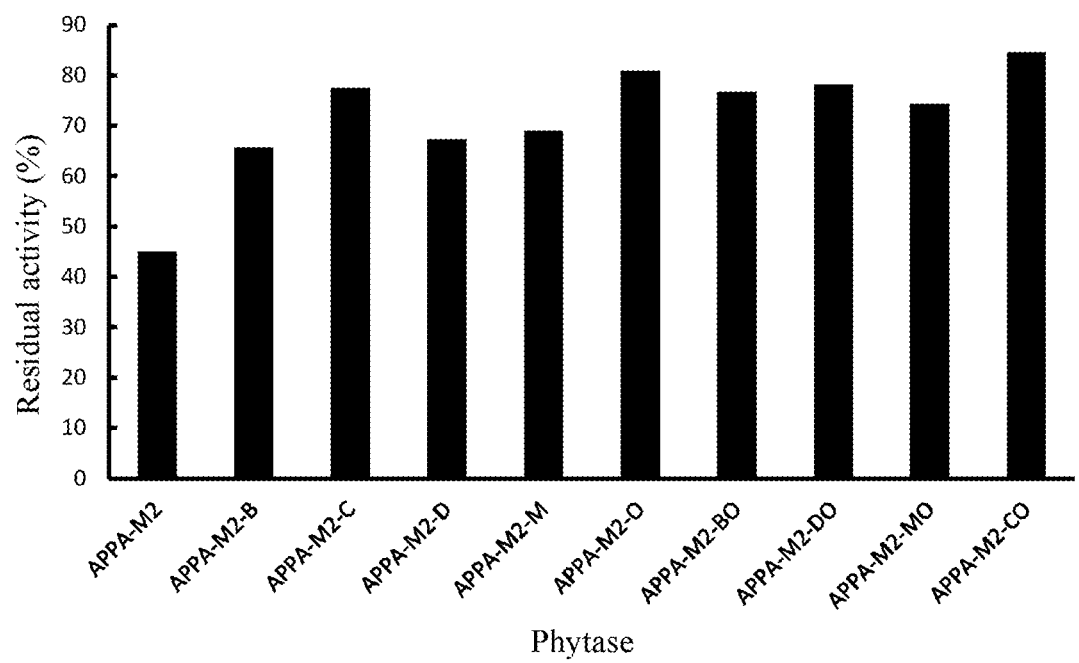
FIG. 5 is a diagram of a heat stability test result of an APPA-M2 and mutant.

Embodiment 5 Stability Test Results after Introduction of Disulfide Bonds to Phytase Mutants Nov9X is a mutant with good heat resistance obtained through mutation screening by the wild-type phytase (as described in U.S. Pat. No. 7,432,098). 8 mutations were introduced on the basis of the wild type. A specific sequence was as shown by SEQ ID NO: 2. On the basis of a Nov9X sequence, a glycosylation site is continuously introduced according to a literature report (Improving specific activity and thermostability of *Escherichia coli* phytase by structure-based rational design). The sequence became one as shown in SEQ ID NO: 79, and the mutant was named as APPA-M2. Its heat stability can be further improved. In order to test whether the disulfide bond mutant described in Embodiment 1 can achieve a function on the phytase mutant APPA-M2 or not, the stability was further improved. The disulfide bonds B, C, D, M and O and disulfide bond combinations B+O, D+O, M+O and C+O were introduced on the basis of APPA-M2 according to a method in Embodiment 1. Each mutant was respectively named as APPA-M2-B, APPA-M2-C, APPA-M2-D, APPA-M2-M, APPA-M2-O, APPA-M2-BO, APPA-M2-DO, APPA-M2-MO and APPA-M2-CCX. The amino acid sequence of each mutant was as shown by SEQ ID Nos: 80-88. Corresponding nucleotide sequences were as shown by SEQ ID NOs: 90-98. Each mutant was expressed in *Aspergillus niger*. Then, heat stability was determined according to a method in Embodiment 2. The results were as shown in FIG. 5. The disulfide bonds adopted in the experiment all significantly improved the heat stability of the mutant. The effect of the combined disulfide bonds C+O was best. The residual activity after heat resistance treatment can reach 84.5%. The significant heat resistance characteristic was realized. It was predicted to have good performance in feed granulation. The above results showed that the proper combination can create more stable mutants. The above results showed that the introduction of the disulfide bonds provided by the inventor still showed very effective results on the phytase mutant sequence.

The inventor also tried continuously introducing a glycosylation site on the basis of the Nov9X sequence. Its sequence was as shown by SEQ ID NO: 99. The mutant was named as APPA-M3. Its heat stability can also be improved. Disulfide bonds C, C, D, M and O and disulfide bond combinations B+O, D+O, M+O, and C+O were introduced on the basis of APPA-M3 according to the method in Embodiment 1. Each mutant was respectively named as APPA-M3-B, APPA-M3-C, APPA-M3-D, APPA-M3-M, APPA-M3-O, APPA-M3-BO, APPA-M3-DO, APPA-M3-MO and APPA-M3-CCX. The amino acid sequence of each mutant was as shown by SEQ ID Nos: 100-108. Corresponding nucleotide sequences were as shown by SEQ ID NOs: 110-118. Each mutant was expressed in *Aspergillus niger*. Then, heat stability was determined according to the method in Embodiment 2. It was found that the disulfide bond introduced mutants achieve a good heat resistance characteristic like the disulfide bond introduced AMMA-M2 mutants. Identically, it was predicted to have good performance in feed granulation.

The modifications and variations of the method according to the present invention are obvious to a person skilled in the art, and do not deviate from the scope of the invention. Although the present invention is described with reference to particular embodiments, it should be understood that the invention requiring protection is not improperly limited to these particular exemplary embodiments. In fact, the various mutational modifications of wild-type phytase that are apparent to a person skilled in the art to achieve the technical effects of the present invention are covered by the claims.

What is claimed is:

1. A thermostable phytase variant having phytase activity that has at least 95% sequence identity to a polypeptide selected from the group consisting of the polypeptides of SEQ ID NO: 1, 2, 3, 79, and 99, wherein the phytase variant comprises a cysteine or a homocysteine residue at positions corresponding to positions 346 and 393 of the polypeptide of SEQ ID NO: 1, such that a disulfide bond is formed between the two residues, and optionally, the phytase variant further comprises one or more combinations of residues selected from (A) to (O), such that a disulfide bond is formed between the two residues of each combination:

(A) a cysteine or a homocysteine residue at positions corresponding to positions 34 and 174 of the polypeptide of SEQ ID NO: 1;
(B) a cysteine or a homocysteine residue at positions corresponding to positions 56 and 103 of the polypeptide of SEQ ID NO: 1;
(C) a cysteine or a homocysteine residue at positions corresponding to positions 57 and 366 of the polypeptide of SEQ ID NO: 1;
(D) a cysteine or a homocysteine residue at positions corresponding to positions 61 and 366 of the polypeptide of SEQ ID NO: 1;
(E) a cysteine or a homocysteine residue at positions corresponding to positions 82 and 296 of the polypeptide of SEQ ID NO: 1;
(F) a cysteine or a homocysteine residue at positions corresponding to positions 128 and 203 of the polypeptide of SEQ ID NO: 1;
(G) a cysteine or a homocysteine residue at positions corresponding to positions 140 and 262 of the polypeptide of SEQ ID NO: 1;
(H) a cysteine or a homocysteine residue at positions corresponding to positions 156 and 191 of the polypeptide of SEQ ID NO: 1;
(I) a cysteine or a homocysteine residue at positions corresponding to positions 165 and 245 of the polypeptide of SEQ ID NO: 1;
(J) a cysteine or a homocysteine residue at positions corresponding to positions 191 and 210 of the polypeptide of SEQ ID NO: 1;
(K) a cysteine or a homocysteine residue at positions corresponding to positions 196 and 211 of the polypeptide of SEQ ID NO: 1;
(L) a cysteine or a homocysteine residue at positions corresponding to positions 264 and 312 of the polypeptide of SEQ ID NO: 1;
(M) a cysteine or a homocysteine residue at positions corresponding to positions 315 and 380 of the polypeptide of SEQ ID NO: 1;
(N) a cysteine or a homocysteine residue at positions corresponding to positions 322 and 356 of the polypeptide of SEQ ID NO: 1; and
(O) a cysteine or a homocysteine residue at positions corresponding to positions 349 and 390 of the polypeptide of SEQ ID NO: 1;
wherein the thermostable phytase variant does not comprise the combinations of residues of (C) and (D) at the same time; or does not comprise the combinations of residues (H) and (J) at the same time.

2. The thermostable phytase variant according to claim 1, wherein the thermostable phytase variant comprises at least one combination of residues selected from (A), (B), (C), (D), (E), (J), or (M), but not both (C) and (D) at the same time.

3. The thermostable phytase variant according to claim 2, wherein the thermostable phytase variant comprises one, two, or more combinations of residues selected from (A), (B), (C), (D), (E), (J), and (M), but not both (C) and (D) at the same time.

4. The thermostable phytase variant according to claim 2, wherein the thermostable phytase variant comprises the combination of residues of (A), (B), (C), (E), (J) or (M).

5. The thermostable phytase variant according to claim 2, wherein the thermostable phytase variant further comprises the combination of residues of (D).

6. The thermostable phytase variant according to claim 2, wherein the thermostable phytase variant comprises the combinations of residues of (B); (C); (D); (M); (B) and (D); or (D) and (M).

7. The thermostable phytase variant according to claim 6, wherein the thermostable phytase variant comprises the combination of residues of (B).

8. The thermostable phytase variant according to claim 6, wherein the thermostable phytase variant comprises the combination of residues of (C).

9. The thermostable phytase variant according to claim 6, wherein the thermostable phytase variant comprises the combination of residues of (M).

10. The thermostable phytase variant according to claim 6, wherein the thermostable phytase variant comprises the combinations of residues of (B) and (D).

11. The thermostable phytase variant according to claim 6, wherein the thermostable phytase variant comprises the combinations of residues of (D) and (M).

12. The thermostable phytase variant according to claim 1, wherein the phytase variant comprises at least one combination of residues selected from
   (i) a cysteine or homocysteine residue at the positions corresponding to positions 31 and 176 of the polypeptide of SEQ ID NO: 1;
   (ii) a cysteine or homocysteine residue at the positions corresponding to positions 31 and 177 of the polypeptide of SEQ ID NO: 1;
   (iii) a cysteine or homocysteine residue at the positions corresponding to positions 52 and 99 of the polypeptide of SEQ ID NO: 1;
   (iv) a cysteine or homocysteine residue at the positions corresponding to positions 59 and 100 of the polypeptide of SEQ ID NO: 1;
   (v) a cysteine or homocysteine residue at the positions corresponding to positions 91 and 46 of the polypeptide of SEQ ID NO: 1;
   (vi) a cysteine or homocysteine residue at the positions corresponding to positions 141 and 200 of the polypeptide of SEQ ID NO: 1;
   (vii) a cysteine or homocysteine residue at the positions corresponding to positions 162 and 248 of the polypeptide of SEQ ID NO: 1; and
   (viii) a cysteine or homocysteine residue at the positions corresponding to positions 205 and 257 of the polypeptide of SEQ ID NO: 1;
wherein the thermostable phytase variant does not comprise the combinations of residues of (i) and (ii) at the same time.

13. The thermostable phytase variant according to claim 1, wherein the thermostable phytase variant comprises the amino acid sequence of SEQ ID NO: 18.

14. The thermostable phytase variant according to claim 1, wherein the thermostable phytase variant is obtained through heterologous expression in a *Pichia* or *Aspergillus niger* host.

15. The thermostable phytase variant according to claim 1, wherein the disulfide bond is formed between two cysteine residues or two homocysteine residues.

* * * * *

SEQUENCE LISTING

```
<160> NUMBER OF SEQ ID NOS: 118

<210> SEQ ID NO 1
<211> LENGTH: 410
<212> TYPE: PRT
<213> ORGANISM: Aspergillus niger

<400> SEQUENCE: 1

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160
```

-continued

Thr Ala Phe Arg Glu Leu Glu Arg Val Leu Asn Phe Pro Gln Ser Asn
            165                 170                 175

Leu Cys Leu Lys Arg Glu Lys Gln Asp Glu Ser Cys Ser Leu Thr Gln
        180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
            245                 250                 255

Leu Gln Arg Thr Pro Glu Val Ala Arg Ser Arg Ala Thr Pro Leu Leu
        260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Leu Val Phe Glu
            325                 330                 335

Arg Trp Arg Arg Leu Ser Asp Asn Ser Gln Trp Ile Gln Val Ser Leu
        340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
            405                 410

<210> SEQ ID NO 2
<211> LENGTH: 410
<212> TYPE: PRT
<213> ORGANISM: Artificial Sequence
<220> FEATURE:
<223> OTHER INFORMATION: NOV9X

<400> SEQUENCE: 2

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Gly Leu Pro Lys Cys Gly Cys Pro Gln Ser
65              70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

```
His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Cys Val Ser Leu Thr
                195                 200                 205

Gly Ala Val Ser Leu Ala Ser Met Leu Thr Glu Ile Phe Leu Leu Gln
            210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
                275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
                355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 3
<211> LENGTH: 410
<212> TYPE: PRT
<213> ORGANISM: Artificial Sequence
<220> FEATURE:
<223> OTHER INFORMATION: APPA-M1

<400> SEQUENCE: 3

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60
```

```
Arg Leu Val Ala Asp Glu Leu Leu Pro Lys Cys Gly Cys Pro Gln Ser
 65                  70                  75                  80

Gly Gln Val Ala Ile Ile Ala Asp Val Asp Glu Arg Thr Arg Lys Thr
                 85                  90                  95

Gly Glu Ala Phe Ala Ala Gly Leu Ala Pro Asp Cys Ala Ile Thr Val
                100                 105                 110

His His Gln Ala Asp Thr Ser Ser Pro Asp Pro Leu Phe Asn Pro Leu
                115                 120                 125

Lys Thr Gly Val Cys Gln Leu Asp Val Ala Asn Val Thr Arg Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
                195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
                275                 280                 285

Tyr Gly Val Thr Leu Pro Thr Ser Val Leu Phe Ile Ala Gly His Asp
                290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
                355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 4
<211> LENGTH: 410
<212> TYPE: PRT
<213> ORGANISM: Artificial Sequence
<220> FEATURE:
<223> OTHER INFORMATION: APPA-A

<400> SEQUENCE: 4

Gln Ser Glu Pro Glu Leu Lys Leu Glu Ser Val Val Ile Val Ser Arg
1               5                   10                  15
```

His Gly Val Arg Ala Pro Thr Lys Ala Thr Gln Leu Met Gln Asp Val
                 20                  25                  30

Thr Cys Asp Ala Trp Pro Thr Trp Pro Val Lys Leu Gly Trp Leu Thr
             35                  40                  45

Pro Arg Gly Gly Glu Leu Ile Ala Tyr Leu Gly His Tyr Gln Arg Gln
         50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                 85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Cys Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 5
<211> LENGTH: 410
<212> TYPE: PRT

<213> ORGANISM: Artificial Sequence
<220> FEATURE:
<223> OTHER INFORMATION: APPA-B

<400> SEQUENCE: 5

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Cys Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Cys Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
```

Asn Glu Ala Arg Ile Pro Ala Cys Ser Leu
            405                 410

<210> SEQ ID NO 6
<211> LENGTH: 410
<212> TYPE: PRT
<213> ORGANISM: Artificial Sequence
<220> FEATURE:
<223> OTHER INFORMATION: APPA-C

<400> SEQUENCE: 6

Gln Ser Glu Pro Glu Leu Lys Leu Glu Ser Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Cys Leu Gly His Tyr Gln Arg Gln
        50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu

```
                     340                 345                 350
Val Phe Gln Thr Leu Gln Gln Met Arg Asp Lys Thr Pro Cys Ser Leu
            355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 7
<211> LENGTH: 410
<212> TYPE: PRT
<213> ORGANISM: Artificial Sequence
<220> FEATURE:
<223> OTHER INFORMATION: APPA-D

<400> SEQUENCE: 7

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Cys Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
```

```
                    290                 295                 300
Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Cys Ser Leu
                355                 360                 365

Asn Thr Pro Pro Gly Glu Val Lys Leu Thr Leu Ala Gly Cys Glu Glu
                370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 8
<211> LENGTH: 410
<212> TYPE: PRT
<213> ORGANISM: Artificial Sequence
<220> FEATURE:
<223> OTHER INFORMATION: APPA-E

<400> SEQUENCE: 8

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
        50                  55                  60

Arg Leu Val Ala Asp Gly Leu Leu Ala Lys Lys Gly Cys Pro Gln Ser
65                  70                  75                  80

Gly Cys Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
        130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
        210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
```

```
               245                 250                 255
Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
            275                 280                 285

Tyr Gly Val Thr Leu Pro Thr Cys Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
            325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 9
<211> LENGTH: 410
<212> TYPE: PRT
<213> ORGANISM: Artificial Sequence
<220> FEATURE:
<223> OTHER INFORMATION: APPA-F

<400> SEQUENCE: 9

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Cys
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Cys Asn Val Ser Leu Thr
```

```
                195                 200                 205
Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Gln Lys Gln Ala
                275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
                355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 10
<211> LENGTH: 410
<212> TYPE: PRT
<213> ORGANISM: Artificial Sequence
<220> FEATURE:
<223> OTHER INFORMATION: APPA-G

<400> SEQUENCE: 10

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
        50                  55                  60

Arg Leu Val Ala Asp Gly Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Cys Thr Asp Ala Ile
        130                 135                 140

Leu Ser Arg Ala Gly Gly Ser Ile Ala Asp Phe Thr Gly His Arg Gln
```

```
                145                 150                 155                 160
        Thr Ala Phe Arg Glu Leu Glu Arg Val Leu Asn Phe Pro Gln Ser Asn
                        165                 170                 175

Leu Cys Leu Lys Arg Glu Lys Gln Asp Glu Ser Cys Ser Leu Thr Gln
                        180                 185                 190

Ala Leu Pro Ser Glu Leu Lys Val Ser Ala Asp Asn Val Ser Leu Thr
                        195                 200                 205

Gly Ala Val Ser Leu Ala Ser Met Leu Thr Glu Ile Phe Leu Leu Gln
                        210                 215                 220

Gln Ala Gln Gly Met Pro Glu Pro Gly Trp Gly Arg Ile Thr Asp Ser
        225                 230                 235                 240

His Gln Trp Asn Thr Leu Leu Ser Leu His Asn Ala Gln Phe Tyr Leu
                        245                 250                 255

Leu Gln Arg Thr Pro Cys Val Ala Arg Ser Arg Ala Thr Pro Leu Leu
                        260                 265                 270

Asp Leu Ile Lys Thr Ala Leu Thr Pro His Pro Pro Gln Lys Gln Ala
                        275                 280                 285

Tyr Gly Val Thr Leu Pro Thr Ser Val Leu Phe Ile Ala Gly His Asp
                        290                 295                 300

Thr Asn Leu Ala Asn Leu Gly Gly Ala Leu Glu Leu Asn Trp Thr Leu
        305                 310                 315                 320

Pro Gly Gln Pro Asp Asn Thr Pro Gly Gly Glu Leu Val Phe Glu
                        325                 330                 335

Arg Trp Arg Arg Leu Ser Asp Asn Ser Gln Trp Ile Gln Val Ser Leu
                        340                 345                 350

Val Phe Gln Thr Leu Gln Gln Met Arg Asp Lys Thr Pro Leu Ser Leu
                        355                 360                 365

Asn Thr Pro Pro Gly Glu Val Lys Leu Thr Leu Ala Gly Cys Glu Glu
                        370                 375                 380

Arg Asn Ala Gln Gly Met Cys Ser Leu Ala Gly Phe Thr Gln Ile Val
        385                 390                 395                 400

Asn Glu Ala Arg Ile Pro Ala Cys Ser Leu
                        405                 410

<210> SEQ ID NO 11
<211> LENGTH: 410
<212> TYPE: PRT
<213> ORGANISM: Artificial Sequence
<220> FEATURE:
<223> OTHER INFORMATION: APPA-H

<400> SEQUENCE: 11

Gln Ser Glu Pro Glu Leu Lys Leu Glu Ser Val Val Ile Val Ser Arg
        1               5                   10                  15

His Gly Val Arg Ala Pro Thr Lys Ala Thr Gln Leu Met Gln Asp Val
                        20                  25                  30

Thr Pro Asp Ala Trp Pro Thr Trp Pro Val Lys Leu Gly Trp Leu Thr
                        35                  40                  45

Pro Arg Gly Gly Glu Leu Ile Ala Tyr Leu Gly His Tyr Gln Arg Gln
                        50                  55                  60

Arg Leu Val Ala Asp Gly Leu Leu Ala Lys Lys Gly Cys Pro Gln Ser
        65                  70                  75                  80

Gly Gln Val Ala Ile Ile Ala Asp Val Asp Glu Arg Thr Arg Lys Thr
                        85                  90                  95

Gly Glu Ala Phe Ala Ala Gly Leu Ala Pro Asp Cys Ala Ile Thr Val
```

-continued

```
                100                 105                 110
His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
130                 135                 140

Leu Ser Arg Ala Gly Ser Ile Ala Asp Phe Cys Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Cys Gln
            180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
            210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 12
<211> LENGTH: 410
<212> TYPE: PRT
<213> ORGANISM: Artificial Sequence
<220> FEATURE:
<223> OTHER INFORMATION: APPA-I

<400> SEQUENCE: 12

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
```

```
            50                  55                  60
Arg Leu Val Ala Asp Gly Leu Ala Lys Lys Gly Cys Pro Gln Ser
 65                  70                  75                  80

Gly Gln Val Ala Ile Ile Ala Asp Val Asp Glu Arg Thr Arg Lys Thr
                 85                  90                  95

Gly Glu Ala Phe Ala Ala Gly Leu Ala Pro Asp Cys Ala Ile Thr Val
                100                 105                 110

His Thr Gln Ala Asp Thr Ser Ser Pro Asp Pro Leu Phe Asn Pro Leu
                115                 120                 125

Lys Thr Gly Val Cys Gln Leu Asp Asn Ala Asn Val Thr Asp Ala Ile
            130                 135                 140

Leu Ser Arg Ala Gly Gly Ser Ile Ala Asp Phe Thr Gly His Arg Gln
145                 150                 155                 160

Thr Ala Phe Arg Cys Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
                195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Cys Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gly Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 13
<211> LENGTH: 410
<212> TYPE: PRT
<213> ORGANISM: Artificial Sequence
<220> FEATURE:
<223> OTHER INFORMATION: APPA-J

<400> SEQUENCE: 13

Gln Ser Glu Pro Glu Leu Lys Leu Glu Ser Val Val Ile Val Ser Arg
```

```
1               5                   10                  15
His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
            50                  55                  60

Arg Leu Val Ala Asp Gly Leu Leu Ala Lys Lys Gly Cys Pro Gln Ser
65                      70                  75                  80

Gly Gln Val Ala Ile Ile Ala Asp Val Asp Glu Arg Thr Arg Lys Thr
                    85                  90                  95

Gly Glu Ala Phe Ala Ala Gly Leu Ala Pro Asp Cys Ala Ile Thr Val
                100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
            130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Cys Gln
            180                 185                 190

Ala Leu Pro Ser Glu Leu Lys Val Ser Ala Asp Asn Val Ser Leu Thr
            195                 200                 205

Gly Cys Val Ser Leu Ala Ser Met Leu Thr Glu Ile Phe Leu Leu Gln
            210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 14
```

```
<211> LENGTH: 410
<212> TYPE: PRT
<213> ORGANISM: Artificial Sequence
<220> FEATURE:
<223> OTHER INFORMATION: APPA-K

<400> SEQUENCE: 14

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Cys Glu Leu Lys Val Ser Ala Asp Asn Val Ser Leu Thr
        195                 200                 205

Gly Ala Cys Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380
```

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 15
<211> LENGTH: 410
<212> TYPE: PRT
<213> ORGANISM: Artificial Sequence
<220> FEATURE:
<223> OTHER INFORMATION: APPA-L

<400> SEQUENCE: 15

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Cys Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Cys Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 16
<211> LENGTH: 410
<212> TYPE: PRT
<213> ORGANISM: Artificial Sequence
<220> FEATURE:
<223> OTHER INFORMATION: APPA-M

<400> SEQUENCE: 16

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
        50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Cys Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Cys Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 17
<211> LENGTH: 410
<212> TYPE: PRT
<213> ORGANISM: Artificial Sequence
<220> FEATURE:
<223> OTHER INFORMATION: APPA-N

<400> SEQUENCE: 17

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

```
His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Cys Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Cys Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 18
<211> LENGTH: 410
<212> TYPE: PRT
<213> ORGANISM: Artificial Sequence
<220> FEATURE:
<223> OTHER INFORMATION: APPA-0

<400> SEQUENCE: 18

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190
```

```
Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
            245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Leu Val Phe Glu
            325                 330                 335

Arg Trp Arg Arg Leu Ser Asp Asn Ser Cys Trp Ile Gly Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Cys Ala Gly Phe Thr Gln Ile Val
385                 390                 395                 400

Asn Glu Ala Arg Ile Pro Ala Cys Ser Leu
            405                 410

<210> SEQ ID NO 19
<211> LENGTH: 410
<212> TYPE: PRT
<213> ORGANISM: Artificial Sequence
<220> FEATURE:
<223> OTHER INFORMATION: APPA-P

<400> SEQUENCE: 19

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
            50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
            85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
            130                 135                 140
```

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Cys Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
370                 375                 380

Arg Asn Ala Gln Gly Cys Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 20
<211> LENGTH: 410
<212> TYPE: PRT
<213> ORGANISM: Artificial Sequence
<220> FEATURE:
<223> OTHER INFORMATION: APPA-M1-D

<400> SEQUENCE: 20

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Tyr Leu Gly His Cys Trp Arg Gln
        50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His His Gln Ala Asp Thr Ser Ser Pro Asp Pro Leu Phe Asn Pro Leu
            115                 120                 125

Lys Thr Gly Val Cys Gln Leu Asp Val Ala Asn Val Thr Arg Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Cys Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 21
<211> LENGTH: 410
<212> TYPE: PRT
<213> ORGANISM: Artificial Sequence
<220> FEATURE:
<223> OTHER INFORMATION: APPA-M1-O

<400> SEQUENCE: 21

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

```
Pro Arg Gly Gly Glu Leu Ile Ala Tyr Leu Gly His Tyr Trp Arg Gln
 50                  55                  60

Arg Leu Val Ala Asp Glu Leu Leu Pro Lys Cys Gly Cys Pro Gln Ser
 65                  70                  75                  80

Gly Gln Val Ala Ile Ile Ala Asp Val Asp Glu Arg Thr Arg Lys Thr
                 85                  90                  95

Gly Glu Ala Phe Ala Ala Gly Leu Ala Pro Asp Cys Ala Ile Thr Val
                100                 105                 110

His His Gln Ala Asp Thr Ser Ser Pro Asp Pro Leu Phe Asn Pro Leu
                115                 120                 125

Lys Thr Gly Val Cys Gln Leu Asp Val Ala Asn Val Thr Arg Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
                195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
                275                 280                 285

Tyr Gly Val Thr Leu Pro Thr Ser Val Leu Phe Ile Ala Gly His Asp
                290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Cys Trp Ile Gln Val Ser Leu
                340                 345                 350

Val Phe Gln Thr Leu Gln Gln Met Arg Asp Lys Thr Pro Leu Ser Leu
                355                 360                 365

Asn Thr Pro Pro Gly Glu Val Lys Leu Thr Leu Ala Gly Cys Glu Glu
                370                 375                 380

Arg Asn Ala Gln Gly Met Cys Ser Cys Ala Gly Phe Thr Gln Ile Val
385                 390                 395                 400

Asn Glu Ala Arg Ile Pro Ala Cys Ser Leu
                405                 410

<210> SEQ ID NO 22
<211> LENGTH: 410
<212> TYPE: PRT
<213> ORGANISM: Artificial Sequence
<220> FEATURE:
<223> OTHER INFORMATION: APPA-M1-BO

<400> SEQUENCE: 22
```

```
Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Cys Tyr Leu Gly His Tyr Trp Arg Gln
    50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Cys Leu Ala Pro Asp Cys Ala Ile Thr Val
                100                 105                 110

His His Gln Ala Asp Thr Ser Ser Pro Asp Pro Leu Phe Asn Pro Leu
            115                 120                 125

Lys Thr Gly Val Cys Gln Leu Asp Val Ala Asn Val Thr Arg Ala Ile
        130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
        290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Cys Trp Ile Gln Val Ser Leu
                340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
        370                 375                 380

Arg Asn Ala Gln Gly Met Cys Ser Cys Ala Gly Phe Thr Gln Ile Val
385                 390                 395                 400

Asn Glu Ala Arg Ile Pro Ala Cys Ser Leu
                405                 410
```

<210> SEQ ID NO 23
<211> LENGTH: 410
<212> TYPE: PRT
<213> ORGANISM: Artificial Sequence
<220> FEATURE:
<223> OTHER INFORMATION: APPA-M1-CO

<400> SEQUENCE: 23

```
Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Cys Leu Gly His Tyr Trp Arg Gln
    50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Cys Trp Ile Gln Val Ser Leu
            340                 345                 350

Val Phe Gln Thr Leu Gln Gln Met Arg Asp Lys Thr Pro Cys Ser Leu
        355                 360                 365
```

```
Asn Thr Pro Pro Gly Glu Val Lys Leu Thr Leu Ala Gly Cys Glu Glu
        370                 375                 380

Arg Asn Ala Gln Gly Met Cys Ser Cys Ala Gly Phe Thr Gln Ile Val
385                 390                 395                 400

Asn Glu Ala Arg Ile Pro Ala Cys Ser Leu
            405                 410

<210> SEQ ID NO 24
<211> LENGTH: 410
<212> TYPE: PRT
<213> ORGANISM: Artificial Sequence
<220> FEATURE:
<223> OTHER INFORMATION: APPA-M1-DO

<400> SEQUENCE: 24

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Cys Trp Arg Gln
50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320
```

-continued

```
Pro Gly Gln Pro Asp Asn Thr Pro Pro Gly Glu Leu Val Phe Glu
            325                 330                 335

Arg Trp Arg Arg Leu Ser Asp Asn Ser Cys Trp Ile Gln Val Ser Leu
        340                 345                 350

Val Phe Gln Thr Leu Gln Gln Met Arg Asp Lys Thr Pro Cys Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Cys Ala Gly Phe Thr Gln Ile Val
385                 390                 395                 400

Asn Glu Ala Arg Ile Pro Ala Cys Ser Leu
                405                 410

<210> SEQ ID NO 25
<211> LENGTH: 410
<212> TYPE: PRT
<213> ORGANISM: Artificial Sequence
<220> FEATURE:
<223> OTHER INFORMATION: APPA-M1-MO

<400> SEQUENCE: 25

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270
```

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
        290                 295                 300

Thr Asn Leu Ala Asn Leu Gly Ala Leu Cys Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Cys Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Cys Gly Cys Glu Glu
370                 375                 380

Arg Asn Ala Gln Gly Met Cys Ser Cys Ala Gly Phe Thr Gln Ile Val
385                 390                 395                 400

Asn Glu Ala Arg Ile Pro Ala Cys Ser Leu
                405                 410

<210> SEQ ID NO 26
<211> LENGTH: 410
<212> TYPE: PRT
<213> ORGANISM: Artificial Sequence
<220> FEATURE:
<223> OTHER INFORMATION: APPA-M1-BDO

<400> SEQUENCE: 26

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Cys Tyr Leu Gly His Cys Trp Arg Gln
    50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Cys Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

```
Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
            245                 250                 255

Leu Gln Arg Thr Pro Glu Val Ala Arg Ser Arg Ala Thr Pro Leu Leu
        260                 265                 270

Asp Leu Ile Lys Thr Ala Leu Thr Pro His Pro Pro Gln Lys Gln Ala
    275                 280                 285

Tyr Gly Val Thr Leu Pro Thr Ser Val Leu Phe Ile Ala Gly His Asp
290                 295                 300

Thr Asn Leu Ala Asn Leu Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Cys Trp Ile Gln Val Ser Leu
                340                 345                 350

Val Phe Gln Thr Leu Gln Gln Met Arg Asp Lys Thr Pro Cys Ser Leu
        355                 360                 365

Asn Thr Pro Pro Gly Glu Val Lys Leu Thr Leu Ala Gly Cys Glu Glu
370                 375                 380

Arg Asn Ala Gln Gly Met Cys Ser Cys Ala Gly Phe Thr Gln Ile Val
385                 390                 395                 400

Asn Glu Ala Arg Ile Pro Ala Cys Ser Leu
                405                 410

<210> SEQ ID NO 27
<211> LENGTH: 410
<212> TYPE: PRT
<213> ORGANISM: Artificial Sequence
<220> FEATURE:
<223> OTHER INFORMATION: APPA-M1-DMO

<400> SEQUENCE: 27

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Tyr Leu Gly His Cys Trp Arg Gln
    50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175
```

```
Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Cys Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Cys Trp Ile Gln Val Ser Leu
            340                 345                 350

Val Phe Gln Thr Leu Gln Gln Met Arg Asp Lys Thr Pro Cys Ser Leu
        355                 360                 365

Asn Thr Pro Pro Gly Glu Val Lys Leu Thr Leu Cys Gly Cys Glu Glu
370                 375                 380

Arg Asn Ala Gln Gly Met Cys Ser Cys Ala Gly Phe Thr Gln Ile Val
385                 390                 395                 400

Asn Glu Ala Arg Ile Pro Ala Cys Ser Leu
                405                 410

<210> SEQ ID NO 28
<211> LENGTH: 410
<212> TYPE: PRT
<213> ORGANISM: Artificial Sequence
<220> FEATURE:
<223> OTHER INFORMATION: APPAan-A

<400> SEQUENCE: 28

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Cys Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125
```

```
Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Cys Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 29
<211> LENGTH: 410
<212> TYPE: PRT
<213> ORGANISM: Artificial Sequence
<220> FEATURE:
<223> OTHER INFORMATION: APPAan-B

<400> SEQUENCE: 29

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Cys Tyr Leu Gly His Tyr Gln Arg Gln
        50                  55                  60

Arg Leu Val Ala Asp Gly Leu Leu Ala Lys Lys Gly Cys Pro Gln Ser
65                  70                  75                  80
```

Gly Gln Val Ala Ile Ala Asp Val Asp Glu Arg Thr Arg Lys Thr
                85                  90                  95

Gly Glu Ala Phe Ala Ala Cys Leu Ala Pro Asp Cys Ala Ile Thr Val
            100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
        130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
        210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
        290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 30
<211> LENGTH: 410
<212> TYPE: PRT
<213> ORGANISM: Artificial Sequence
<220> FEATURE:
<223> OTHER INFORMATION: APPAan-C

<400> SEQUENCE: 30

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
          35                  40                  45

Pro Arg Gly Gly Glu Leu Ile Ala Cys Leu Gly His Tyr Gln Arg Gln
 50                  55                  60

Arg Leu Val Ala Asp Gly Leu Leu Ala Lys Lys Gly Cys Pro Gln Ser
 65                  70                  75                  80

Gly Gln Val Ala Ile Ile Ala Asp Val Asp Glu Arg Thr Arg Lys Thr
                 85                  90                  95

Gly Glu Ala Phe Ala Ala Gly Leu Ala Pro Asp Cys Ala Ile Thr Val
             100                 105                 110

His Thr Gln Ala Asp Thr Ser Ser Pro Asp Pro Leu Phe Asn Pro Leu
         115                 120                 125

Lys Thr Gly Val Cys Gln Leu Asp Asn Ala Asn Val Thr Asp Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Cys Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 31
<211> LENGTH: 410
<212> TYPE: PRT
<213> ORGANISM: Artificial Sequence
<220> FEATURE:
<223> OTHER INFORMATION: APPAan-D

<400> SEQUENCE: 31

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Cys Gln Arg Gln
        50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Cys Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
```

```
                405                 410
```

<210> SEQ ID NO 32
<211> LENGTH: 410
<212> TYPE: PRT
<213> ORGANISM: Artificial Sequence
<220> FEATURE:
<223> OTHER INFORMATION: APPAan-E

<400> SEQUENCE: 32

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Ala Lys Lys Gly Cys Pro Gln Ser
65                  70                  75                  80

Gly Cys Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Cys Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
```

```
                355                 360                 365
Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 33
<211> LENGTH: 410
<212> TYPE: PRT
<213> ORGANISM: Artificial Sequence
<220> FEATURE:
<223> OTHER INFORMATION: APPAan-F

<400> SEQUENCE: 33

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
        50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His Thr Gln Ala Asp Thr Ser Ser Pro Asp Pro Leu Phe Asn Pro Cys
            115                 120                 125

Lys Thr Gly Val Cys Gln Leu Asp Asn Ala Asn Val Thr Asp Ala Ile
        130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Cys Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
```

```
              305                 310                 315                 320
        Pro Gly Gln Pro Asp Asn Thr Pro Pro Gly Gly Glu Leu Val Phe Glu
                        325                 330                 335

Arg Trp Arg Arg Leu Ser Asp Asn Ser Gln Trp Ile Gln Val Ser Leu
                        340                 345                 350

Val Phe Gln Thr Leu Gln Gln Met Arg Asp Lys Thr Pro Leu Ser Leu
                        355                 360                 365

Asn Thr Pro Pro Gly Glu Val Lys Leu Thr Leu Ala Gly Cys Glu Glu
                        370                 375                 380

Arg Asn Ala Gln Gly Met Cys Ser Leu Ala Gly Phe Thr Gln Ile Val
        385                 390                 395                 400

Asn Glu Ala Arg Ile Pro Ala Cys Ser Leu
                        405                 410

<210> SEQ ID NO 34
<211> LENGTH: 410
<212> TYPE: PRT
<213> ORGANISM: Artificial Sequence
<220> FEATURE:
<223> OTHER INFORMATION: APPAan-I

<400> SEQUENCE: 34

Gln Ser Glu Pro Glu Leu Lys Leu Glu Ser Val Val Ile Val Ser Arg
        1               5                   10                  15

His Gly Val Arg Ala Pro Thr Lys Ala Thr Gln Leu Met Gln Asp Val
                        20                  25                  30

Thr Pro Asp Ala Trp Pro Thr Trp Pro Val Lys Leu Gly Trp Leu Thr
                        35                  40                  45

Pro Arg Gly Gly Glu Leu Ile Ala Tyr Leu Gly His Tyr Gln Arg Gln
                50                  55                  60

Arg Leu Val Ala Asp Gly Leu Leu Ala Lys Lys Gly Cys Pro Gln Ser
        65                  70                  75                  80

Gly Gln Val Ala Ile Ile Ala Asp Val Asp Glu Arg Thr Arg Lys Thr
                        85                  90                  95

Gly Glu Ala Phe Ala Ala Gly Leu Ala Pro Asp Cys Ala Ile Thr Val
                        100                 105                 110

His Thr Gln Ala Asp Thr Ser Ser Pro Asp Pro Leu Phe Asn Pro Leu
                        115                 120                 125

Lys Thr Gly Val Cys Gln Leu Asp Asn Ala Asn Val Thr Asp Ala Ile
                        130                 135                 140

Leu Ser Arg Ala Gly Gly Ser Ile Ala Asp Phe Thr Gly His Arg Gln
        145                 150                 155                 160

Thr Ala Phe Arg Cys Leu Glu Arg Val Leu Asn Phe Pro Gln Ser Asn
                        165                 170                 175

Leu Cys Leu Lys Arg Glu Lys Gln Asp Glu Ser Cys Ser Leu Thr Gln
                        180                 185                 190

Ala Leu Pro Ser Glu Leu Lys Val Ser Ala Asp Asn Val Ser Leu Thr
                        195                 200                 205

Gly Ala Val Ser Leu Ala Ser Met Leu Thr Glu Ile Phe Leu Leu Gln
                        210                 215                 220

Gln Ala Gln Gly Met Pro Glu Pro Gly Trp Gly Arg Ile Thr Asp Ser
        225                 230                 235                 240

His Gln Trp Asn Cys Leu Leu Ser Leu His Asn Ala Gln Phe Tyr Leu
                        245                 250                 255

Leu Gln Arg Thr Pro Glu Val Ala Arg Ser Arg Ala Thr Pro Leu Leu
```

```
                    260                 265                 270
Asp Leu Ile Lys Thr Ala Leu Thr Pro His Pro Gln Lys Gln Ala
                275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
                355                 360                 365

Asn Thr Pro Pro Gly Glu Val Lys Leu Thr Leu Ala Gly Cys Glu Glu
                370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 35
<211> LENGTH: 410
<212> TYPE: PRT
<213> ORGANISM: Artificial Sequence
<220> FEATURE:
<223> OTHER INFORMATION: APPAan-J

<400> SEQUENCE: 35

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
        50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Cys Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
```

```
                    210                 215                 220
Gln Ala Gln Gly Met Pro Glu Pro Gly Trp Gly Arg Ile Thr Asp Cys
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 36
<211> LENGTH: 410
<212> TYPE: PRT
<213> ORGANISM: Artificial Sequence
<220> FEATURE:
<223> OTHER INFORMATION: APPAan-K

<400> SEQUENCE: 36

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
        50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
```

165                 170                 175
Leu Cys Leu Lys Arg Glu Lys Gln Asp Glu Ser Cys Ser Leu Thr Gln
                180                 185                 190

Ala Leu Pro Cys Glu Leu Lys Val Ser Ala Asp Asn Val Ser Leu Thr
                195                 200                 205

Gly Ala Cys Ser Leu Ala Ser Met Leu Thr Glu Ile Phe Leu Leu Gln
            210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
                275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 37
<211> LENGTH: 410
<212> TYPE: PRT
<213> ORGANISM: Artificial Sequence
<220> FEATURE:
<223> OTHER INFORMATION: APPAan-L

<400> SEQUENCE: 37

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
        50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His Thr Gln Ala Asp Thr Ser Ser Pro Asp Pro Leu Phe Asn Pro Leu

```
            115                 120                 125
Lys Thr Gly Val Cys Gln Leu Asp Asn Ala Asn Val Thr Asp Ala Ile
130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Cys Arg Ser Arg Ala Thr Pro Leu Leu
                260                 265                 270

Asp Leu Ile Lys Thr Ala Leu Thr Pro His Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Cys Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
                355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 38
<211> LENGTH: 410
<212> TYPE: PRT
<213> ORGANISM: Artificial Sequence
<220> FEATURE:
<223> OTHER INFORMATION: APPAan-M

<400> SEQUENCE: 38

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
        50                  55                  60

Arg Leu Val Ala Asp Gly Leu Leu Ala Lys Lys Gly Cys Pro Gln Ser
```

```
              65                  70                  75                  80
        Gly Gln Val Ala Ile Ile Ala Asp Val Asp Glu Arg Thr Arg Lys Thr
                         85                  90                  95

Gly Glu Ala Phe Ala Ala Gly Leu Ala Pro Asp Cys Ala Ile Thr Val
                        100                 105                 110

His Thr Gln Ala Asp Thr Ser Ser Pro Asp Pro Leu Phe Asn Pro Leu
                        115                 120                 125

Lys Thr Gly Val Cys Gln Leu Asp Asn Ala Asn Val Thr Asp Ala Ile
        130                 135                 140

Leu Ser Arg Ala Gly Gly Ser Ile Ala Asp Phe Thr Gly His Arg Gln
        145                 150                 155                 160

Thr Ala Phe Arg Glu Leu Glu Arg Val Leu Asn Phe Pro Gln Ser Asn
                        165                 170                 175

Leu Cys Leu Lys Arg Glu Lys Gln Asp Glu Ser Cys Ser Leu Thr Gln
                        180                 185                 190

Ala Leu Pro Ser Glu Leu Lys Val Ser Ala Asp Asn Val Ser Leu Thr
                        195                 200                 205

Gly Ala Val Ser Leu Ala Ser Met Leu Thr Glu Ile Phe Leu Leu Gln
        210                 215                 220

Gln Ala Gln Gly Met Pro Glu Pro Gly Trp Gly Arg Ile Thr Asp Ser
        225                 230                 235                 240

His Gln Trp Asn Thr Leu Leu Ser Leu His Asn Ala Gln Phe Tyr Leu
                        245                 250                 255

Leu Gln Arg Thr Pro Glu Val Ala Arg Ser Arg Ala Thr Pro Leu Leu
                        260                 265                 270

Asp Leu Ile Lys Thr Ala Leu Thr Pro His Pro Pro Gln Lys Gln Ala
                        275                 280                 285

Tyr Gly Val Thr Leu Pro Thr Ser Val Leu Phe Ile Ala Gly His Asp
                        290                 295                 300

Thr Asn Leu Ala Asn Leu Gly Gly Ala Leu Cys Leu Asn Trp Thr Leu
        305                 310                 315                 320

Pro Gly Gln Pro Asp Asn Thr Pro Pro Gly Gly Glu Leu Val Phe Glu
                        325                 330                 335

Arg Trp Arg Arg Leu Ser Asp Asn Ser Gln Trp Ile Gln Val Ser Leu
                        340                 345                 350

Val Phe Gln Thr Leu Gln Gln Met Arg Asp Lys Thr Pro Leu Ser Leu
                        355                 360                 365

Asn Thr Pro Pro Gly Glu Val Lys Leu Thr Leu Cys Gly Cys Glu Glu
                        370                 375                 380

Arg Asn Ala Gln Gly Met Cys Ser Leu Ala Gly Phe Thr Gln Ile Val
        385                 390                 395                 400

Asn Glu Ala Arg Ile Pro Ala Cys Ser Leu
                        405                 410

<210> SEQ ID NO 39
<211> LENGTH: 410
<212> TYPE: PRT
<213> ORGANISM: Artificial Sequence
<220> FEATURE:
<223> OTHER INFORMATION: APPAan-N

<400> SEQUENCE: 39

Gln Ser Glu Pro Glu Leu Lys Leu Glu Ser Val Val Ile Val Ser Arg
        1               5                   10                  15

His Gly Val Arg Ala Pro Thr Lys Ala Thr Gln Leu Met Gln Asp Val
```

```
                20                  25                  30
Thr Pro Asp Ala Trp Pro Thr Trp Pro Val Lys Leu Gly Trp Leu Thr
            35                  40                  45
Pro Arg Gly Gly Glu Leu Ile Ala Tyr Leu Gly His Tyr Gln Arg Gln
        50                  55                  60
Arg Leu Val Ala Asp Gly Leu Leu Ala Lys Lys Gly Cys Pro Gln Ser
65                  70                  75                  80
Gly Gln Val Ala Ile Ile Ala Asp Val Asp Glu Arg Thr Arg Lys Thr
                85                  90                  95
Gly Glu Ala Phe Ala Ala Gly Leu Ala Pro Asp Cys Ala Ile Thr Val
                100                 105                 110
His Thr Gln Ala Asp Thr Ser Ser Pro Asp Pro Leu Phe Asn Pro Leu
            115                 120                 125
Lys Thr Gly Val Cys Gln Leu Asp Asn Ala Asn Val Thr Asp Ala Ile
        130                 135                 140
Leu Ser Arg Ala Gly Gly Ser Ile Ala Asp Phe Thr Gly His Arg Gln
145                 150                 155                 160
Thr Ala Phe Arg Glu Leu Glu Arg Val Leu Asn Phe Pro Gln Ser Asn
                165                 170                 175
Leu Cys Leu Lys Arg Glu Lys Gln Asp Glu Ser Cys Ser Leu Thr Gln
                180                 185                 190
Ala Leu Pro Ser Glu Leu Lys Val Ser Ala Asp Asn Val Ser Leu Thr
            195                 200                 205
Gly Ala Val Ser Leu Ala Ser Met Leu Thr Glu Ile Phe Leu Leu Gln
        210                 215                 220
Gln Ala Gln Gly Met Pro Glu Pro Gly Trp Gly Arg Ile Thr Asp Ser
225                 230                 235                 240
His Gln Trp Asn Thr Leu Leu Ser Leu His Asn Ala Gln Phe Tyr Leu
                245                 250                 255
Leu Gln Arg Thr Pro Glu Val Ala Arg Ser Arg Ala Thr Pro Leu Leu
                260                 265                 270
Asp Leu Ile Lys Thr Ala Leu Thr Pro His Pro Pro Gln Lys Gln Ala
            275                 280                 285
Tyr Gly Val Thr Leu Pro Thr Ser Val Leu Phe Ile Ala Gly His Asp
        290                 295                 300
Thr Asn Leu Ala Asn Leu Gly Gly Ala Leu Glu Leu Asn Trp Thr Leu
305                 310                 315                 320
Pro Cys Gln Pro Asp Asn Thr Pro Pro Gly Gly Glu Leu Val Phe Glu
                325                 330                 335
Arg Trp Arg Arg Leu Ser Asp Asn Ser Gln Trp Ile Gln Val Ser Leu
                340                 345                 350
Val Phe Gln Cys Leu Gln Gln Met Arg Asp Lys Thr Pro Leu Ser Leu
            355                 360                 365
Asn Thr Pro Pro Gly Glu Val Lys Leu Thr Leu Ala Gly Cys Glu Glu
        370                 375                 380
Arg Asn Ala Gln Gly Met Cys Ser Leu Ala Gly Phe Thr Gln Ile Val
385                 390                 395                 400
Asn Glu Ala Arg Ile Pro Ala Cys Ser Leu
                405                 410

<210> SEQ ID NO 40
<211> LENGTH: 410
<212> TYPE: PRT
<213> ORGANISM: Artificial Sequence
```

```
<220> FEATURE:
<223> OTHER INFORMATION: APPAan-O

<400> SEQUENCE: 40

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
        130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
        210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
        290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Cys Trp Ile Gln Val Ser Leu
                340                 345                 350

Val Phe Gln Thr Leu Gln Met Arg Asp Lys Thr Pro Leu Ser Leu
            355                 360                 365

Asn Thr Pro Pro Gly Glu Val Lys Leu Thr Leu Ala Gly Cys Glu Glu
        370                 375                 380

Arg Asn Ala Gln Gly Met Cys Ser Cys Ala Gly Phe Thr Gln Ile Val
385                 390                 395                 400
```

Asn Glu Ala Arg Ile Pro Ala Cys Ser Leu
            405                 410

<210> SEQ ID NO 41
<211> LENGTH: 1233
<212> TYPE: DNA
<213> ORGANISM: Artificial Sequence
<220> FEATURE:
<223> OTHER INFORMATION: APPA-A

<400> SEQUENCE: 41

| | | | | | |
|---|---|---|---|---|---|
| cagagtgagc | ctgagttgaa | actggaatcc | gttgtcatcg | tctctagaca | tggtgttaga | 60 |
| gcaccaacca | aggccaccca | acttatgcaa | gatgtcacct | gtgacgcttg | gccaacctgg | 120 |
| ccagtcaagc | tgggttggtt | gacacctaga | ggtggtgagc | tcattgctta | cttgggtcac | 180 |
| taccaaagac | agcgtcttgt | tgccgacgga | ttgttggcca | agaagggttg | tccacaatct | 240 |
| ggtcaagtag | ctattattgc | tgacgtcgac | gaaagaaccc | gtaagacagg | tgaagccttc | 300 |
| gccgccggtc | ttgctcctga | ctgtgccatt | accgttcaca | cccaagctga | cacttcttct | 360 |
| ccagatccat | tgttcaaccc | tttgaagact | ggtgtttgcc | aattggacaa | cgctaacgtt | 420 |
| actgacgcta | tcttgtccag | agctggagga | tccattgctg | acttcaccgg | tcacagacag | 480 |
| actgccttca | gagagttgga | aagagttctt | aacttcccat | gttcaaactt | gtgcttgaag | 540 |
| cgtgagaagc | aagacgaatc | ctgttccttg | actcaagcat | accatctgat | gttgaaggtc | 600 |
| tccgccgaca | acgtctcttt | gaccggtgct | gtcagcttgg | cttccatgtt | gactgaaatc | 660 |
| tttcttctgc | aacaagctca | aggtatgcct | gagccaggtt | ggggtagaat | caccgactct | 720 |
| caccaatgga | acaccttgtt | gtccttgcac | aacgctcaat | tctacttgct | gcagagaact | 780 |
| ccagaggttg | ctagatccag | agccaccca | ttgttggact | tgatcaagac | tgctttgact | 840 |
| cctcacccac | tcaaaagca | agcctacggt | gttaccttgc | ccacttctgt | cttgttcatt | 900 |
| gccggtcacg | atactaactt | ggcaaatctc | ggcggtgctt | tggagttgaa | ctggactctt | 960 |
| cctggtcaac | tgataacac | tccaccaggt | ggtgagctcg | ttttcgaaag | atggcgtaga | 1020 |
| ctatctgata | ctctcaatg | gattcaggtt | tcgttggtct | tccaaacttt | gcagcagatg | 1080 |
| agagacaaga | ctccactgtc | tttgaacacg | cctccaggag | aagtcaaatt | gaccttggct | 1140 |
| ggatgtgaag | agagaaatgc | tcagggtatg | tgttccttgg | ctggttttcac | tcaaatcgtt | 1200 |
| aacgaagcta | gaatcccagc | ttgttccttg | tag | | | 1233 |

<210> SEQ ID NO 42
<211> LENGTH: 1233
<212> TYPE: DNA
<213> ORGANISM: Artificial Sequence
<220> FEATURE:
<223> OTHER INFORMATION: APPA-B

<400> SEQUENCE: 42

| | | | | | |
|---|---|---|---|---|---|
| cagagtgagc | ctgagttgaa | actggaatcc | gttgtcatcg | tctctagaca | tggtgttaga | 60 |
| gcaccaacca | aggccaccca | acttatgcaa | gatgtcaccc | cagacgcttg | gccaacctgg | 120 |
| ccagtcaagc | tgggttggtt | gacacctaga | ggtggtgagc | tcatttgtta | cttgggtcac | 180 |
| taccaaagac | agcgtcttgt | tgccgacgga | ttgttggcca | agaagggttg | tccacaatct | 240 |
| ggtcaagtag | ctattattgc | tgacgtcgac | gaaagaaccc | gtaagacagg | tgaagccttc | 300 |
| gccgcctgtc | ttgctcctga | ctgtgccatt | accgttcaca | cccaagctga | cacttcttct | 360 |
| ccagatccat | tgttcaaccc | tttgaagact | ggtgtttgcc | aattggacaa | cgctaacgtt | 420 |

```
actgacgcta tcttgtccag agctggagga tccattgctg acttcaccgg tcacagacag        480
actgccttca gagagttgga aagagttctt aacttcccac aatcaaactt gtgcttgaag        540
cgtgagaagc aagacgaatc ctgttccttg actcaagcat taccatctga gttgaaggtc        600
tccgccgaca acgtctcttt gaccggtgct gtcagcttgg cttccatgtt gactgaaatc        660
tttcttctgc aacaagctca aggtatgcct gagccaggtt ggggtagaat caccgactct        720
caccaatgga acaccttgtt gtccttgcac aacgctcaat tctacttgct gcagagaact        780
ccagaggttg ctagatccag agccacccca ttgttggact tgatcaagac tgctttgact        840
cctcacccac ctcaaaagca agcctacggt gttaccttgc ccacttctgt cttgttcatt        900
gccggtcacg atactaactt ggcaaatctc ggcggtgctt tggagttgaa ctggactctt        960
cctggtcaac ctgataacac tccaccaggt ggtgagctcg ttttcgaaag atggcgtaga       1020
ctatctgata actctcaatg gattcaggtt tcgttggtct tccaaacttt gcagcagatg       1080
agagacaaga ctccactgtc tttgaacacg cctccaggag aagtcaaatt gaccttggct       1140
ggatgtgaag agagaaatgc tcagggtatg tgttccttgg ctggtttcac tcaaatcgtt       1200
aacgaagcta gaatcccagc ttgttccttg tag                                    1233

<210> SEQ ID NO 43
<211> LENGTH: 1233
<212> TYPE: DNA
<213> ORGANISM: Artificial Sequence
<220> FEATURE:
<223> OTHER INFORMATION: APPA-C

<400> SEQUENCE: 43
cagagtgagc ctgagttgaa actggaatcc gttgtcatcg tctctagaca tggtgttaga         60
gcaccaacca aggccaccca acttatgcaa gatgtcaccc cagacgcttg gccaacctgg        120
ccagtcaagc tgggttggtt gacacctaga ggtggtgagc tcattgcttg tttgggtcac        180
taccaaagac agcgtcttgt tgccgacgga ttgttggcca agaagggttg tccacaatct        240
ggtcaagtag ctattattgc tgacgtcgac gaaagaaccc gtaagacagg tgaagccttc        300
gccgccggtc ttgctcctga ctgtgccatt accgttcaca cccaagctga cacttcttct        360
ccagatccat tgttcaaccc tttgaagact ggtgtttgcc aattggacaa cgctaacgtt        420
actgacgcta tcttgtccag agctggagga tccattgctg acttcaccgg tcacagacag        480
actgccttca gagagttgga aagagttctt aacttcccac aatcaaactt gtgcttgaag        540
cgtgagaagc aagacgaatc ctgttccttg actcaagcat taccatctga gttgaaggtc        600
tccgccgaca acgtctcttt gaccggtgct gtcagcttgg cttccatgtt gactgaaatc        660
tttcttctgc aacaagctca aggtatgcct gagccaggtt ggggtagaat caccgactct        720
caccaatgga acaccttgtt gtccttgcac aacgctcaat tctacttgct gcagagaact        780
ccagaggttg ctagatccag agccacccca ttgttggact tgatcaagac tgctttgact        840
cctcacccac ctcaaaagca agcctacggt gttaccttgc ccacttctgt cttgttcatt        900
gccggtcacg atactaactt ggcaaatctc ggcggtgctt tggagttgaa ctggactctt        960
cctggtcaac ctgataacac tccaccaggt ggtgagctcg ttttcgaaag atggcgtaga       1020
ctatctgata actctcaatg gattcaggtt tcgttggtct tccaaacttt gcagcagatg       1080
agagacaaga ctccatgttc tttgaacacg cctccaggag aagtcaaatt gaccttggct       1140
ggatgtgaag agagaaatgc tcagggtatg tgttccttgg ctggtttcac tcaaatcgtt       1200
```

```
aacgaagcta gaatcccagc ttgttccttg tag                                  1233
```

<210> SEQ ID NO 44
<211> LENGTH: 1233
<212> TYPE: DNA
<213> ORGANISM: Artificial Sequence
<220> FEATURE:
<223> OTHER INFORMATION: APPA-D

<400> SEQUENCE: 44

```
cagagtgagc ctgagttgaa actggaatcc gttgtcatcg tctctagaca tggtgttaga      60
gcaccaacca aggccaccca acttatgcaa gatgtcaccc cagacgcttg gccaacctgg     120
ccagtcaagc tgggttggtt gacacctaga ggtggtgagc tcattgctta cttgggtcac     180
tgtcaaagac agcgtcttgt tgccgacgga ttgttggcca agaagggttg tccacaatct     240
ggtcaagtag ctattattgc tgacgtcgac gaaagaaccc gtaagacagg tgaagccttc     300
gccgccggtc ttgctcctga ctgtgccatt accgttcaca cccaagctga cacttcttct     360
ccagatccat tgttcaaccc tttgaagact ggtgtttgcc aattggacaa cgctaacgtt     420
actgacgcta tcttgtccag agctggagga tccattgctg acttcaccgg tcacagacag     480
actgccttca gagagttgga aagagttctt aacttcccac aatcaaactt gtgcttgaag     540
cgtgagaagc aagacgaatc ctgttccttg actcaagcat taccatctga gttgaaggtc     600
tccgccgaca acgtctcttt gaccggtgct gtcagcttgg cttccatgtt gactgaaatc     660
tttcttctgc aacaagctca aggtatgcct gagccaggtt ggggtagaat caccgactct     720
caccaatgga acaccttgtt gtccttgcac aacgctcaat tctacttgct gcagagaact     780
ccagaggttg ctagatccag agccaccccca ttgttggact tgatcaagac tgctttgact     840
cctcacccac ctcaaaagca agcctacggt gttaccttgc ccacttctgt cttgttcatt     900
gccggtcacg atactaactt ggcaaatctc ggcggtgctt tggagttgaa ctggactctt     960
cctggtcaac tgataacac tccaccaggt ggtgagctcg ttttcgaaag atggcgtaga    1020
ctatctgata actctcaatg gattcaggtt tcgttggtct tccaaacttt gcagcagatg    1080
agagacaaga ctccatgttc tttgaacacg cctccaggag aagtcaaatt gaccttggct    1140
ggatgtgaag agagaaatgc tcagggtatg tgttccttgg ctggtttcac tcaaatcgtt    1200
aacgaagcta gaatcccagc ttgttccttg tag                                 1233
```

<210> SEQ ID NO 45
<211> LENGTH: 1233
<212> TYPE: DNA
<213> ORGANISM: Artificial Sequence
<220> FEATURE:
<223> OTHER INFORMATION: APPA-E

<400> SEQUENCE: 45

```
cagagtgagc ctgagttgaa actggaatcc gttgtcatcg tctctagaca tggtgttaga      60
gcaccaacca aggccaccca acttatgcaa gatgtcaccc cagacgcttg gccaacctgg     120
ccagtcaagc tgggttggtt gacacctaga ggtggtgagc tcattgctta cttgggtcac     180
taccaaagac agcgtcttgt tgccgacgga ttgttggcca agaagggttg tccacaatct     240
ggttgtgtag ctattattgc tgacgtcgac gaaagaaccc gtaagacagg tgaagccttc     300
gccgccggtc ttgctcctga ctgtgccatt accgttcaca cccaagctga cacttcttct     360
ccagatccat tgttcaaccc tttgaagact ggtgtttgcc aattggacaa cgctaacgtt     420
actgacgcta tcttgtccag agctggagga tccattgctg acttcaccgg tcacagacag     480
```

```
actgccttca gagagttgga aagagttctt aacttcccac aatcaaactt gtgcttgaag      540
cgtgagaagc aagacgaatc ctgttccttg actcaagcat taccatctga gttgaaggtc      600
tccgccgaca acgtctcttt gaccggtgct gtcagcttgg cttccatgtt gactgaaatc      660
tttcttctgc aacaagctca aggtatgcct gagccaggtt ggggtagaat caccgactct      720
caccaatgga acaccttgtt gtccttgcac aacgctcaat tctacttgct gcagagaact      780
ccagaggttg ctagatccag agccacccca ttgttggact tgatcaagac tgctttgact      840
cctcacccac ctcaaaagca agcctacggt gttaccttgc ccacttgtgt cttgttcatt      900
gccggtcacg atactaactt ggcaaatctc ggcggtgctt tggagttgaa ctggactctt      960
cctggtcaac ctgataacac tccaccaggt ggtgagctcg ttttcgaaag atggcgtaga     1020
ctatctgata actctcaatg gattcaggtt tcgttggtct tccaaacttt gcagcagatg     1080
agagacaaga ctccactgtc tttgaacacg cctccaggag aagtcaaatt gaccttggct     1140
ggatgtgaag agagaaatgc tcagggtatg tgttccttgg ctggtttcac tcaaatcgtt     1200
aacgaagcta gaatcccagc ttgttccttg tag                                  1233
```

<210> SEQ ID NO 46
<211> LENGTH: 1233
<212> TYPE: DNA
<213> ORGANISM: Artificial Sequence
<220> FEATURE:
<223> OTHER INFORMATION: APPA-F

<400> SEQUENCE: 46

```
cagagtgagc ctgagttgaa actggaatcc gttgtcatcg tctctagaca tggtgttaga       60
gcaccaacca aggccaccca acttatgcaa gatgtcaccc cagacgcttg gccaacctgg      120
ccagtcaagc tgggttggtt gacacctaga ggtggtgagc tcattgctta cttgggtcac      180
taccaaagac agcgtcttgt tgccgacgga ttgttggcca agaagggttg tccacaatct      240
ggtcaagtag ctattattgc tgacgtcgac gaaagaaccc gtaagacagg tgaagccttc      300
gccgccggtc ttgctcctga ctgtgccatt accgttcaca cccaagctga cacttcttct      360
ccagatccat tgttcaaccc ttgtaagact ggtgtttgcc aattggacaa cgctaacgtt      420
actgacgcta tcttgtccag agctggagga tccattgctg acttcaccgg tcacagacag      480
actgccttca gagagttgga aagagttctt aacttcccac aatcaaactt gtgcttgaag      540
cgtgagaagc aagacgaatc ctgttccttg actcaagcat taccatctga gttgaaggtc      600
tccgccgtta acgtctcttt gaccggtgct gtcagcttgg cttccatgtt gactgaaatc      660
tttcttctgc aacaagctca aggtatgcct gagccaggtt ggggtagaat caccgactct      720
caccaatgga acaccttgtt gtccttgcac aacgctcaat tctacttgct gcagagaact      780
ccagaggttg ctagatccag agccacccca ttgttggact tgatcaagac tgctttgact      840
cctcacccac ctcaaaagca agcctacggt gttaccttgc ccacttctgt cttgttcatt      900
gccggtcacg atactaactt ggcaaatctc ggcggtgctt tggagttgaa ctggactctt      960
cctggtcaac ctgataacac tccaccaggt ggtgagctcg ttttcgaaag atggcgtaga     1020
ctatctgata actctcaatg gattcaggtt tcgttggtct tccaaacttt gcagcagatg     1080
agagacaaga ctccactgtc tttgaacacg cctccaggag aagtcaaatt gaccttggct     1140
ggatgtgaag agagaaatgc tcagggtatg tgttccttgg ctggtttcac tcaaatcgtt     1200
aacgaagcta gaatcccagc ttgttccttg tag                                  1233
```

<210> SEQ ID NO 47
<211> LENGTH: 1233
<212> TYPE: DNA
<213> ORGANISM: Artificial Sequence
<220> FEATURE:
<223> OTHER INFORMATION: APPA-G

<400> SEQUENCE: 47

| | | | | | |
|---|---|---|---|---|---|
| cagagtgagc | ctgagttgaa | actggaatcc | gttgtcatcg | tctctagaca | tggtgttaga | 60 |
| gcaccaacca | aggccaccca | acttatgcaa | gatgtcaccc | cagacgcttg | gccaacctgg | 120 |
| ccagtcaagc | tgggttggtt | gacacctaga | ggtggtgagc | tcattgctta | cttgggtcac | 180 |
| taccaaagac | agcgtcttgt | tgccgacgga | ttgttggcca | agaagggttg | tccacaatct | 240 |
| ggtcaagtag | ctattattgc | tgacgtcgac | gaaagaaccc | gtaagacagg | tgaagccttc | 300 |
| gccgccggtc | ttgctcctga | ctgtgccatt | accgttcaca | cccaagctga | cacttcttct | 360 |
| ccagatccat | tgttcaaccc | tttgaagact | ggtgtttgcc | aattggacaa | cgctaactgt | 420 |
| actgacgcta | tcttgtccag | agctggagga | tccattgctg | acttcaccgg | tcacagacag | 480 |
| actgccttca | gagagttgga | aagagttctt | aacttcccac | aatcaaactt | gtgcttgaag | 540 |
| cgtgagaagc | aagacgaatc | ctgttccttg | actcaagcat | accatctga | ttgaaggtc | 600 |
| tccgccgaca | acgtctcttt | gaccggtgct | gtcagcttgg | cttccatgtt | gactgaaatc | 660 |
| tttcttctgc | aacaagctca | aggtatgcct | gagccaggtt | ggggtagaat | caccgactct | 720 |
| caccaatgga | acaccttgtt | gtccttgcac | aacgctcaat | tctacttgct | gcagagaact | 780 |
| ccatgtgttg | ctagatccag | agccaccca | ttgttggact | tgatcaagac | tgctttgact | 840 |
| cctcacccac | ctcaaaagca | agcctacggt | gttaccttgc | ccacttctgt | cttgttcatt | 900 |
| gccggtcacg | atactaactt | ggcaaatctc | ggcggtgctt | tggagttgaa | ctggactctt | 960 |
| cctggtcaac | tgataacac | tccaccaggt | ggtgagctcg | ttttcgaaag | atggcgtaga | 1020 |
| ctatctgata | actctcaatg | gattcaggtt | tcgttggtct | tccaaacttt | gcagcagatg | 1080 |
| agagacaaga | ctccactgtc | tttgaacacg | cctccaggag | aagtcaaatt | gaccttggct | 1140 |
| ggatgtgaag | agagaaatgc | tcagggtatg | tgttccttgg | ctggtttcac | tcaaatcgtt | 1200 |
| aacgaagcta | gaatcccagc | ttgttccttg | tag | | | 1233 |

<210> SEQ ID NO 48
<211> LENGTH: 1233
<212> TYPE: DNA
<213> ORGANISM: Artificial Sequence
<220> FEATURE:
<223> OTHER INFORMATION: APPA-H

<400> SEQUENCE: 48

| | | | | | |
|---|---|---|---|---|---|
| cagagtgagc | ctgagttgaa | actggaatcc | gttgtcatcg | tctctagaca | tggtgttaga | 60 |
| gcaccaacca | aggccaccca | acttatgcaa | gatgtcaccc | cagacgcttg | gccaacctgg | 120 |
| ccagtcaagc | tgggttggtt | gacacctaga | ggtggtgagc | tcattgctta | cttgggtcac | 180 |
| taccaaagac | agcgtcttgt | tgccgacgga | ttgttggcca | agaagggttg | tccacaatct | 240 |
| ggtcaagtag | ctattattgc | tgacgtcgac | gaaagaaccc | gtaagacagg | tgaagccttc | 300 |
| gccgccggtc | ttgctcctga | ctgtgccatt | accgttcaca | cccaagctga | cacttcttct | 360 |
| ccagatccat | tgttcaaccc | tttgaagact | ggtgtttgcc | aattggacaa | cgctaacgtt | 420 |
| actgacgcta | tcttgtccag | agctggagga | tccattgctg | acttctgtgg | tcacagacag | 480 |
| actgccttca | gagagttgga | aagagttctt | aacttcccac | aatcaaactt | gtgcttgaag | 540 |

```
cgtgagaagc aagacgaatc ctgttccttg tgtcaagcat taccatctga gttgaaggtc    600
tccgccgaca acgtctcttt gaccggtgct gtcagcttgg cttccatgtt gactgaaatc    660
tttcttctgc aacaagctca aggtatgcct gagccaggtt ggggtagaat caccgactct    720
caccaatgga acaccttgtt gtccttgcac aacgctcaat tctacttgct gcagagaact    780
ccagaggttg ctagatccag agccacccca ttgttggact tgatcaagac tgctttgact    840
cctcacccac ctcaaaagca agcctacggt gttaccttgc ccacttctgt cttgttcatt    900
gccggtcacg atactaactt ggcaaatctc ggcggtgctt tggagttgaa ctggactctt    960
cctggtcaac tgataacac tccaccaggt ggtgagctcg ttttcgaaag atggcgtaga   1020
ctatctgata actctcaatg gattcaggtt tcgttggtct tccaaacttt gcagcagatg   1080
agagacaaga ctccactgtc tttgaacacg cctccaggag aagtcaaatt gaccttggct   1140
ggatgtgaag agagaaatgc tcagggtatg tgttccttgg ctggtttcac tcaaatcgtt   1200
aacgaagcta gaatcccagc ttgttccttg tag                                 1233

<210> SEQ ID NO 49
<211> LENGTH: 1233
<212> TYPE: DNA
<213> ORGANISM: Artificial Sequence
<220> FEATURE:
<223> OTHER INFORMATION: APPA-I

<400> SEQUENCE: 49
cagagtgagc ctgagttgaa actggaatcc gttgtcatcg tctctagaca tggtgttaga     60
gcaccaacca aggccaccca acttatgcaa gatgtcaccc cagacgcttg gccaacctgg    120
ccagtcaagc tgggttggtt gacacctaga ggtggtgagc tcattgctta cttgggtcac    180
taccaaagac agcgtcttgt tgccgacgga ttgttggcca agaagggttg tccacaatct    240
ggtcaagtag ctattattgc tgacgtcgac gaaagaaccc gtaagacagg tgaagccttc    300
gccgccggtc ttgctcctga ctgtgccatt accgttcaca cccaagctga cacttcttct    360
ccagatccat tgttcaaccc tttgaagact ggtgtttgcc aattggacaa cgctaacgtt    420
actgacgcta tcttgtccag agctggagga tccattgctg acttcaccgg tcacagacag    480
actgccttca gatgtttgga aagagttctt aacttcccac aatcaaactt gtgcttgaag    540
cgtgagaagc aagacgaatc ctgttccttg actcaagcat taccatctga gttgaaggtc    600
tccgccgaca acgtctcttt gaccggtgct gtcagcttgg cttccatgtt gactgaaatc    660
tttcttctgc aacaagctca aggtatgcct gagccaggtt ggggtagaat caccgactct    720
caccaatgga actgtttgtt gtccttgcac aacgctcaat tctacttgct gcagagaact    780
ccagaggttg ctagatccag agccacccca ttgttggact tgatcaagac tgctttgact    840
cctcacccac ctcaaaagca agcctacggt gttaccttgc ccacttctgt cttgttcatt    900
gccggtcacg atactaactt ggcaaatctc ggcggtgctt tggagttgaa ctggactctt    960
cctggtcaac tgataacac tccaccaggt ggtgagctcg ttttcgaaag atggcgtaga   1020
ctatctgata actctcaatg gattcaggtt tcgttggtct tccaaacttt gcagcagatg   1080
agagacaaga ctccactgtc tttgaacacg cctccaggag aagtcaaatt gaccttggct   1140
ggatgtgaag agagaaatgc tcagggtatg tgttccttgg ctggtttcac tcaaatcgtt   1200
aacgaagcta gaatcccagc ttgttccttg tag                                 1233

<210> SEQ ID NO 50
```

<211> LENGTH: 1233
<212> TYPE: DNA
<213> ORGANISM: Artificial Sequence
<220> FEATURE:
<223> OTHER INFORMATION: APPA-J

<400> SEQUENCE: 50

| | |
|---|---|
| cagagtgagc ctgagttgaa actggaatcc gttgtcatcg tctctagaca tggtgttaga | 60 |
| gcaccaacca aggccaccca acttatgcaa gatgtcaccc cagacgcttg gccaacctgg | 120 |
| ccagtcaagc tgggttggtt gacacctaga ggtggtgagc tcattgctta cttgggtcac | 180 |
| taccaaagac agcgtcttgt tgccgacgga ttgttggcca agaagggttg tccacaatct | 240 |
| ggtcaagtag ctattattgc tgacgtcgac gaaagaaccc gtaagacagg tgaagccttc | 300 |
| gccgccggtc ttgctcctga ctgtgccatt accgttcaca cccaagctga cacttcttct | 360 |
| ccagatccat tgttcaaccc tttgaagact ggtgtttgcc aattggacaa cgctaacgtt | 420 |
| actgacgcta tcttgtccag agctggagga tccattgctg acttcaccgg tcacagacag | 480 |
| actgccttca gagagttgga aagagttctt aacttcccac aatcaaactt gtgcttgaag | 540 |
| cgtgagaagc aagacgaatc ctgttccttg tgtcaagcat taccatctga gttgaaggtc | 600 |
| tccgccgaca acgtctcttt gaccggttgt gtcagcttgg cttccatgtt gactgaaatc | 660 |
| tttcttctgc aacaagctca aggtatgcct gagccaggtt ggggtagaat caccgactct | 720 |
| caccaatgga cacccttgtt gtccttgcac aacgctcaat tctacttgct gcagagaact | 780 |
| ccagaggttg ctagatccag agccacccca ttgttggact tgatcaagac tgctttgact | 840 |
| cctcacccac ctcaaaagca agcctacggt gttaccttgc ccacttctgt cttgttcatt | 900 |
| gccggtcacg atactaactt ggcaaatctc ggcggtgctt tggagttgaa ctggactctt | 960 |
| cctggtcaac tgataacac tccaccaggt ggtgagctcg ttttcgaaag atggcgtaga | 1020 |
| ctatctgata actctcaatg gattcaggtt tcgttggtct tccaaacttt gcagcagatg | 1080 |
| agagacaaga ctccactgtc tttgaacacg cctccaggag aagtcaaatt gaccttggct | 1140 |
| ggatgtgaag agagaaatgc tcagggtatg tgttccttgg ctggtttcac tcaaatcgtt | 1200 |
| aacgaagcta gaatcccagc ttgttccttg tag | 1233 |

<210> SEQ ID NO 51
<211> LENGTH: 1233
<212> TYPE: DNA
<213> ORGANISM: Artificial Sequence
<220> FEATURE:
<223> OTHER INFORMATION: APPA-K

<400> SEQUENCE: 51

| | |
|---|---|
| cagagtgagc ctgagttgaa actggaatcc gttgtcatcg tctctagaca tggtgttaga | 60 |
| gcaccaacca aggccaccca acttatgcaa gatgtcaccc cagacgcttg gccaacctgg | 120 |
| ccagtcaagc tgggttggtt gacacctaga ggtggtgagc tcattgctta cttgggtcac | 180 |
| taccaaagac agcgtcttgt tgccgacgga ttgttggcca agaagggttg tccacaatct | 240 |
| ggtcaagtag ctattattgc tgacgtcgac gaaagaaccc gtaagacagg tgaagccttc | 300 |
| gccgccggtc ttgctcctga ctgtgccatt accgttcaca cccaagctga cacttcttct | 360 |
| ccagatccat tgttcaaccc tttgaagact ggtgtttgcc aattggacaa cgctaacgtt | 420 |
| actgacgcta tcttgtccag agctggagga tccattgctg acttcaccgg tcacagacag | 480 |
| actgccttca gagagttgga aagagttctt aacttcccac aatcaaactt gtgcttgaag | 540 |
| cgtgagaagc aagacgaatc ctgttccttg actcaagcat taccatgtga gttgaaggtc | 600 |

```
tccgccgaca acgtctcttt gaccggtgct tgtagcttgg cttccatgtt gactgaaatc    660
tttcttctgc aacaagctca aggtatgcct gagccaggtt ggggtagaat caccgactct    720
caccaatgga acaccttgtt gtccttgcac aacgctcaat tctacttgct gcagagaact    780
ccagaggttg ctagatccag agccacccca ttgttggact tgatcaagac tgctttgact    840
cctcacccac ctcaaaagca agcctacggt gttaccttgc ccacttctgt cttgttcatt    900
gccggtcacg atactaactt ggcaaatctc ggcggtgctt tggagttgaa ctggactctt    960
cctggtcaac ctgataacac tccaccaggt ggtgagctcg ttttcgaaag atggcgtaga   1020
ctatctgata actctcaatg gattcaggtt tcgttggtct tccaaacttt gcagcagatg   1080
agagacaaga ctccactgtc tttgaacacg cctccaggag aagtcaaatt gaccttggct   1140
ggatgtgaag agagaaatgc tcagggtatg tgttccttgg ctggtttcac tcaaatcgtt   1200
aacgaagcta gaatcccagc ttgttccttg tag                                1233
```

<210> SEQ ID NO 52
<211> LENGTH: 1233
<212> TYPE: DNA
<213> ORGANISM: Artificial Sequence
<220> FEATURE:
<223> OTHER INFORMATION: APPA-L

<400> SEQUENCE: 52

```
cagagtgagc ctgagttgaa actggaatcc gttgtcatcg tctctagaca tggtgttaga     60
gcaccaacca aggccaccca acttatgcaa gatgtcaccc cagacgcttg gccaacctgg    120
ccagtcaagc tgggttggtt gacacctaga ggtggtgagc tcattgctta cttgggtcac    180
taccaaagac agcgtcttgt tgccgacgga ttgttggcca agaagggttg tccacaatct    240
ggtcaagtag ctattattgc tgacgtcgac gaaagaaccc gtaagacagg tgaagccttc    300
gccgccggtc ttgctcctga ctgtgccatt accgttcaca cccaagctga cacttcttct    360
ccagatccat tgttcaaccc tttgaagact ggtgtttgcc aattggacaa cgctaacgtt    420
actgacgcta tcttgtccag agctggagga tccattgctg acttcaccgg tcacagacag    480
actgccttca gagagttgga aagagttctt aacttcccac aatcaaactt gtgcttgaag    540
cgtgagaagc aagacgaatc ctgttccttg actcaagcat taccatctga gttgaaggtc    600
tccgccgaca acgtctcttt gaccggtgct gtcagcttgg cttccatgtt gactgaaatc    660
tttcttctgc aacaagctca aggtatgcct gagccaggtt ggggtagaat caccgactct    720
caccaatgga acaccttgtt gtccttgcac aacgctcaat tctacttgct gcagagaact    780
ccagaggttt gtagatccag agccacccca ttgttggact tgatcaagac tgctttgact    840
cctcacccac ctcaaaagca agcctacggt gttaccttgc ccacttctgt cttgttcatt    900
gccggtcacg atactaactt ggcaaatctc ggctgtgctt tggagttgaa ctggactctt    960
cctggtcaac ctgataacac tccaccaggt ggtgagctcg ttttcgaaag atggcgtaga   1020
ctatctgata actctcaatg gattcaggtt tcgttggtct tccaaacttt gcagcagatg   1080
agagacaaga ctccactgtc tttgaacacg cctccaggag aagtcaaatt gaccttggct   1140
ggatgtgaag agagaaatgc tcagggtatg tgttccttgg ctggtttcac tcaaatcgtt   1200
aacgaagcta gaatcccagc ttgttccttg tag                                1233
```

<210> SEQ ID NO 53
<211> LENGTH: 1233
<212> TYPE: DNA

<213> ORGANISM: Artificial Sequence
<220> FEATURE:
<223> OTHER INFORMATION: APPA-M

<400> SEQUENCE: 53

```
cagagtgagc ctgagttgaa actggaatcc gttgtcatcg tctctagaca tggtgttaga      60
gcaccaacca aggccaccca acttatgcaa gatgtcaccc cagacgcttg gccaacctgg     120
ccagtcaagc tgggttggtt gacacctaga ggtggtgagc tcattgctta cttgggtcac     180
taccaaagac agcgtcttgt tgccgacgga ttgttggcca agaagggttg tccacaatct     240
ggtcaagtag ctattattgc tgacgtcgac gaaagaaccc gtaagacagg tgaagccttc     300
gccgccggtc ttgctcctga ctgtgccatt accgttcaca cccaagctga cacttcttct     360
ccagatccat tgttcaaccc tttgaagact ggtgtttgcc aattggacaa cgctaacgtt     420
actgacgcta tcttgtccag agctggagga tccattgctg acttcaccgg tcacagacag     480
actgccttca gagagttgga aagagttctt aacttcccac aatcaaactt gtgcttgaag     540
cgtgagaagc aagacgaatc ctgttccttg actcaagcat taccatctga gttgaaggtc     600
tccgccgaca acgtctcttt gaccggtgct gtcagcttgg cttccatgtt gactgaaatc     660
tttcttctgc aacaagctca aggtatgcct gagccaggtt ggggtagaat caccgactct     720
caccaatgga acaccttgtt gtccttgcac aacgctcaat tctacttgct gcagagaact     780
ccagaggttg ctagatccag agccacccca ttgttggact tgatcaagac tgctttgact     840
cctcacccac ctcaaaagca agcctacggt gttaccttgc ccacttctgt cttgttcatt     900
gccggtcacg atactaactt ggcaaatctc ggcggtgctt tgtgtttgaa ctggactctt     960
cctggtcaac ctgataacac tccaccaggt ggtgagctcg ttttcgaaag atggcgtaga    1020
ctatctgata ctctcaatg gattcaggtt tcgttggtct tccaaacttt gcagcagatg    1080
agagacaaga ctccactgtc tttgaacacg cctccaggag aagtcaaatt gaccttgtgt    1140
ggatgtgaag agagaaatgc tcagggtatg tgttccttgg ctggtttcac tcaaatcgtt    1200
aacgaagcta gaatcccagc ttgttccttg tag                                 1233
```

<210> SEQ ID NO 54
<211> LENGTH: 1233
<212> TYPE: DNA
<213> ORGANISM: Artificial Sequence
<220> FEATURE:
<223> OTHER INFORMATION: APPA-N

<400> SEQUENCE: 54

```
cagagtgagc ctgagttgaa actggaatcc gttgtcatcg tctctagaca tggtgttaga      60
gcaccaacca aggccaccca acttatgcaa gatgtcaccc cagacgcttg gccaacctgg     120
ccagtcaagc tgggttggtt gacacctaga ggtggtgagc tcattgctta cttgggtcac     180
taccaaagac agcgtcttgt tgccgacgga ttgttggcca agaagggttg tccacaatct     240
ggtcaagtag ctattattgc tgacgtcgac gaaagaaccc gtaagacagg tgaagccttc     300
gccgccggtc ttgctcctga ctgtgccatt accgttcaca cccaagctga cacttcttct     360
ccagatccat tgttcaaccc tttgaagact ggtgtttgcc aattggacaa cgctaacgtt     420
actgacgcta tcttgtccag agctggagga tccattgctg acttcaccgg tcacagacag     480
actgccttca gagagttgga aagagttctt aacttcccac aatcaaactt gtgcttgaag     540
cgtgagaagc aagacgaatc ctgttccttg actcaagcat taccatctga gttgaaggtc     600
tccgccgaca acgtctcttt gaccggtgct gtcagcttgg cttccatgtt gactgaaatc     660
```

```
tttcttctgc aacaagctca aggtatgcct gagccaggtt ggggtagaat caccgactct    720
caccaatgga acaccttgtt gtccttgcac aacgctcaat tctacttgct gcagagaact    780
ccagaggttg ctagatccag agccacccca ttgttggact tgatcaagac tgctttgact    840
cctcacccac ctcaaaagca agcctacggt gttaccttgc ccacttctgt cttgttcatt    900
gccggtcacg atactaactt ggcaaatctc ggcggtgctt tggagttgaa ctggactctt    960
ccttgtcaac ctgataacac tccaccaggt ggtgagctcg ttttcgaaag atggcgtaga   1020
ctatctgata actctcaatg gattcaggtt tcgttggtct tccaatgttt gcagcagatg   1080
agagacaaga ctccactgtc tttgaacacg cctccaggag aagtcaaatt gaccttggct   1140
ggatgtgaag agagaaatgc tcagggtatg tgttccttgg ctggtttcac tcaaatcgtt   1200
aacgaagcta gaatcccagc ttgttccttg tag                                1233
```

<210> SEQ ID NO 55
<211> LENGTH: 1233
<212> TYPE: DNA
<213> ORGANISM: Artificial Sequence
<220> FEATURE:
<223> OTHER INFORMATION: APPA-O

<400> SEQUENCE: 55

```
cagagtgagc ctgagttgaa actggaatcc gttgtcatcg tctctagaca tggtgttaga     60
gcaccaacca aggccaccca acttatgcaa gatgtcaccc cagacgcttg gccaacctgg    120
ccagtcaagc tgggttggtt gacacctaga ggtggtgagc tcattgctta cttgggtcac    180
taccaaagac agcgtcttgt tgccgacgga ttgttggcca agaagggttg tccacaatct    240
ggtcaagtag ctattattgc tgacgtcgac gaaagaaccc gtaagacagg tgaagccttc    300
gccgccggtc ttgctcctga ctgtgccatt accgttcaca cccaagctga cacttcttct    360
ccagatccat tgttcaaccc tttgaagact ggtgtttgcc aattggacaa cgctaacgtt    420
actgacgcta tcttgtccag agctggagga tccattgctg acttcaccgg tcacagacag    480
actgccttca gagagttgga aagagttctt aacttcccac aatcaaactt gtgcttgaag    540
cgtgagaagc aagacgaatc ctgttccttg actcaagcat taccatctga gttgaaggtc    600
tccgccgaca acgtctcttt gaccggtgct gtcagcttgg cttccatgtt gactgaaatc    660
tttcttctgc aacaagctca aggtatgcct gagccaggtt ggggtagaat caccgactct    720
caccaatgga acaccttgtt gtccttgcac aacgctcaat tctacttgct gcagagaact    780
ccagaggttg ctagatccag agccacccca ttgttggact tgatcaagac tgctttgact    840
cctcacccac ctcaaaagca agcctacggt gttaccttgc ccacttctgt cttgttcatt    900
gccggtcacg atactaactt ggcaaatctc ggcggtgctt tggagttgaa ctggactctt    960
cctggtcaac ctgataacac tccaccaggt ggtgagctcg ttttcgaaag atggcgtaga   1020
ctatctgata actcttgttg gattcaggtt tcgttggtct tccaaacttt gcagcagatg   1080
agagacaaga ctccactgtc tttgaacacg cctccaggag aagtcaaatt gaccttggct   1140
ggatgtgaag agagaaatgc tcagggtatg tgttcctgtg ctggtttcac tcaaatcgtt   1200
aacgaagcta gaatcccagc ttgttccttg tag                                1233
```

<210> SEQ ID NO 56
<211> LENGTH: 1233
<212> TYPE: DNA
<213> ORGANISM: Artificial Sequence
<220> FEATURE:

<223> OTHER INFORMATION: APPA-P

<400> SEQUENCE: 56

```
cagagtgagc ctgagttgaa actggaatcc gttgtcatcg tctctagaca tggtgttaga      60
gcaccaacca aggccaccca acttatgcaa gatgtcaccc cagacgcttg gccaacctgg     120
ccagtcaagc tgggttggtt gacacctaga ggtggtgagc tcattgctta cttgggtcac     180
taccaaagac agcgtcttgt tgccgacgga ttgttggcca agaagggttg tccacaatct     240
ggtcaagtag ctattattgc tgacgtcgac gaaagaaccc gtaagacagg tgaagccttc     300
gccgccggtc ttgctcctga ctgtgccatt accgttcaca cccaagctga cacttcttct     360
ccagatccat tgttcaaccc tttgaagact ggtgtttgcc aattggacaa cgctaacgtt     420
actgacgcta tcttgtccag agctggagga tccattgctg acttcaccgg tcacagacag     480
actgccttca gagagttgga aagagttctt aacttcccac aatcaaactt gtgcttgaag     540
cgtgagaagc aagacgaatc ctgttccttg actcaagcat taccatctga gttgaaggtc     600
tccgccgaca acgtctcttt gaccggtgct gtcagcttgg cttccatgtt gactgaaatc     660
tttcttctgc aacaagctca aggtatgcct gagccaggtt ggggtagaat caccgactct     720
caccaatgga acaccttgtt gtccttgcac aacgctcaat tctacttgct gcagagaact     780
ccagaggttg ctagatccag agccaccccca ttgttggact tgatcaagac tgctttgact     840
cctcacccac ctcaaaagca agcctacggt gttaccttgc ccacttctgt cttgttcatt     900
gccggtcacg atactaactt ggcaaatctc ggcggtgctt tggagttgaa ctggactctt     960
cctggtcaac ctgataacac tccaccaggt ggtgagctcg ttttcgaaag atggcgtaga    1020
ctatctgata actctcaatg gatttgtgtt tcgttggtct tccaaacttt gcagcagatg    1080
agagacaaga ctccactgtc tttgaacacg cctccaggag aagtcaaatt gaccttggct    1140
ggatgtgaag agagaaatgc tcagggttgt tgttccttgg ctggtttcac tcaaatcgtt    1200
aacgaagcta gaatcccagc ttgttccttg tag                                 1233
```

<210> SEQ ID NO 57
<211> LENGTH: 1233
<212> TYPE: DNA
<213> ORGANISM: Artificial Sequence
<220> FEATURE:
<223> OTHER INFORMATION: APPA-M1-D

<400> SEQUENCE: 57

```
cagagtgagc ctgagttgaa actggaatcc gttgtcatcg tctctagaca tggtgttaga      60
gcaccaacca agttcaccca acttatgcaa gatgtcaccc cagacgcttg gccaacctgg     120
ccagtcaagc tgggtgaatt gacacctaga ggtggtgagc tcattgctta cttgggtcac     180
tgttggagac agcgtcttgt tgccgacgaa ttgttgccta agtgtggttg tccacaatct     240
ggtcaagtag ctattattgc tgacgtcgac gaaagaaccc gtaagacagg tgaagccttc     300
gccgccggtc ttgctcctga ctgtgccatt accgttcacc atcaagctga cacttcttct     360
ccagatccat tgttcaaccc tttgaagact ggtgtttgcc aattggacgt tgctaacgtt     420
actagagcta tcttggaaag agctggagga tctattgctg acttcaccgg tcactaccag     480
actgccttca gagagttgga aagagttctt aacttcccac aatccaactt gtgccttaag     540
cgtgagaagc aagacgaatc ctgttccttg actcaagcat taccatctga gttgaaggtc     600
tccgccgaca acgtctcttt gaccggtgct gtcagcttgg cttccatgtt gactgaaatc     660
tttcttctgc aacaagctca aggtatgcct gagccaggtt ggggtagaat caccgactct     720
```

| | |
|---|---|
| caccaatgga acaccttgtt gtccttgcac aacgctcaat tcgatttgct gcagagaact | 780 |
| ccagaggttg ctagatccag agccacccca ttgttggact tgatcaagac tgctttgact | 840 |
| cctcacccac ctcaaaagca agcctacggt gttaccttgc ccacttctgt cttgttcatt | 900 |
| gccggtcacg atactaactt ggcaaatctc ggcggtgctt tggagttgaa ctggactctt | 960 |
| cctggtcaac ctgataacac tccaccaggt ggtgagctcg ttttcgaaag atggcgtaga | 1020 |
| ctatctgata actctcaatg gattcaggtt tcgttggtct tccaaacttt gcagcagatg | 1080 |
| agagacaaga ctccatgttc tttgaacacg cctccaggag aagtcaaatt gaccttggct | 1140 |
| ggatgtgaag agagaaatgc tcagggtatg tgttccttgg ctggtttcac tcaaatcgtt | 1200 |
| aacgaagcta gaatcccagc ttgttccttg tag | 1233 |

<210> SEQ ID NO 58
<211> LENGTH: 1233
<212> TYPE: DNA
<213> ORGANISM: Artificial Sequence
<220> FEATURE:
<223> OTHER INFORMATION: APPA-M1-O

<400> SEQUENCE: 58

| | |
|---|---|
| cagagtgagc ctgagttgaa actggaatcc gttgtcatcg tctctagaca tggtgttaga | 60 |
| gcaccaacca agttcaccca acttatgcaa gatgtcaccc cagacgcttg gccaacctgg | 120 |
| ccagtcaagc tgggtgaatt gacacctaga ggtggtgagc tcattgctta cttgggtcac | 180 |
| tactggagac agcgtcttgt tgccgacgaa ttgttgccta agtgtggttg tccacaatct | 240 |
| ggtcaagtag ctattattgc tgacgtcgac gaaagaaccc gtaagacagg tgaagccttc | 300 |
| gccgccggtc ttgctcctga ctgtgccatt accgttcacc atcaagctga cacttcttct | 360 |
| ccagatccat tgttcaaccc tttgaagact ggtgtttgcc aattggacgt tgctaacgtt | 420 |
| actagagcta tcttggaaag agctggagga tctattgctg acttcaccgg tcactaccag | 480 |
| actgccttca gagagttgga aagagttctt aacttcccac aatccaactt gtgccttaag | 540 |
| cgtgagaagc aagacgaatc ctgttccttg actcaagcat taccatctga gttgaaggtc | 600 |
| tccgccgaca acgtctcttt gaccggtgct gtcagcttgg cttccatgtt gactgaaatc | 660 |
| tttcttctgc aacaagctca aggtatgcct gagccaggtt ggggtagaat caccgactct | 720 |
| caccaatgga acaccttgtt gtccttgcac aacgctcaat tcgatttgct gcagagaact | 780 |
| ccagaggttg ctagatccag agccacccca ttgttggact tgatcaagac tgctttgact | 840 |
| cctcacccac ctcaaaagca agcctacggt gttaccttgc ccacttctgt cttgttcatt | 900 |
| gccggtcacg atactaactt ggcaaatctc ggcggtgctt tggagttgaa ctggactctt | 960 |
| cctggtcaac ctgataacac tccaccaggt ggtgagctcg ttttcgaaag atggcgtaga | 1020 |
| ctatctgata actcttgttg gattcaggtt tcgttggtct tccaaacttt gcagcagatg | 1080 |
| agagacaaga ctccactgtc tttgaacacg cctccaggag aagtcaaatt gaccttggct | 1140 |
| ggatgtgaag agagaaatgc tcagggtatg tgttcctgtg ctggtttcac tcaaatcgtt | 1200 |
| aacgaagcta gaatcccagc ttgttccttg tag | 1233 |

<210> SEQ ID NO 59
<211> LENGTH: 1233
<212> TYPE: DNA
<213> ORGANISM: Artificial Sequence
<220> FEATURE:
<223> OTHER INFORMATION: APPA-M1-BO

<400> SEQUENCE: 59

```
cagagtgagc ctgagttgaa actggaatcc gttgtcatcg tctctagaca tggtgttaga      60
gcaccaacca agttcaccca acttatgcaa gatgtcaccc cagacgcttg gccaacctgg     120
ccagtcaagc tgggtgaatt gacacctaga ggtggtgagc tcatttgtta cttgggtcac     180
tactggagac agcgtcttgt tgccgacgaa ttgttgccta agtgtggttg tccacaatct     240
ggtcaagtag ctattattgc tgacgtcgac gaaagaaccc gtaagacagg tgaagccttc     300
gccgcctgtc ttgctcctga ctgtgccatt accgttcacc atcaagctga cacttcttct     360
ccagatccat tgttcaaccc tttgaagact ggtgtttgcc aattggacgt tgctaacgtt     420
actagagcta tcttggaaag agctggagga tctattgctg acttcaccgg tcactaccag     480
actgccttca gagagttgga aagagttctt aacttcccac aatccaactt gtgccttaag     540
cgtgagaagc aagacgaatc ctgttccttg actcaagcat taccatctga gttgaaggtc     600
tccgccgaca acgtctcttt gaccggtgct gtcagcttgg cttccatgtt gactgaaatc     660
tttcttctgc aacaagctca aggtatgcct gagccaggtt ggggtagaat caccgactct     720
caccaatgga acaccttgtt gtccttgcac aacgctcaat tcgatttgct gcagagaact     780
ccagaggttg ctagatccag agccaccccca ttgttggact tgatcaagac tgctttgact     840
cctcacccac ctcaaaagca agcctacggt gttaccttgc ccacttctgt cttgttcatt     900
gccggtcacg atactaactt ggcaaatctc ggcggtgctt tggagttgaa ctggactctt     960
cctggtcaac ctgataacac tccaccaggt ggtgagctcg ttttcgaaag atggcgtaga    1020
ctatctgata ctcttgttg gattcaggtt tcgttggtct tccaaacttt gcagcagatg    1080
agagacaaga ctccactgtc tttgaacacg cctccaggag aagtcaaatt gaccttggct    1140
ggatgtgaag agagaaatgc tcagggtatg tgttcctgtg ctggtttcac tcaaatcgtt    1200
aacgaagcta gaatcccagc ttgttccttg tag                                 1233
```

<210> SEQ ID NO 60
<211> LENGTH: 1233
<212> TYPE: DNA
<213> ORGANISM: Artificial Sequence
<220> FEATURE:
<223> OTHER INFORMATION: APPA-M1-CO

<400> SEQUENCE: 60

```
cagagtgagc ctgagttgaa actggaatcc gttgtcatcg tctctagaca tggtgttaga      60
gcaccaacca agttcaccca acttatgcaa gatgtcaccc cagacgcttg gccaacctgg     120
ccagtcaagc tgggtgaatt gacacctaga ggtggtgagc tcattgcttg tttgggtcac     180
tactggagac agcgtcttgt tgccgacgaa ttgttgccta agtgtggttg tccacaatct     240
ggtcaagtag ctattattgc tgacgtcgac gaaagaaccc gtaagacagg tgaagccttc     300
gccgccggtc ttgctcctga ctgtgccatt accgttcacc atcaagctga cacttcttct     360
ccagatccat tgttcaaccc tttgaagact ggtgtttgcc aattggacgt tgctaacgtt     420
actagagcta tcttggaaag agctggagga tctattgctg acttcaccgg tcactaccag     480
actgccttca gagagttgga aagagttctt aacttcccac aatccaactt gtgccttaag     540
cgtgagaagc aagacgaatc ctgttccttg actcaagcat taccatctga gttgaaggtc     600
tccgccgaca acgtctcttt gaccggtgct gtcagcttgg cttccatgtt gactgaaatc     660
tttcttctgc aacaagctca aggtatgcct gagccaggtt ggggtagaat caccgactct     720
caccaatgga acaccttgtt gtccttgcac aacgctcaat tcgatttgct gcagagaact     780
```

```
ccagaggttg ctagatccag agccacccca ttgttggact tgatcaagac tgctttgact     840
cctcacccac ctcaaaagca agcctacggt gttaccttgc ccacttctgt cttgttcatt     900
gccggtcacg atactaactt ggcaaatctc ggcggtgctt tggagttgaa ctggactctt     960
cctggtcaac ctgataacac tccaccaggt ggtgagctcg ttttcgaaag atggcgtaga    1020
ctatctgata actcttgttg gattcaggtt tcgttggtct tccaaacttt gcagcagatg    1080
agagacaaga ctccatgttc tttgaacacg cctccaggag aagtcaaatt gaccttggct    1140
ggatgtgaag agagaaatgc tcagggtatg tgttcctgtg ctggtttcac tcaaatcgtt    1200
aacgaagcta gaatcccagc ttgttccttg tag                                 1233
```

<210> SEQ ID NO 61
<211> LENGTH: 1233
<212> TYPE: DNA
<213> ORGANISM: Artificial Sequence
<220> FEATURE:
<223> OTHER INFORMATION: APPA-M1-DO

<400> SEQUENCE: 61

```
cagagtgagc ctgagttgaa actggaatcc gttgtcatcg tctctagaca tggtgttaga      60
gcaccaacca agttcaccca acttatgcaa gatgtcaccc cagacgcttg gccaacctgg     120
ccagtcaagc tgggtgaatt gacacctaga ggtggtgagc tcattgctta cttgggtcac     180
tgttggagac agcgtcttgt tgccgacgaa ttgttgccta agtgtggttg tccacaatct     240
ggtcaagtag ctattattgc tgacgtcgac gaaagaaccc gtaagacagg tgaagccttc     300
gccgccggtc ttgctcctga ctgtgccatt accgttcacc atcaagctga cacttcttct     360
ccagatccat tgttcaaccc tttgaagact ggtgtttgcc aattggacgt tgctaacgtt     420
actagagcta tcttggaaag agctggagga tctattgctg acttcaccgg tcactaccag     480
actgccttca gagagttgga aagagttctt aacttcccac aatccaactt gtgccttaag     540
cgtgagaagc aagacgaatc ctgttccttg actcaagcat taccatctga gttgaaggtc     600
tccgccgaca acgtctcttt gaccggtgct gtcagcttgg cttccatgtt gactgaaatc     660
tttcttctgc aacaagctca aggtatgcct gagccaggtt ggggtagaat caccgactct     720
caccaatgga acaccttgtt gtccttgcac aacgctcaat tcgatttgct gcagagaact     780
ccagaggttg ctagatccag agccacccca ttgttggact tgatcaagac tgctttgact     840
cctcacccac ctcaaaagca agcctacggt gttaccttgc ccacttctgt cttgttcatt     900
gccggtcacg atactaactt ggcaaatctc ggcggtgctt tggagttgaa ctggactctt     960
cctggtcaac ctgataacac tccaccaggt ggtgagctcg ttttcgaaag atggcgtaga    1020
ctatctgata actcttgttg gattcaggtt tcgttggtct tccaaacttt gcagcagatg    1080
agagacaaga ctccatgttc tttgaacacg cctccaggag aagtcaaatt gaccttggct    1140
ggatgtgaag agagaaatgc tcagggtatg tgttcctgtg ctggtttcac tcaaatcgtt    1200
aacgaagcta gaatcccagc ttgttccttg tag                                 1233
```

<210> SEQ ID NO 62
<211> LENGTH: 1233
<212> TYPE: DNA
<213> ORGANISM: Artificial Sequence
<220> FEATURE:
<223> OTHER INFORMATION: APPA-M1-MO

<400> SEQUENCE: 62

```
cagagtgagc ctgagttgaa actggaatcc gttgtcatcg tctctagaca tggtgttaga      60
gcaccaacca agttcaccca acttatgcaa gatgtcaccc cagacgcttg gccaacctgg     120
ccagtcaagc tgggtgaatt gacacctaga ggtggtgagc tcattgctta cttgggtcac     180
tactggagac agcgtcttgt tgccgacgaa ttgttgccta agtgtggttg tccacaatct     240
ggtcaagtag ctattattgc tgacgtcgac gaaagaaccc gtaagacagg tgaagccttc     300
gccgccggtc ttgctcctga ctgtgccatt accgttcacc atcaagctga cacttcttct     360
ccagatccat tgttcaaccc tttgaagact ggtgtttgcc aattggacgt tgctaacgtt     420
actagagcta tcttggaaag agctggagga tctattgctg acttcaccgg tcactaccag     480
actgccttca gagagttgga aagagttctt aacttcccac aatccaactt gtgccttaag     540
cgtgagaagc aagacgaatc ctgttccttg actcaagcat accatctga gttgaaggtc      600
tccgccgaca acgtctcttt gaccggtgct gtcagcttgg cttccatgtt gactgaaatc     660
tttcttctgc aacaagctca aggtatgcct gagccaggtt ggggtagaat caccgactct     720
caccaatgga acaccttgtt gtccttgcac aacgctcaat tcgatttgct gcagagaact     780
ccagaggttg ctagatccag agccacccca ttgttggact tgatcaagac tgctttgact     840
cctcaccac ctcaaaagca agcctacggt gttaccttgc ccacttctgt cttgttcatt      900
gccggtcacg atactaactt ggcaaatctc ggcggtgctt tgtgtttgaa ctggactctt     960
cctggtcaac ctgataacac tccaccaggt ggtgagctcg ttttcgaaag atggcgtaga    1020
ctatctgata actcttgttg gattcaggtt tcgttggtct tccaaacttt gcagcagatg    1080
agagacaaga ctccactgtc tttgaacacg cctccaggag aagtcaaatt gaccttgtgt    1140
ggatgtgaag agagaaatgc tcagggtatg tgttcctgtg ctggtttcac tcaaatcgtt    1200
aacgaagcta gaatcccagc ttgttccttg tag                                 1233

<210> SEQ ID NO 63
<211> LENGTH: 1233
<212> TYPE: DNA
<213> ORGANISM: Artificial Sequence
<220> FEATURE:
<223> OTHER INFORMATION: APPA-M1-BDO

<400> SEQUENCE: 63
cagagtgagc ctgagttgaa actggaatcc gttgtcatcg tctctagaca tggtgttaga      60
gcaccaacca agttcaccca acttatgcaa gatgtcaccc cagacgcttg gccaacctgg     120
ccagtcaagc tgggtgaatt gacacctaga ggtggtgagc tcatttgtta cttgggtcac     180
tgttggagac agcgtcttgt tgccgacgaa ttgttgccta agtgtggttg tccacaatct     240
ggtcaagtag ctattattgc tgacgtcgac gaaagaaccc gtaagacagg tgaagccttc     300
gccgcctgtc ttgctcctga ctgtgccatt accgttcacc atcaagctga cacttcttct     360
ccagatccat tgttcaaccc tttgaagact ggtgtttgcc aattggacgt tgctaacgtt     420
actagagcta tcttggaaag agctggagga tctattgctg acttcaccgg tcactaccag     480
actgccttca gagagttgga aagagttctt aacttcccac aatccaactt gtgccttaag     540
cgtgagaagc aagacgaatc ctgttccttg actcaagcat accatctga gttgaaggtc      600
tccgccgaca acgtctcttt gaccggtgct gtcagcttgg cttccatgtt gactgaaatc     660
tttcttctgc aacaagctca aggtatgcct gagccaggtt ggggtagaat caccgactct     720
caccaatgga acaccttgtt gtccttgcac aacgctcaat tcgatttgct gcagagaact     780
ccagaggttg ctagatccag agccacccca ttgttggact tgatcaagac tgctttgact     840
```

```
cctcacccac tcaaaagca agcctacggt gttaccttgc ccacttctgt cttgttcatt    900
gccggtcacg atactaactt ggcaaatctc ggcggtgctt tggagttgaa ctggactctt    960
cctggtcaac ctgataacac tccaccaggt ggtgagctcg ttttcgaaag atggcgtaga   1020
ctatctgata actcttgttg gattcaggtt tcgttggtct tccaaacttt gcagcagatg   1080
agagacaaga ctccatgttc tttgaacacg cctccaggag aagtcaaatt gaccttggct   1140
ggatgtgaag agagaaatgc tcagggtatg tgttcctgtg ctggtttcac tcaaatcgtt   1200
aacgaagcta gaatcccagc ttgttccttg tag                                1233
```

<210> SEQ ID NO 64
<211> LENGTH: 1233
<212> TYPE: DNA
<213> ORGANISM: Artificial Sequence
<220> FEATURE:
<223> OTHER INFORMATION: APPA-M1-DMO

<400> SEQUENCE: 64

```
cagagtgagc ctgagttgaa actggaatcc gttgtcatcg tctctagaca tggtgttaga     60
gcaccaacca agttcaccca acttatgcaa gatgtcaccc cagacgcttg gccaacctgg    120
ccagtcaagc tgggtgaatt gacacctaga ggtggtgagc tcattgctta cttgggtcac    180
tgttggagac agcgtcttgt tgccgacgaa ttgttgccta agtgtggttg tccacaatct    240
ggtcaagtag ctattattgc tgacgtcgac gaaagaaccc gtaagacagg tgaagccttc    300
gccgccggtc ttgctcctga ctgtgccatt accgttcacc atcaagctga cacttcttct    360
ccagatccat tgttcaaccc tttgaagact ggtgtttgcc aattggacgt tgctaacgtt    420
actagagcta tcttggaaag agctggagga tctattgctg acttcaccgg tcactaccag    480
actgccttca gagagttgga aagagttctt aacttcccac aatccaactt gtgccttaag    540
cgtgagaagc aagacgaatc ctgttccttg actcaagcat taccatctga ttgaaggtc     600 tccgccgaca acgtctcttt gaccggtgct gtcagcttgg cttccatgtt gactgaaatc    660
tttcttctgc aacaagctca aggtatgcct gagccaggtt ggggtagaat caccgactct    720
caccaatgga acaccttgtt gtccttgcac aacgctcaat tcgatttgct gcagagaact    780
ccagaggttg ctagatccag agccacccca ttgttggact tgatcaagac tgctttgact    840
cctcacccac tcaaaagca agcctacggt gttaccttgc ccacttctgt cttgttcatt     900
gccggtcacg atactaactt ggcaaatctc ggcggtgctt tgtgtttgaa ctggactctt    960
cctggtcaac ctgataacac tccaccaggt ggtgagctcg ttttcgaaag atggcgtaga   1020
ctatctgata actcttgttg gattcaggtt tcgttggtct tccaaacttt gcagcagatg   1080
agagacaaga ctccatgttc tttgaacacg cctccaggag aagtcaaatt gaccttgtgt   1140
ggatgtgaag agagaaatgc tcagggtatg tgttcctgtg ctggtttcac tcaaatcgtt   1200
aacgaagcta gaatcccagc ttgttccttg tag                                1233
```

<210> SEQ ID NO 65
<211> LENGTH: 1233
<212> TYPE: DNA
<213> ORGANISM: Artificial Sequence
<220> FEATURE:
<223> OTHER INFORMATION: APPAan-A

<400> SEQUENCE: 65

```
cagtccgagc ccgagctcaa gctcgagtcc gtcgtcatcg tctcccgcca cggtgtccgc     60
```

```
gcccccacca aggccaccca gctcatgcag gacgtcacct gcgacgcctg gcccacctgg    120
cccgtcaagc tcggttggct cacccccgc ggtggtgagc tcatcgccta cctcggtcac     180
taccagcgcc agcgcctcgt cgccgacggt ctcctcgcca agaagggttg ccccccagtcc    240 ggtcaggtcg ccatcatcgc cgacgtcgac gagcgcaccc gcaagaccgg tgaggccttc    300
gccgccggtc tcgccccga ctgcgccatc accgtccaca cccaggccga cacctcctcc     360 cccgacccc tcttcaaccc cctcaagacc ggtgtctgcc agctcgacaa cgccaacgtc    420
accgacgcca tcctctcccg cgccggtggt tccatcgccg acttcaccgg tcaccgccag    480
accgccttcc gcgagctcga gcgcgtcctc aacttcccct gctccaacct ctgcctcaag    540
cgcgagaagc aggacgagtc ctgctccctc acccaggccc tcccctccga gctcaaggtc    600
tccgccgaca acgtctccct caccggtgcc gtctccctcg cctccatgct caccgagatc    660
ttcctcctcc agcaggccca gggtatgccc gagcccggtt ggggtcgcat caccgactcc    720
caccagtgga acaccctcct ctcccctcac aacgcccagt tctacctcct ccagcgcacc    780
cccgaggtcg cccgctcccg cgccacccc ctcctcgacc tcatcaagac cgccctcacc    840 ccccacccc ccagaagca ggcctacggt gtcaccctcc ccacctccgt cctcttcatc     900
gccggtcacg acaccaacct cgccaacctc ggtggtgccc tcgagctcaa ctggacccctc   960 cccggtcagc cgacaacac ccccccggt ggtgagctcg tcttcgagcg ctggcgccgc    1020
ctctccgaca actcccagtg gatccaggtc tccctcgtct tccagaccct ccagcagatg   1080
cgcgacaaga ccccctctc cctcaacacc ccccccggtg aggtcaagct caccctcgcc    1140
ggttgcgagg agcgcaacgc ccagggtatg tgctcccctcg ccggttttcac ccagatcgtc   1200 aacgaggccc gcatccccgc ctgctccctc taa                                 1233
```

<210> SEQ ID NO 66
<211> LENGTH: 1233
<212> TYPE: DNA
<213> ORGANISM: Artificial Sequence
<220> FEATURE:
<223> OTHER INFORMATION: APPAan-B

<400> SEQUENCE: 66

```
cagtccgagc ccgagctcaa gctcgagtcc gtcgtcatcg tctcccgcca cggtgtccgc     60
gcccccacca aggccaccca gctcatgcag gacgtcaccc ccgacgcctg gcccacctgg    120
cccgtcaagc tcggttggct cacccccgc ggtggtgagc tcatctgcta cctcggtcac    180
taccagcgcc agcgcctcgt cgccgacggt ctcctcgcca agaagggttg ccccccagtcc    240 ggtcaggtcg ccatcatcgc cgacgtcgac gagcgcaccc gcaagaccgg tgaggccttc    300
gccgcctgcc tcgccccga ctgcgccatc accgtccaca cccaggccga cacctcctcc     360 cccgacccc tcttcaaccc cctcaagacc ggtgtctgcc agctcgacaa cgccaacgtc    420
accgacgcca tcctctcccg cgccggtggt tccatcgccg acttcaccgg tcaccgccag    480
accgccttcc gcgagctcga gcgcgtcctc aacttccccc agtccaacct ctgcctcaag    540
cgcgagaagc aggacgagtc ctgctccctc acccaggccc tcccctccga gctcaaggtc    600
tccgccgaca acgtctccct caccggtgcc gtctccctcg cctccatgct caccgagatc    660
ttcctcctcc agcaggccca gggtatgccc gagcccggtt ggggtcgcat caccgactcc    720
caccagtgga acaccctcct ctcccctcac aacgcccagt tctacctcct ccagcgcacc    780
cccgaggtcg cccgctcccg cgccacccc ctcctcgacc tcatcaagac cgccctcacc    840 ccccacccc ccagaagca ggcctacggt gtcaccctcc ccacctccgt cctcttcatc     900
```

```
gccggtcacg acaccaacct cgccaacctc ggtggtgccc tcgagctcaa ctggaccctc    960
cccggtcagc ccgacaacac ccccccggt ggtgagctcg tcttcgagcg ctggcgccgc    1020
ctctccgaca actcccagtg gatccaggtc tccctcgtct tccagaccct ccagcagatg    1080
cgcgacaaga ccccctctc cctcaacacc ccccggtg aggtcaagct caccctcgcc    1140
ggttgcgagg agcgcaacgc ccagggtatg tgctccctcg ccggtttcac ccagatcgtc    1200
aacgaggccc gcatccccgc ctgctccctc taa                                 1233

<210> SEQ ID NO 67
<211> LENGTH: 1233
<212> TYPE: DNA
<213> ORGANISM: Artificial Sequence
<220> FEATURE:
<223> OTHER INFORMATION: APPAan-C

<400> SEQUENCE: 67
cagtccgagc ccgagctcaa gctcgagtcc gtcgtcatcg tctcccgcca cggtgtccgc     60
gcccccacca aggccaccca gctcatgcag gacgtcaccc ccgacgcctg gcccacctgg    120
cccgtcaagc tcggttggct caccccccgc ggtggtgagc tcatcgcctg cctcggtcac    180
taccagcgcc agcgcctcgt cgccgacggt ctcctcgcca agaagggttg cccccagtcc    240
ggtcaggtcg ccatcatcgc cgacgtcgac gagcgcaccc gcaagaccgg tgaggccttc    300
gccgccggtc tcgcccccga ctgcgccatc accgtccaca cccaggccga cacctcctcc    360
cccgaccccc tcttcaaccc cctcaagacc ggtgtctgcc agctcgacaa cgccaacgtc    420
accgacgcca tcctctcccg cgccggtggt tccatcgccg acttcaccgg tcaccgccag    480
accgccttcc gcgagctcga gcgcgtcctc aacttccccc agtccaacct ctgcctcaag    540
cgcgagaagc aggacgagtc ctgctccctc acccaggccc tccctccga gctcaaggtc    600 tccgccgaca acgtctccct caccggtgcc gtctccctcg cctccatgct caccgagatc    660
ttcctcctcc agcaggccca gggtatgccc gagcccggtt ggggtcgcat caccgactcc    720
caccagtgga acaccctcct ctccctccac aacgcccagt tctacctcct ccagcgcacc    780
cccgaggtcg cccgctcccg cgccaccccc ctcctcgacc tcatcaagac cgccctcacc    840 cccaccccc ccagaagca ggcctacggt gtcaccctcc ccacctccgt cctcttcatc    900
gccggtcacg acaccaacct cgccaacctc ggtggtgccc tcgagctcaa ctggaccctc    960
cccggtcagc ccgacaacac ccccccggt ggtgagctcg tcttcgagcg ctggcgccgc    1020
ctctccgaca actcccagtg gatccaggtc tccctcgtct tccagaccct ccagcagatg    1080
cgcgacaaga ccccctgctc cctcaacacc ccccggtg aggtcaagct caccctcgcc    1140
ggttgcgagg agcgcaacgc ccagggtatg tgctccctcg ccggtttcac ccagatcgtc    1200
aacgaggccc gcatccccgc ctgctccctc taa                                 1233

<210> SEQ ID NO 68
<211> LENGTH: 1233
<212> TYPE: DNA
<213> ORGANISM: Artificial Sequence
<220> FEATURE:
<223> OTHER INFORMATION: APPAan-D

<400> SEQUENCE: 68
cagtccgagc ccgagctcaa gctcgagtcc gtcgtcatcg tctcccgcca cggtgtccgc     60
gcccccacca aggccaccca gctcatgcag gacgtcaccc ccgacgcctg gcccacctgg    120
```

```
cccgtcaagc tcggttggct caccccccgc ggtggtgagc tcatcgccta cctcggtcac    180
tgccagcgcc agcgcctcgt cgccgacggt ctcctcgcca agaagggttg cccccagtcc    240
ggtcaggtcg ccatcatcgc cgacgtcgac gagcgcaccc gcaagaccgg tgaggccttc    300
gccgccggtc tcgcccccga ctgcgccatc accgtccaca cccaggccga cacctcctcc    360
cccgacccce tcttcaaccc cctcaagacc ggtgtctgcc agctcgacaa cgccaacgtc    420
accgacgcca tcctctcccg cgccggtggt tccatcgccg acttcaccgg tcaccgccag    480
accgccttcc gcgagctcga gcgcgtcctc aacttccccc agtccaacct ctgcctcaag    540
cgcgagaagc aggacgagtc ctgctccctc acccaggccc tcccctccga gctcaaggtc    600
tccgccgaca acgtctccct caccggtgcc gtctccctcg cctccatgct caccgagatc    660
ttcctcctcc agcaggccca gggtatgccc gagcccggtt ggggtcgcat caccgactcc    720
caccagtgga cacccctcct ctccctccac aacgcccagt tctacctcct ccagcgcacc    780
cccgaggtcg cccgctcccg cgccaccccc ctcctcgacc tcatcaagac cgccctcacc    840
cccaccccc cccagaagca ggcctacggt gtcaccctcc ccacctccgt cctcttcatc    900
gccggtcacg acaccaacct cgccaacctc ggtggtgccc tcgagctcaa ctggaccctc    960
cccggtcagc ccgacaacac ccccccggt ggtgagctcg tcttcgagcg ctggcgccgc   1020
ctctccgaca actcccagtg gatccaggtc tccctcgtct tccagaccct ccagcagatg   1080
cgcgacaaga cccctgctc cctcaacacc ccccggtg aggtcaagct cacccctcgcc   1140
ggttgcgagg agcgcaacgc ccagggtatg tgctccctcg ccggtttcac ccagatcgtc   1200
aacgaggccc gcatccccgc ctgctccctc taa                                1233

<210> SEQ ID NO 69
<211> LENGTH: 1233
<212> TYPE: DNA
<213> ORGANISM: Artificial Sequence
<220> FEATURE:
<223> OTHER INFORMATION: APPAan-E

<400> SEQUENCE: 69
cagtccgagc ccgagctcaa gctcgagtcc gtcgtcatcg tctcccgcca cggtgtccgc     60
gccccccacca aggccaccca gctcatgcag gacgtcaccc ccgacgcctg gcccacctgg    120
cccgtcaagc tcggttggct caccccccgc ggtggtgagc tcatcgccta cctcggtcac    180
taccagcgcc agcgcctcgt cgccgacggt ctcctcgcca agaagggttg cccccagtcc    240
ggttgcgtcg ccatcatcgc cgacgtcgac gagcgcaccc gcaagaccgg tgaggccttc    300
gccgccggtc tcgcccccga ctgcgccatc accgtccaca cccaggccga cacctcctcc    360
cccgacccce tcttcaaccc cctcaagacc ggtgtctgcc agctcgacaa cgccaacgtc    420
accgacgcca tcctctcccg cgccggtggt tccatcgccg acttcaccgg tcaccgccag    480
accgccttcc gcgagctcga gcgcgtcctc aacttccccc agtccaacct ctgcctcaag    540
cgcgagaagc aggacgagtc ctgctccctc acccaggccc tcccctccga gctcaaggtc    600
tccgccgaca acgtctccct caccggtgcc gtctccctcg cctccatgct caccgagatc    660
ttcctcctcc agcaggccca gggtatgccc gagcccggtt ggggtcgcat caccgactcc    720
caccagtgga cacccctcct ctccctccac aacgcccagt tctacctcct ccagcgcacc    780
cccgaggtcg cccgctcccg cgccaccccc ctcctcgacc tcatcaagac cgccctcacc    840
cccacccccc cccagaagca ggcctacggt gtcaccctcc ccacctgcgt cctcttcatc    900
gccggtcacg acaccaacct cgccaacctc ggtggtgccc tcgagctcaa ctggaccctc    960
```

```
cccggtcagc cgacaacac cccccggt ggtgagctcg tcttcgagcg ctggcgccgc    1020
ctctccgaca actcccagtg gatccaggtc tccctcgtct tccagaccct ccagcagatg    1080
cgcgacaaga ccccctctc cctcaacacc cccccggtg aggtcaagct caccctcgcc    1140
ggttgcgagg agcgcaacgc ccagggtatg tgctccctcg ccggtttcac ccagatcgtc    1200
aacgaggccc gcatccccgc ctgctccctc taa                                1233

<210> SEQ ID NO 70
<211> LENGTH: 1233
<212> TYPE: DNA
<213> ORGANISM: Artificial Sequence
<220> FEATURE:
<223> OTHER INFORMATION: APPAan-F

<400> SEQUENCE: 70
cagtccgagc ccgagctcaa gctcgagtcc gtcgtcatcg tctcccgcca cggtgtccgc      60
gcccccacca aggccaccca gctcatgcag gacgtcaccc ccgacgcctg gcccacctgg     120
cccgtcaagc tcggttggct cacccccgc ggtggtgagc tcatcgccta cctcggtcac     180
taccagcgcc agcgcctcgt cgccgacggt ctcctcgcca agaagggttg cccccagtcc     240
ggtcaggtcg ccatcatcgc cgacgtcgac gagcgcaccc gcaagaccgg tgaggccttc     300
gccgccggtc tcgcccccga ctgcgccatc accgtccaca cccaggccga cacctcctcc     360
cccgaccccc tcttcaaccc ctgcaagacc ggtgtctgcc agctcgacaa cgccaacgtc     420
accgacgcca tcctctcccg cgccggtggt tccatcgccg acttcaccgg tcaccgccag     480
accgccttcc gcgagctcga gcgcgtcctc aacttccccc agtccaacct ctgcctcaag     540
cgcgagaagc aggacgagtc ctgctccctc acccaggccc tcccctccga gctcaaggtc     600
tccgcctgca acgtctccct caccggtgcc gtctccctcg cctccatgct caccgagatc     660
ttcctcctcc agcaggccca gggtatgccc gagcccggtt ggggtcgcat caccgactcc     720
caccagtgga acaccctcct ctcccctccac aacgcccagt tctacctcct ccagcgcacc     780
cccgaggtcg cccgctcccg cgccacccccc ctcctcgacc tcatcaagac cgccctcacc     840 ccccacccccc cccagaagca ggcctacggt gtcaccctcc ccacctccgt cctcttcatc     900
gccggtcacg acaccaacct cgccaacctc gtggtgccc tcgagctcaa ctggaccctc     960
cccggtcagc cgacaacac cccccggt ggtgagctcg tcttcgagcg ctggcgccgc     1020
ctctccgaca actcccagtg gatccaggtc tccctcgtct tccagaccct ccagcagatg     1080
cgcgacaaga ccccctctc cctcaacacc cccccggtg aggtcaagct caccctcgcc     1140
ggttgcgagg agcgcaacgc ccagggtatg tgctccctcg ccggtttcac ccagatcgtc     1200
aacgaggccc gcatccccgc ctgctccctc taa                                1233

<210> SEQ ID NO 71
<211> LENGTH: 1233
<212> TYPE: DNA
<213> ORGANISM: Artificial Sequence
<220> FEATURE:
<223> OTHER INFORMATION: APPAan-I

<400> SEQUENCE: 71
cagtccgagc ccgagctcaa gctcgagtcc gtcgtcatcg tctcccgcca cggtgtccgc      60
gcccccacca aggccaccca gctcatgcag gacgtcaccc ccgacgcctg gcccacctgg     120
cccgtcaagc tcggttggct cacccccgc ggtggtgagc tcatcgccta cctcggtcac     180
```

```
taccagcgcc agcgcctcgt cgccgacggt ctcctcgcca agaagggttg cccccagtcc    240
ggtcaggtcg ccatcatcgc cgacgtcgac gagcgcaccc gcaagaccgg tgaggccttc    300
gccgccggtc tcgcccccga ctgcgccatc accgtccaca cccaggccga cacctcctcc    360
cccgacccCC tcttcaaccc cctcaagacc ggtgtctgcc agctcgacaa cgccaacgtc    420
accgacgcca tcctctcccg cgccggtggt tccatcgccg acttcaccgg tcaccgccag    480
accgccttcc gctgcctcga gcgcgtcctc aacttccccc agtccaacct ctgcctcaag    540
cgcgagaagc aggacgagtc ctgctccctc acccaggccc tcccctccga gctcaaggtc    600
tccgccgaca acgtctccct caccggtgcc gtctccctcg cctccatgct caccgagatc    660
ttcctcctcc agcaggccca gggtatgccc gagcccggtt ggggtcgcat caccgactcc    720
caccagtgga actgcctcct ctccctccac aacgcccagt tctacctcct ccagcgcacc    780
cccgaggtcg cccgctcccg cgccaccccc ctcctcgacc tcatcaagac cgccctcacc    840
ccccaccccc cccagaagca ggcctacggt gtcaccctcc ccacctccgt cctcttcatc    900
gccggtcacg acaccaacct cgccaacctc ggtggtgccc tcgagctcaa ctggaccctc    960
cccggtcagc ccgacaacac ccccccCggt ggtgagctcg tcttcgagcg ctggcgccgc   1020
ctctccgaca actcccagtg gatccaggtc tccctcgtct tccagaccct ccagcagatg   1080
cgcgacaaga cccccctctc cctcaacacc ccccccggtg aggtcaagct caccctcgcc   1140
ggttgcgagg agcgcaacgc ccagggtatg tgctccctcg ccggtttcac ccagatcgtc   1200
aacgaggccc gcatccccgc ctgctccctc taa                                1233

<210> SEQ ID NO 72
<211> LENGTH: 1233
<212> TYPE: DNA
<213> ORGANISM: Artificial Sequence
<220> FEATURE:
<223> OTHER INFORMATION: APPAan-J

<400> SEQUENCE: 72
cagtccgagc ccgagctcaa gctcgagtcc gtcgtcatcg tctcccgcca cggtgtccgc     60
gcccccacca aggccaccca gctcatgcag gacgtcaccc ccgacgcctg cccaccTgg    120 cccgtcaagc tcggttggct cacccccCgc ggtggtgagc tcatcgccta cctcggtcac    180
taccagcgcc agcgcctcgt cgccgacggt ctcctcgcca agaagggttg cccccagtcc    240
ggtcaggtcg ccatcatcgc cgacgtcgac gagcgcaccc gcaagaccgg tgaggccttc    300
gccgccggtc tcgcccccga ctgcgccatc accgtccaca cccaggccga cacctcctcc    360
cccgacccCC tcttcaaccc cctcaagacc ggtgtctgcc agctcgacaa cgccaacgtc    420
accgacgcca tcctctcccg cgccggtggt tccatcgccg acttcaccgg tcaccgccag    480
accgccttcc gcgagctcga gcgcgtcctc aacttccccc agtccaacct ctgcctcaag    540
cgcgagaagc aggacgagtc ctgctccctc tgccaggccc tcccctccga gctcaaggtc    600
tccgccgaca acgtctccct caccggtgcc gtctccctcg cctccatgct caccgagatc    660
ttcctcctcc agcaggccca gggtatgccc gagcccggtt ggggtcgcat caccgactgc    720
caccagtgga acaccctcct ctccctccac aacgcccagt tctacctcct ccagcgcacc    780
cccgaggtcg cccgctcccg cgccaccccc ctcctcgacc tcatcaagac cgccctcacc    840
ccccaccccc cccagaagca ggcctacggt gtcaccctcc ccacctccgt cctcttcatc    900
gccggtcacg acaccaacct cgccaacctc ggtggtgccc tcgagctcaa ctggaccctc    960
cccggtcagc ccgacaacac ccccccCggt ggtgagctcg tcttcgagcg ctggcgccgc   1020
```

```
ctctccgaca actcccagtg gatccaggtc tccctcgtct tccagaccct ccagcagatg    1080
cgcgacaaga cccccctctc cctcaacacc cccccggtg aggtcaagct caccctcgcc    1140
ggttgcgagg agcgcaacgc ccagggtatg tgctccctcg ccggtttcac ccagatcgtc    1200
aacgaggccc gcatccccgc ctgctccctc taa                                1233
```

<210> SEQ ID NO 73
<211> LENGTH: 1233
<212> TYPE: DNA
<213> ORGANISM: Artificial Sequence
<220> FEATURE:
<223> OTHER INFORMATION: APPAan-K

<400> SEQUENCE: 73

```
cagtccgagc ccgagctcaa gctcgagtcc gtcgtcatcg tctcccgcca cggtgtccgc      60
gcccccacca aggccaccca gctcatgcag gacgtcaccc ccgacgcctg gcccacctgg    120
cccgtcaagc tcggttggct cacccccgc ggtggtgagc tcatcgccta cctcggtcac     180
taccagcgcc agcgcctcgt cgccgacggt ctcctcgcca agaagggttg ccccccagtcc    240 ggtcaggtcg ccatcatcgc cgacgtcgac gagcgcaccc gcaagaccgg tgaggccttc    300
gccgccggtc tcgcccccga ctgcgccatc accgtccaca cccaggccga cacctcctcc    360 cccgacccc tcttcaaccc cctcaagacc ggtgtctgcc agctcgacaa cgccaacgtc    420
accgacgcca tcctctcccg cgccggtggt tccatcgccg acttcaccgg tcaccgccag    480
accgccttcc gcgagctcga gcgcgtcctc aacttccccc agtccaacct ctgcctcaag    540
cgcgagaagc aggacgagtc ctgctccctc acccaggccc tccctgcga gctcaaggtc    600 tccgccgaca acgtctccct caccggtgcc tgctccctcg cctccatgct caccgagatc    660
ttcctcctcc agcaggccca gggtatgccc gagcccggtt ggggtcgcat caccgactcc    720
caccagtgga acaccctcct ctccctccac aacgcccagt tctacctcct ccagcgcacc    780
cccgaggtcg cccgctcccg cgccaccccc ctcctcgacc tcatcaagac cgccctcacc    840 ccccacccc cccagaagca ggcctacggt gtcaccctcc ccacctccgt cctcttcatc    900
gccggtcacg acaccaacct cgccaacctc ggtggtgccc tcgagctcaa ctggacccctc    960 cccggtcagc ccgacaacac cccccccggt ggtgagctcg tcttcgagcg ctggcgccgc    1020
ctctccgaca actcccagtg gatccaggtc tccctcgtct tccagaccct ccagcagatg    1080
cgcgacaaga cccccctctc cctcaacacc cccccggtg aggtcaagct caccctcgcc    1140
ggttgcgagg agcgcaacgc ccagggtatg tgctccctcg ccggtttcac ccagatcgtc    1200
aacgaggccc gcatccccgc ctgctccctc taa                                1233
```

<210> SEQ ID NO 74
<211> LENGTH: 1233
<212> TYPE: DNA
<213> ORGANISM: Artificial Sequence
<220> FEATURE:
<223> OTHER INFORMATION: APPAan-L

<400> SEQUENCE: 74

```
cagtccgagc ccgagctcaa gctcgagtcc gtcgtcatcg tctcccgcca cggtgtccgc      60
gcccccacca aggccaccca gctcatgcag gacgtcaccc ccgacgcctg gcccacctgg    120
cccgtcaagc tcggttggct cacccccgc ggtggtgagc tcatcgccta cctcggtcac     180
taccagcgcc agcgcctcgt cgccgacggt ctcctcgcca agaagggttg ccccccagtcc    240
```

| | |
|---|---|
| ggtcaggtcg ccatcatcgc cgacgtcgac gagcgcaccc gcaagaccgg tgaggccttc | 300 |
| gccgccggtc tcgccccga ctgcgccatc accgtccaca cccaggccga cacctcctcc | 360 |
| cccgaccccc tcttcaaccc cctcaagacc ggtgtctgcc agctcgacaa cgccaacgtc | 420 |
| accgacgcca tcctctcccg cgccggtggt tccatcgccg acttcaccgg tcaccgccag | 480 |
| accgccttcc gcgagctcga gcgcgtcctc aacttccccc agtccaacct ctgcctcaag | 540 |
| cgcgagaagc aggacgagtc ctgctccctc acccaggccc tcccctccga gctcaaggtc | 600 |
| tccgccgaca acgtctccct caccggtgcc gtctccctcg cctccatgct caccgagatc | 660 |
| ttcctcctcc agcaggccca gggtatgccc gagcccggtt ggggtcgcat caccgactcc | 720 |
| caccagtgga cacccctcct ctccctccac aacgcccagt tctacctcct ccagcgcacc | 780 |
| cccgaggtct gccgctcccg cgccaccccc ctcctcgacc tcatcaagac cgccctcacc | 840 |
| ccccacccc cccagaagca ggcctacggt gtcaccctcc ccacctccgt cctcttcatc | 900 |
| gccggtcacg acaccaacct cgccaacctc ggttgcgccc tcgagctcaa ctggaccctc | 960 |
| cccggtcagc ccgacaacac ccccccggt ggtgagctcg tcttcgagcg ctggcgccgc | 1020 |
| ctctccgaca actcccagtg gatccaggtc tccctcgtct tccagaccct ccagcagatg | 1080 |
| cgcgacaaga cccccctctc cctcaacacc cccccggtg aggtcaagct cacccctcgcc | 1140 |
| ggttgcgagg agcgcaacgc ccagggtatg tgctccctcg ccggtttcac ccagatcgtc | 1200 |
| aacgaggccc gcatccccgc ctgctccctc taa | 1233 |

<210> SEQ ID NO 75
<211> LENGTH: 1233
<212> TYPE: DNA
<213> ORGANISM: Artificial Sequence
<220> FEATURE:
<223> OTHER INFORMATION: APPAan-M

<400> SEQUENCE: 75

| | |
|---|---|
| cagtccgagc ccgagctcaa gctcgagtcc gtcgtcatcg tctcccgcca cggtgtccgc | 60 |
| gcccccacca aggccaccca gctcatgcag gacgtcaccc ccgacgcctg gccacctgg | 120 |
| cccgtcaagc tcggttggct caccccccgc ggtggtgagc tcatcgccta cctcggtcac | 180 |
| taccagcgcc agcgcctcgt cgccgacggt ctcctcgcca agaagggttg cccccagtcc | 240 |
| ggtcaggtcg ccatcatcgc cgacgtcgac gagcgcaccc gcaagaccgg tgaggccttc | 300 |
| gccgccggtc tcgccccga ctgcgccatc accgtccaca cccaggccga cacctcctcc | 360 |
| cccgaccccc tcttcaaccc cctcaagacc ggtgtctgcc agctcgacaa cgccaacgtc | 420 |
| accgacgcca tcctctcccg cgccggtggt tccatcgccg acttcaccgg tcaccgccag | 480 |
| accgccttcc gcgagctcga gcgcgtcctc aacttccccc agtccaacct ctgcctcaag | 540 |
| cgcgagaagc aggacgagtc ctgctccctc acccaggccc tcccctccga gctcaaggtc | 600 |
| tccgccgaca acgtctccct caccggtgcc gtctccctcg cctccatgct caccgagatc | 660 |
| ttcctcctcc agcaggccca gggtatgccc gagcccggtt ggggtcgcat caccgactcc | 720 |
| caccagtgga cacccctcct ctccctccac aacgcccagt tctacctcct ccagcgcacc | 780 |
| cccgaggtcg cccgctcccg cgccaccccc ctcctcgacc tcatcaagac cgccctcacc | 840 |
| ccccacccc cccagaagca ggcctacggt gtcaccctcc ccacctccgt cctcttcatc | 900 |
| gccggtcacg acaccaacct cgccaacctc ggtggtgccc tctgcctcaa ctggaccctc | 960 |
| cccggtcagc ccgacaacac ccccccggt ggtgagctcg tcttcgagcg ctggcgccgc | 1020 |
| ctctccgaca actcccagtg gatccaggtc tccctcgtct tccagaccct ccagcagatg | 1080 |

| | |
|---|---:|
| cgcgacaaga cccccctctc cctcaacacc cccccggtg aggtcaagct caccctctgc | 1140 |
| ggttgcgagg agcgcaacgc ccagggtatg tgctccctcg ccggtttcac ccagatcgtc | 1200 |
| aacgaggccc gcatccccgc ctgctccctc taa | 1233 |

<210> SEQ ID NO 76
<211> LENGTH: 1233
<212> TYPE: DNA
<213> ORGANISM: Artificial Sequence
<220> FEATURE:
<223> OTHER INFORMATION: APPAan-N

<400> SEQUENCE: 76

| | |
|---|---:|
| cagtccgagc ccgagctcaa gctcgagtcc gtcgtcatcg tctcccgcca cggtgtccgc | 60 |
| gcccccacca aggccaccca gctcatgcag gacgtcaccc ccgacgcctg gcccacctgg | 120 |
| cccgtcaagc tcggttggct cacccccgc ggtggtgagc tcatcgccta cctcggtcac | 180 |
| taccagcgcc agcgcctcgt cgccgacggt ctcctcgcca agaagggttg cccccagtcc | 240 |
| ggtcaggtcg ccatcatcgc cgacgtcgac gagcgcaccc gcaagaccgg tgaggccttc | 300 |
| gccgccggtc tcgcccccga ctgcgccatc accgtccaca cccaggccga cacctcctcc | 360 |
| cccgaccccc tcttcaaccc cctcaagacc ggtgtctgcc agctcgacaa cgccaacgtc | 420 |
| accgacgcca cctctcccg cgccggtggt tccatcgccg acttcaccgg tcaccgccag | 480 |
| accgccttcc gcgagctcga gcgcgtcctc aacttccccc agtccaacct ctgcctcaag | 540 |
| cgcgagaagc aggacgagtc ctgctccctc acccaggccc tccccctcga gctcaaggtc | 600 |
| tccgccgaca acgtctccct caccggtgcc gtctccctcg cctccatgct caccgagatc | 660 |
| ttcctcctcc agcaggccca gggtatgccc gagcccggtt ggggtcgcat caccgactcc | 720 |
| caccagtgga acaccctcct ctccctccac aacgccagt tctacctcct ccagcgcacc | 780 |
| cccgaggtcg cccgctcccg cgccacccc ctcctcgacc tcatcaagac cgccctcacc | 840 |
| ccccaccccc ccagaagca ggcctacggt gtcaccctcc ccacctccgt cctcttcatc | 900 |
| gccggtcacg acaccaacct cgccaacctc ggtggtgccc tcgagctcaa ctggacccctc | 960 |
| ccctgccagc ccgacaacac cccccccggt ggtgagctcg tcttcgagcg ctggcgccgc | 1020 |
| ctctccgaca actcccagtg gatccaggtc tccctcgtct tccagtgcct ccagcagatg | 1080 |
| cgcgacaaga cccccctctc cctcaacacc ccccccggtg aggtcaagct caccctcgcc | 1140 |
| ggttgcgagg agcgcaacgc ccagggtatg tgctccctcg ccggtttcac ccagatcgtc | 1200 |
| aacgaggccc gcatccccgc ctgctccctc taa | 1233 |

<210> SEQ ID NO 77
<211> LENGTH: 1233
<212> TYPE: DNA
<213> ORGANISM: Artificial Sequence
<220> FEATURE:
<223> OTHER INFORMATION: APPAan-O

<400> SEQUENCE: 77

| | |
|---|---:|
| cagtccgagc ccgagctcaa gctcgagtcc gtcgtcatcg tctcccgcca cggtgtccgc | 60 |
| gcccccacca aggccaccca gctcatgcag gacgtcaccc ccgacgcctg gcccacctgg | 120 |
| cccgtcaagc tcggttggct cacccccgc ggtggtgagc tcatcgccta cctcggtcac | 180 |
| taccagcgcc agcgcctcgt cgccgacggt ctcctcgcca agaagggttg cccccagtcc | 240 |
| ggtcaggtcg ccatcatcgc cgacgtcgac gagcgcaccc gcaagaccgg tgaggccttc | 300 |

| | |
|---|---|
| gccgccggtc tcgcccccga ctgcgccatc accgtccaca cccaggccga cacctcctcc | 360 |
| cccgacccec tcttcaaccc cctcaagacc ggtgtctgcc agctcgacaa cgccaacgtc | 420 |
| accgacgcca tcctctcccg cgccggtggt tccatcgccg acttcaccgg tcaccgccag | 480 |
| accgccttcc gcgagctcga gcgcgtcctc aacttccccc agtccaacct ctgcctcaag | 540 |
| cgcgagaagc aggacgagtc ctgctccctc acccaggccc tccctccga gctcaaggtc | 600 |
| tccgccgaca cgtctccct caccggtgcc gtctccctcg cctccatgct caccgagatc | 660 |
| ttcctcctcc agcaggccca gggtatgccc gagcccggtt ggggtcgcat caccgactcc | 720 |
| caccagtgga caccctcct ctccctccac aacgcccagt tctacctcct ccagcgcacc | 780 |
| cccgaggtcg cccgctcccg cgccaccccc ctcctcgacc tcatcaagac cgccctcacc | 840 |
| ccccaccccc cccagaagca ggcctacggt gtcaccctcc ccacctccgt cctcttcatc | 900 |
| gccggtcacg acaccaacct cgccaacctc ggtggtgccc tcgagctcaa ctggaccctc | 960 |
| cccggtcagc ccgacaacac ccccccccggt ggtgagctcg tcttcgagcg ctggcgccgc | 1020 |
| ctctccgaca actcctgctg gatccaggtc tccctcgtct tccagaccct ccagcagatg | 1080 |
| cgcgacaaga ccccccctctc cctcaacacc ccccccggtg aggtcaagct caccctcgcc | 1140 |
| ggttgcgagg agcgcaacgc ccagggtatg tgctcctgcg ccggtttcac ccagatcgtc | 1200 |
| aacgaggccc gcatccccgc ctgctccctc taa | 1233 |

<210> SEQ ID NO 78
<211> LENGTH: 1233
<212> TYPE: DNA
<213> ORGANISM: Aspergillus niger

<400> SEQUENCE: 78

| | |
|---|---|
| cagagtgagc ctgagttgaa actggaatcc gttgtcatcg tctctagaca tggtgttaga | 60 |
| gcaccaacca aggccaccca acttatgcaa gatgtcaccc cagacgcttg gccaacctgg | 120 |
| ccagtcaagc tgggttggtt gacacctaga ggtggtgagc tcattgctta cttgggtcac | 180 |
| taccaaagac agcgtcttgt tgccgacgga ttgttggcca agaagggttg tccacaatct | 240 |
| ggtcaagtag ctattattgc tgacgtcgac gaaagaaccc gtaagacagg tgaagccttc | 300 |
| gccgccggtc ttgctcctga ctgtgccatt accgttcaca cccaagctga cacttcttct | 360 |
| ccagatccat tgttcaaccc tttgaagact ggtgtttgcc aattggacaa cgctaacgtt | 420 |
| actgacgcta tcttgtccag agctggagga tccattgctg acttcaccgg tcacagacag | 480 |
| actgccttca gagagttgga aagagttctt aacttcccac aatcaaactt gtgcttgaag | 540 |
| cgtgagaagc aagacgaatc ctgttccttg actcaagcat taccatctga gttgaaggtc | 600 |
| tccgccgaca cgtctctttt gaccggtgct gtcagcttgg cttccatgtt gactgaaatc | 660 |
| tttcttctgc aacaagctca aggtatgcct gagccaggtt ggggtagaat caccgactct | 720 |
| caccaatgga caccttgtt gtcсcttgcac aacgctcaat tctacttgct gcagagaact | 780 |
| ccagaggttg ctagatccag agccacccca ttgttggact tgatcaagac tgctttgact | 840 |
| cctcacccac ctcaaaagca agcctacggt gttaccttgc ccacttctgt cttgttcatt | 900 |
| gccggtcacg atactaactt ggcaaatctc ggcggtgctt tggagttgaa ctggactctt | 960 |
| cctggtcaac ctgataacac tccaccaggt ggtgagctcg ttttcgaaag atggcgtaga | 1020 |
| ctatctgata actctcaatg gattcaggtt tcgttggtct tccaaacttt gcagcagatg | 1080 |
| agagacaaga ctccactgtc tttgaacacg cctccaggaa agtcaaatt gaccttggct | 1140 |
| ggatgtgaag agagaaatgc tcagggtatg tgttccttgg ctggtttcac tcaaatcgtt | 1200 | aacgaagcta gaatcccagc ttgttccttg tag　　　　　　　　　　　　　　　　　　　　1233

<210> SEQ ID NO 79
<211> LENGTH: 410
<212> TYPE: PRT
<213> ORGANISM: Artificial Sequence
<220> FEATURE:
<223> OTHER INFORMATION: APPA-M2

<400> SEQUENCE: 79

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Asn Gln Thr Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Ser Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro Asn Gly Thr Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

```
Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
            405                 410

<210> SEQ ID NO 80
<211> LENGTH: 410
<212> TYPE: PRT
<213> ORGANISM: Artificial Sequence
<220> FEATURE:
<223> OTHER INFORMATION: AAPA-M2-B

<400> SEQUENCE: 80

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Cys Tyr Leu Gly His Tyr Trp Arg Gln
50                  55                  60

Arg Leu Val Ala Asp Glu Leu Leu Pro Asn Gln Thr Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Cys Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Ser Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro Asn Gly Thr Gln Lys Gln Ala
        275                 280                 285

Tyr Gly Val Thr Leu Pro Thr Ser Val Leu Phe Ile Ala Gly His Asp
290                 295                 300
```

```
Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 81
<211> LENGTH: 410
<212> TYPE: PRT
<213> ORGANISM: Artificial Sequence
<220> FEATURE:
<223> OTHER INFORMATION: APPA-M2-C

<400> SEQUENCE: 81

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Cys Leu Gly His Tyr Trp Arg Gln
        50                  55                  60

Arg Leu Val Ala Asp Glu Leu Leu Pro Asn Gln Thr Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Ser Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255
```

```
Leu Gln Arg Thr Pro Glu Val Ala Arg Ser Arg Ala Thr Pro Leu Leu
            260                 265                 270

Asp Leu Ile Lys Thr Ala Leu Thr Pro Asn Gly Thr Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
            325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Cys Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
            405                 410

<210> SEQ ID NO 82
<211> LENGTH: 410
<212> TYPE: PRT
<213> ORGANISM: Artificial Sequence
<220> FEATURE:
<223> OTHER INFORMATION: APPA-M2-D

<400> SEQUENCE: 82

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Cys Trp Arg Gln
    50                  55                  60

Arg Leu Val Ala Asp Glu Leu Leu Pro Asn Gln Thr Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Ser Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205
```

Gly Ala Val Ser Leu Ala Ser Met Leu Thr Glu Ile Phe Leu Leu Gln
     210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro Asn Gly Thr Gln Lys Gln Ala
                275                 280                 285

Tyr Gly Val Thr Leu Pro Thr Ser Val Leu Phe Ile Ala Gly His Asp
    290                 295                 300

Thr Asn Leu Ala Asn Leu Gly Ala Leu Glu Leu Asn Trp Thr Leu
305                 310                 315                 320

Pro Gly Gln Pro Asp Asn Thr Pro Pro Gly Gly Leu Val Phe Glu
                325                 330                 335

Arg Trp Arg Arg Leu Ser Asp Asn Ser Gln Trp Ile Val Ser Leu
                340                 345                 350

Val Phe Gln Thr Leu Gln Gln Met Arg Asp Lys Thr Pro Cys Ser Leu
    355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 83
<211> LENGTH: 410
<212> TYPE: PRT
<213> ORGANISM: Artificial Sequence
<220> FEATURE:
<223> OTHER INFORMATION: APPA-M2-M

<400> SEQUENCE: 83

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Tyr Leu Gly His Tyr Trp Arg Gln
50                  55                  60

Arg Leu Val Ala Asp Glu Leu Leu Pro Asn Gln Thr Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Glu Arg Ala Gly Gly Ser Ile Ala Asp Phe Thr Gly His Tyr Gln
145                 150                 155                 160

```
Thr Ala Phe Arg Glu Leu Glu Arg Val Leu Asn Phe Ser Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro Asn Gly Thr Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Cys Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Cys Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 84
<211> LENGTH: 410
<212> TYPE: PRT
<213> ORGANISM: Artificial Sequence
<220> FEATURE:
<223> OTHER INFORMATION: APPA-M2-O

<400> SEQUENCE: 84

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Asn Gln Thr Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110
```

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Arg Val Leu Asn Phe Ser Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro Asn Gly Thr Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Cys Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
370                 375                 380

Arg Asn Ala Gln Gly Met Cys Ser Cys Ala Gly Phe Thr Gln Ile Val
385                 390                 395                 400

Asn Glu Ala Arg Ile Pro Ala Cys Ser Leu
                405                 410

<210> SEQ ID NO 85
<211> LENGTH: 410
<212> TYPE: PRT
<213> ORGANISM: Artificial Sequence
<220> FEATURE:
<223> OTHER INFORMATION: APPA-M2-BO

<400> SEQUENCE: 85

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Cys Tyr Leu Gly His Tyr Trp Arg Gln
    50                  55                  60

```
Arg Leu Val Ala Asp Glu Leu Leu Pro Asn Gln Thr Cys Pro Gln Ser
 65                  70                  75                  80

Gly Gln Val Ala Ile Ile Ala Asp Val Asp Glu Arg Thr Arg Lys Thr
                 85                  90                  95

Gly Glu Ala Phe Ala Ala Cys Leu Ala Pro Asp Cys Ala Ile Thr Val
                100                 105                 110

His Thr Gln Ala Asp Thr Ser Ser Pro Asp Pro Leu Phe Asn Pro Leu
                115                 120                 125

Lys Thr Gly Val Cys Gln Leu Asp Asn Ala Asn Val Thr Asp Ala Ile
            130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Ser Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro Asn Gly Thr Gln Lys Gln Ala
            275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Cys Trp Ile Gln Val Ser Leu
                340                 345                 350

Val Phe Gln Thr Leu Gln Gln Met Arg Asp Lys Thr Pro Leu Ser Leu
                355                 360                 365

Asn Thr Pro Pro Gly Glu Val Lys Leu Thr Leu Ala Gly Cys Glu Glu
            370                 375                 380

Arg Asn Ala Gln Gly Met Cys Ser Cys Ala Gly Phe Thr Gln Ile Val
385                 390                 395                 400

Asn Glu Ala Arg Ile Pro Ala Cys Ser Leu
                405                 410

<210> SEQ ID NO 86
<211> LENGTH: 410
<212> TYPE: PRT
<213> ORGANISM: Artificial Sequence
<220> FEATURE:
<223> OTHER INFORMATION: APPA-M2-DO

<400> SEQUENCE: 86

Gln Ser Glu Pro Glu Leu Lys Leu Glu Ser Val Val Ile Val Ser Arg
 1               5                  10                  15
```

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Cys Trp Arg Gln
 50                  55                  60

Arg Leu Val Ala Asp Glu Leu Leu Pro Asn Gln Thr Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Ser Gln Ser Asn
            165                 170                 175

Leu Cys Leu Lys Arg Glu Lys Gln Asp Glu Ser Cys Ser Leu Thr Gln
        180                 185                 190

Ala Leu Pro Ser Glu Leu Lys Val Ser Ala Asp Asn Val Ser Leu Thr
    195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
            245                 250                 255

Leu Gln Arg Thr Pro Glu Val Ala Arg Ser Arg Ala Thr Pro Leu Leu
        260                 265                 270

Asp Leu Ile Lys Thr Ala Leu Thr Pro Asn Gly Thr Gln Lys Gln Ala
    275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
            325                 330                 335

Arg Trp Arg Arg Leu Ser Asp Asn Ser Cys Trp Ile Gln Val Ser Leu
        340                 345                 350

Val Phe Gln Thr Leu Gln Gln Met Arg Asp Lys Thr Pro Cys Ser Leu
    355                 360                 365

Asn Thr Pro Pro Gly Glu Val Lys Leu Thr Leu Ala Gly Cys Glu Glu
370                 375                 380

Arg Asn Ala Gln Gly Met Cys Ser Cys Ala Gly Phe Thr Gln Ile Val
385                 390                 395                 400

Asn Glu Ala Arg Ile Pro Ala Cys Ser Leu
                405                 410

<210> SEQ ID NO 87
<211> LENGTH: 410
<212> TYPE: PRT

<213> ORGANISM: Artificial Sequence
<220> FEATURE:
<223> OTHER INFORMATION: APPA-M2-MO

<400> SEQUENCE: 87

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Tyr Leu Gly His Tyr Trp Arg Gln
        50                  55                  60

Arg Leu Val Ala Asp Glu Leu Leu Pro Asn Gln Thr Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Ser Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro Asn Gly Thr Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Cys Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Cys Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Cys Gly Cys Glu Glu
    370                 375                 380

Arg Asn Ala Gln Gly Met Cys Ser Cys Ala Gly Phe Thr Gln Ile Val
```

```
                385                 390                 395                 400
Asn Glu Ala Arg Ile Pro Ala Cys Ser Leu
                405                 410

<210> SEQ ID NO 88
<211> LENGTH: 410
<212> TYPE: PRT
<213> ORGANISM: Artificial Sequence
<220> FEATURE:
<223> OTHER INFORMATION: APPA-M2-CO

<400> SEQUENCE: 88

Gln Ser Glu Pro Glu Leu Lys Leu Glu Ser Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Cys Leu Gly His Tyr Trp Arg Gln
    50                  55                  60

Arg Leu Val Ala Asp Glu Leu Leu Pro Asn Gln Thr Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Ser Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro Asn Gly Thr Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Cys Trp Ile Gln Val Ser Leu
```

```
              340             345            350
Val Phe Gln Thr Leu Gln Gln Met Arg Asp Lys Thr Pro Cys Ser Leu
            355                 360                365

Asn Thr Pro Pro Gly Glu Val Lys Leu Thr Leu Ala Gly Cys Glu Glu
            370                 375                380

Arg Asn Ala Gln Gly Met Cys Ser Cys Ala Gly Phe Thr Gln Ile Val
385                 390                 395                400

Asn Glu Ala Arg Ile Pro Ala Cys Ser Leu
                405                 410

<210> SEQ ID NO 89
<211> LENGTH: 1233
<212> TYPE: DNA
<213> ORGANISM: Artificial Sequence
<220> FEATURE:
<223> OTHER INFORMATION: APPA-M2

<400> SEQUENCE: 89
```

| | | | |
|---|---|---|---|
| cagtccgagc cgagctgaa gctggagtcc gtcgtcatcg tctcccgcca cggtgtccgc | 60 |
| gccccacca aggccaccca gctgatgcag acgtcaccc ccgacgcctg gcccacctgg | 120 |
| cccgtcaagc tgggtgagct gacccccgc ggtggtgagc tgatcgccta cctgggtcac | 180 |
| tactggcgcc agcgcctggt cgccgacgag ctgctgccca accagacctg cccccagtcc | 240 |
| ggtcaggtcg ccatcatcgc cgacgtcgac gagcgcaccc gcaagaccgg tgaggccttc | 300 |
| gccgccggtc tggccccga ctgcgccatc accgtccaca cccaggccga cacctcctcc | 360 |
| cccgaccccc tgttcaaccc cctgaagacc ggtgtctgcc agctggacaa cgccaacgtc | 420 |
| accgacgcca tcctggagcg cgccggtggt tccatcgccg acttcaccgg tcactaccag | 480 |
| accgccttcc gcgagctgga gcgcgtcctg aacttctccc agtccaacct gtgcctgaag | 540 |
| cgcgagaagc aggacgagtc ctgctcccctg acccaggccc tgccctccga gctgaaggtc | 600 |
| tccgccgaca cgtctccct gaccggtgcc gtctccctgg cctccatgct gaccgagatc | 660 |
| ttcctgctgc agcaggccca gggtatgccc gagcccggtt ggggtcgcat caccgactcc | 720 |
| caccagtgga cacccctgct gtccctgcac aacgcccagt cgacctgct gcagcgcacc | 780 |
| cccgaggtcg cccgctcccg cgccacccccc ctgctggacc tgatcaagac cgccctgacc | 840 |
| cccaacggta cccagaagca ggcctacggt gtcaccctgc ccacctccgt cctgttcatc | 900 |
| gccggtcacg acaccaacct ggccaacctg gtggtgccc tggagctgaa ctggaccctg | 960 |
| cccggtcagc cgacaacac cccccggt ggtgagctgg tcttcgagcg ctggcgccgc | 1020 |
| ctgtccgaca ctcccagtg gatccaggtc tccctggtct tccagaccct gcagcagatg | 1080 |
| cgcgacaaga cccccctgtc cctgaacacc cccccggtg aggtcaagct gaccctggcc | 1140 |
| ggttgcgagg agcgcaacgc ccagggtatg tgctccctgg ccggtttcac ccagatcgtc | 1200 |
| aacgaggccc gcatccccgc ctgctccctg taa | 1233 |

```
<210> SEQ ID NO 90
<211> LENGTH: 1233
<212> TYPE: DNA
<213> ORGANISM: Artificial Sequence
<220> FEATURE:
<223> OTHER INFORMATION: APPA-M2-B

<400> SEQUENCE: 90
```

| | |
|---|---|
| cagtccgagc cgagctgaa gctggagtcc gtcgtcatcg tctcccgcca cggtgtccgc | 60 |
| gccccacca aggccaccca gctgatgcag acgtcaccc ccgacgcctg gcccacctgg | 120 |

```
cccgtcaagc tgggtgagct gaccccccgc ggtggtgagc tgatctgcta cctgggtcac      180
tactggcgcc agcgcctggt cgccgacgag ctgctgccca accagacctg cccccagtcc      240
ggtcaggtcg ccatcatcgc cgacgtcgac gagcgcaccc gcaagaccgg tgaggccttc      300
gccgcctgcc tggcccccga ctgcgccatc accgtccaca cccaggccga cacctcctcc      360
cccgaccccc tgttcaaccc cctgaagacc ggtgtctgcc agctggacaa cgccaacgtc      420
accgacgcca tcctggagcg cgccggtggt tccatcgccg acttcaccgg tcactaccag      480
accgccttcc gcgagctgga gcgcgtcctg aacttctccc agtccaacct gtgcctgaag      540
cgcgagaagc aggacgagtc ctgctccctg acccaggccc tgccctccga gctgaaggtc      600
tccgccgaca acgtctccct gaccggtgcc gtctccctgg cctccatgct gaccgagatc      660
ttcctgctgc agcaggccca gggtatgccc gagcccggtt ggggtcgcat caccgactcc      720
caccagtgga acaccctgct gtccctgcac aacgcccagt tcgacctgct gcagcgcacc      780
cccgaggtcg cccgctcccg cgccaccccc ctgctggacc tgatcaagac cgccctgacc      840
cccaacggta cccagaagca ggcctacggt gtcaccctgc ccacctccgt cctgttcatc      900
gccggtcacg acaccaacct ggccaacctg gtggtgccc tggagctgaa ctggaccctg      960
cccggtcagc ccgacaacac ccccccggt ggtgagctgg tcttcgagcg ctggcgccgc     1020
ctgtccgaca ctcccagtg gatccaggtc tccctggtct ccagaccct gcagcagatg     1080 cgcgacaaga ccccctgtc cctgaacacc ccccggtg aggtcaagct gaccctggcc     1140
ggttgcgagg agcgcaacgc ccagggtatg tgctccctgg ccggttcac ccagatcgtc     1200 aacgaggccc gcatccccgc ctgctccctg taa                                1233

<210> SEQ ID NO 91
<211> LENGTH: 1233
<212> TYPE: DNA
<213> ORGANISM: Artificial Sequence
<220> FEATURE:
<223> OTHER INFORMATION: AAPA-M2-C

<400> SEQUENCE: 91
cagtccgagc ccgagctgaa gctggagtcc gtcgtcatcg tctcccgcca cggtgtccgc       60 gccccccacca aggccaccca gctgatgcag gacgtcaccc ccgacgcctg gccacctgg      120 cccgtcaagc tgggtgagct gaccccccgc ggtggtgagc tgatcgcctg cctgggtcac      180
tactggcgcc agcgcctggt cgccgacgag ctgctgccca accagacctg cccccagtcc      240
ggtcaggtcg ccatcatcgc cgacgtcgac gagcgcaccc gcaagaccgg tgaggccttc      300
gccgccggtc tggcccccga ctgcgccatc accgtccaca cccaggccga cacctcctcc      360
cccgaccccc tgttcaaccc cctgaagacc ggtgtctgcc agctggacaa cgccaacgtc      420
accgacgcca tcctggagcg cgccggtggt tccatcgccg acttcaccgg tcactaccag      480
accgccttcc gcgagctgga gcgcgtcctg aacttctccc agtccaacct gtgcctgaag      540
cgcgagaagc aggacgagtc ctgctccctg acccaggccc tgccctccga gctgaaggtc      600
tccgccgaca acgtctccct gaccggtgcc gtctccctgg cctccatgct gaccgagatc      660
ttcctgctgc agcaggccca gggtatgccc gagcccggtt ggggtcgcat caccgactcc      720
caccagtgga acaccctgct gtccctgcac aacgcccagt tcgacctgct gcagcgcacc      780
cccgaggtcg cccgctcccg cgccaccccc ctgctggacc tgatcaagac cgccctgacc      840
cccaacggta cccagaagca ggcctacggt gtcaccctgc ccacctccgt cctgttcatc      900
```

| gccggtcacg acaccaacct ggccaacctg ggtggtgccc tggagctgaa ctggaccctg | 960 |
| cccggtcagc ccgacaacac ccccccggt ggtgagctgg tcttcgagcg ctggcgccgc | 1020 |
| ctgtccgaca actcccagtg gatccaggtc tccctggtct tccagaccct gcagcagatg | 1080 |
| cgcgacaaga ccccctgctc cctgaacacc ccccccggtg aggtcaagct gaccctggcc | 1140 |
| ggttgcgagg agcgcaacgc ccagggtatg tgctccctgg ccggtttcac ccagatcgtc | 1200 |
| aacgaggccc gcatccccgc ctgctccctg taa | 1233 |

<210> SEQ ID NO 92
<211> LENGTH: 1233
<212> TYPE: DNA
<213> ORGANISM: Artificial Sequence
<220> FEATURE:
<223> OTHER INFORMATION: AAPA-M2-D

<400> SEQUENCE: 92

| cagtccgagc ccgagctgaa gctggagtcc gtcgtcatcg tctcccgcca cggtgtccgc | 60 |
| gcccccacca aggccaccca gctgatgcag gacgtcaccc ccgacgcctg gcccacctgg | 120 |
| cccgtcaagc tgggtgagct gaccccccgc ggtggtgagc tgatcgccta cctgggtcac | 180 |
| tgctggcgcc agcgcctggt cgccgacgag ctgctgccca accagacctg cccccagtcc | 240 |
| ggtcaggtcg ccatcatcgc cgacgtcgac gagcgcaccc gcaagaccgg tgaggccttc | 300 |
| gccgccggtc tggcccccga ctgcgccatc accgtccaca cccaggccga cacctcctcc | 360 |
| cccgaccccc tgttcaaccc cctgaagacc ggtgtctgcc agctggacaa cgccaacgtc | 420 |
| accgacgcca tcctggagcg cgccggtggt tccatcgccg acttcaccgg tcactaccag | 480 |
| accgccttcc gcgagctgga gcgcgtcctg aacttctccc agtccaacct gtgcctgaag | 540 |
| cgcgagaagc aggacgagtc ctgctccctg acccaggccc tgccctccga gctgaaggtc | 600 |
| tccgccgaca cgtctccct gaccggtgcc gtctccctgg cctccatgct gaccgagatc | 660 |
| ttcctgctgc agcaggccca gggtatgccc gagcccggtt ggggtcgcat caccgactcc | 720 |
| caccagtgga cacccctgct gtccctgcac aacgcccagt tcgacctgct gcagcgcacc | 780 |
| cccgaggtcg cccgctcccg cgccaccccc ctgctggacc tgatcaagac cgccctgacc | 840 |
| cccaacggta cccagaagca ggcctacggt gtcaccctgc ccacctccgt cctgttcatc | 900 |
| gccggtcacg acaccaacct ggccaacctg ggtggtgccc tggagctgaa ctggaccctg | 960 |
| cccggtcagc ccgacaacac ccccccggt ggtgagctgg tcttcgagcg ctggcgccgc | 1020 |
| ctgtccgaca actcccagtg gatccaggtc tccctggtct tccagaccct gcagcagatg | 1080 |
| cgcgacaaga ccccctgctc cctgaacacc ccccccggtg aggtcaagct gaccctggcc | 1140 |
| ggttgcgagg agcgcaacgc ccagggtatg tgctccctgg ccggtttcac ccagatcgtc | 1200 |
| aacgaggccc gcatccccgc ctgctccctg taa | 1233 |

<210> SEQ ID NO 93
<211> LENGTH: 1233
<212> TYPE: DNA
<213> ORGANISM: Artificial Sequence
<220> FEATURE:
<223> OTHER INFORMATION: APPA-M2-M

<400> SEQUENCE: 93

| cagtccgagc ccgagctgaa gctggagtcc gtcgtcatcg tctcccgcca cggtgtccgc | 60 |
| gcccccacca aggccaccca gctgatgcag gacgtcaccc ccgacgcctg gcccacctgg | 120 |
| cccgtcaagc tgggtgagct gaccccccgc ggtggtgagc tgatcgccta cctgggtcac | 180 |

```
tactggcgcc agcgcctggt cgccgacgag ctgctgccca accagacctg cccccagtcc    240
ggtcaggtcg ccatcatcgc cgacgtcgac gagcgcaccc gcaagaccgg tgaggccttc    300
gccgccggtc tggcccccga ctgcgccatc accgtccaca cccaggccga cacctcctcc    360
cccgaccccc tgttcaaccc cctgaagacc ggtgtctgcc agctggacaa cgccaacgtc    420
accgacgcca tcctggagcg cgccggtggt ccatcgccg acttcaccgg tcactaccag    480
accgccttcc gcgagctgga gcgcgtcctg aacttctccc agtccaacct gtgcctgaag    540
cgcgagaagc aggacgagtc ctgctccctg acccaggccc tgccctccga gctgaaggtc    600
tccgccgaca acgtctccct gaccggtgcc gtctccctgg cctccatgct gaccgagatc    660
ttcctgctgc agcaggccca gggtatgccc gagcccggtt ggggtcgcat caccgactcc    720
caccagtgga cacccgctgct gtccctgcac aacgcccagt cgacctgct gcagcgcacc    780 cccgaggtcg cccgctcccg cgccacccc ctgctggacc tgatcaagac cgccctgacc    840
cccaacggta cccagaagca ggcctacggt gtcaccctgc ccacctccgt cctgttcatc    900
gccggtcacg acaccaacct ggccaacctg gtggtgccc tgtgcctgaa ctggaccctg    960
cccggtcagc ccgacaacac ccccccggt ggtgagctgg tcttcgagcg ctggcgccgc   1020
ctgtccgaca actcccagtg gatccaggtc tccctggtct tccagaccct gcagcagatg   1080
cgcgacaaga ccccctgtc cctgaacacc ccccccggtg aggtcaagct gaccctgtgc   1140
ggttgcgagg agcgcaacgc ccagggtatg tgctccctgg ccggttcac ccagatcgtc   1200 aacgaggccc gcatccccgc ctgctccctg taa                              1233

<210> SEQ ID NO 94
<211> LENGTH: 1233
<212> TYPE: DNA
<213> ORGANISM: Artificial Sequence
<220> FEATURE:
<223> OTHER INFORMATION: APPA-M2-O

<400> SEQUENCE: 94
cagtccgagc ccgagctgaa gctggagtcc gtcgtcatcg tctcccgcca cggtgtccgc     60
gcccccacca aggccaccca gctgatgcag gacgtcaccc ccgacgcctg gcccacctgg    120
cccgtcaagc tgggtgagct gacccccccg ggtggtgagc tgatctgcta cctgggtcac    180
tactggcgcc agcgcctggt cgccgacgag ctgctgccca accagacctg cccccagtcc    240
ggtcaggtcg ccatcatcgc cgacgtcgac gagcgcaccc gcaagaccgg tgaggccttc    300
gccgcctgcc tggcccccga ctgcgccatc accgtccaca cccaggccga cacctcctcc    360
cccgaccccc tgttcaaccc cctgaagacc ggtgtctgcc agctggacaa cgccaacgtc    420
accgacgcca tcctggagcg cgccggtggt ccatcgccg acttcaccgg tcactaccag    480
accgccttcc gcgagctgga gcgcgtcctg aacttctccc agtccaacct gtgcctgaag    540
cgcgagaagc aggacgagtc ctgctccctg acccaggccc tgccctccga gctgaaggtc    600
tccgccgaca acgtctccct gaccggtgcc gtctccctgg cctccatgct gaccgagatc    660
ttcctgctgc agcaggccca gggtatgccc gagcccggtt ggggtcgcat caccgactcc    720
caccagtgga cacccgctgct gtccctgcac aacgcccagt cgacctgct gcagcgcacc    780 cccgaggtcg cccgctcccg cgccacccc ctgctggacc tgatcaagac cgccctgacc    840
cccaacggta cccagaagca ggcctacggt gtcaccctgc ccacctccgt cctgttcatc    900
gccggtcacg acaccaacct ggccaacctg gtggtgccc tggagctgaa ctggaccctg    960
```

| | |
|---|---|
| cccggtcagc cgacaacac ccccccggt ggtgagctgg tcttcgagcg ctggcgccgc | 1020 |
| ctgtccgaca actcccagtg gatccaggtc tccctggtct tccagaccct gcagcagatg | 1080 |
| cgcgacaaga ccccctgtc cctgaacacc ccccggtg aggtcaagct gaccctggcc | 1140 |
| ggttgcgagg agcgcaacgc ccagggtatg tgctccctgg ccggtttcac ccagatcgtc | 1200 |
| aacgaggccc gcatccccgc ctgctccctg taa | 1233 |

<210> SEQ ID NO 95
<211> LENGTH: 1233
<212> TYPE: DNA
<213> ORGANISM: Artificial Sequence
<220> FEATURE:
<223> OTHER INFORMATION: AAPA-M2-BO

<400> SEQUENCE: 95

| | |
|---|---|
| cagtccgagc ccgagctgaa gctggagtcc gtcgtcatcg tctcccgcca cggtgtccgc | 60 |
| gcccccacca aggccaccca gctgatgcag gacgtcaccc ccgacgcctg gcccacctgg | 120 |
| cccgtcaagc tgggtgagct gaccccccgc ggtggtgagc tgatctgcta cctgggtcac | 180 |
| tactggcgcc agcgcctggt cgccgacgag ctgctgccca accagacctg ccccagtcc | 240 |
| ggtcaggtcg ccatcatcgc cgacgtcgac gagcgcaccc gcaagaccgg tgaggccttc | 300 |
| gccgcctgcc tggcccccga ctgcgccatc accgtccaca cccaggccga cacctcctcc | 360 |
| cccgaccccc tgttcaaccc cctgaagacc ggtgtctgcc agctggacaa cgccaacgtc | 420 |
| accgacgcca tcctggagcg cgccggtggt tccatcgccg acttcaccgg tcactaccag | 480 |
| accgccttcc gcgagctgga gcgcgtcctg aacttctccc agtccaacct gtgcctgaag | 540 |
| cgcgagaagc aggacgagtc ctgctccctg acccaggccc tgccctccga gctgaaggtc | 600 |
| tccgccgaca acgtctccct gaccggtgcc gtctccctgg cctccatgct gaccgagatc | 660 |
| ttcctgctgc agcaggccca gggtatgccc gagcccggtt ggggtcgcat caccgactcc | 720 |
| caccagtgga cacccctgct gtccctgcac aacgcccagt cgacctgct gcagcgcacc | 780 |
| cccgaggtcg ccgctcccg cgccacccc ctgctggacc tgatcaagac cgccctgacc | 840 |
| cccaacggta cccagaagca ggcctacggt gtcaccctgc ccacctccgt cctgttcatc | 900 |
| gccggtcacg acaccaacct ggccaacctg gtggtgccc tggagctgaa ctggaccctg | 960 |
| cccggtcagc cgacaacac ccccccggt ggtgagctgg tcttcgagcg ctggcgccgc | 1020 |
| ctgtccgaca actcctgctg gatccaggtc tccctggtct tccagaccct gcagcagatg | 1080 |
| cgcgacaaga ccccctgtc cctgaacacc ccccggtg aggtcaagct gaccctggcc | 1140 |
| ggttgcgagg agcgcaacgc ccagggtatg tgctcctgcg ccggtttcac ccagatcgtc | 1200 |
| aacgaggccc gcatccccgc ctgctccctg taa | 1233 |

<210> SEQ ID NO 96
<211> LENGTH: 1233
<212> TYPE: DNA
<213> ORGANISM: Artificial Sequence
<220> FEATURE:
<223> OTHER INFORMATION: APPA-M2-DO

<400> SEQUENCE: 96

| | |
|---|---|
| cagtccgagc ccgagctgaa gctggagtcc gtcgtcatcg tctcccgcca cggtgtccgc | 60 |
| gcccccacca aggccaccca gctgatgcag gacgtcaccc ccgacgcctg gcccacctgg | 120 |
| cccgtcaagc tgggtgagct gaccccccgc ggtggtgagc tgatcgccta cctgggtcac | 180 |
| tgctggcgcc agcgcctggt cgccgacgag ctgctgccca accagacctg ccccagtcc | 240 |

```
ggtcaggtcg ccatcatcgc cgacgtcgac gagcgcaccc gcaagaccgg tgaggccttc      300
gccgccggtc tggcccccga ctgcgccatc accgtccaca cccaggccga cacctcctcc      360
cccgaccccc tgttcaaccc cctgaagacc ggtgtctgcc agctggacaa cgccaacgtc      420
accgacgcca tcctggagcg cgccggtggt tccatcgccg acttcaccgg tcactaccag      480
accgccttcc gcgagctgga gcgcgtcctg aacttctccc agtccaacct gtgcctgaag      540
cgcgagaagc aggacgagtc ctgctccctg acccaggccc tgccctccga gctgaaggtc      600
tccgccgaca acgtctccct gaccggtgcc gtctccctgg cctccatgct gaccgagatc      660
ttcctgctgc agcaggccca gggtatgccc gagcccggtt ggggtcgcat caccgactcc      720
caccagtgga acaccctgct gtccctgcac aacgcccagt tcgacctgct gcagcgcacc      780
cccgaggtcg cccgctcccg cgccaccccc ctgctggacc tgatcaagac cgccctgacc      840
cccaacggta cccagaagca ggcctacggt gtcaccctgc ccacctccgt cctgttcatc      900
gccggtcacg acaccaacct ggccaacctg gtggtgccc tggagctgaa ctggaccctg      960
cccggtcagc ccgacaacac cccccccggt ggtgagctgg tcttcgagcg ctggcgccgc     1020
ctgtccgaca ctcctgctg atccaggtc tccctggtct tccagaccct gcagcagatg     1080
cgcgacaaga ccccctgctc cctgaacacc ccccccggtg aggtcaagct gaccctggcc     1140
ggttgcgagg agcgcaacgc ccagggtatg tgctcctgcg ccggtttcac ccagatcgtc     1200
aacgaggccc gcatccccgc ctgctccctg taa                                   1233

<210> SEQ ID NO 97
<211> LENGTH: 1233
<212> TYPE: DNA
<213> ORGANISM: Artificial Sequence
<220> FEATURE:
<223> OTHER INFORMATION: APPA-M2-MO

<400> SEQUENCE: 97
cagtccgagc ccgagctgaa gctggagtcc gtcgtcatcg tctcccgcca cggtgtccgc       60
gcccccacca aggccaccca gctgatgcag gacgtcaccc ccgacgcctg gcccacctgg      120
cccgtcaagc tgggtgagct gacccccgc ggtggtgagc tgatcgccta cctgggtcac      180
tactggcgcc agcgcctggt cgccgacgag ctgctgccca accagacctg cccccagtcc      240
ggtcaggtcg ccatcatcgc cgacgtcgac gagcgcaccc gcaagaccgg tgaggccttc      300
gccgccggtc tggcccccga ctgcgccatc accgtccaca cccaggccga cacctcctcc      360
cccgaccccc tgttcaaccc cctgaagacc ggtgtctgcc agctggacaa cgccaacgtc      420
accgacgcca tcctggagcg cgccggtggt tccatcgccg acttcaccgg tcactaccag      480
accgccttcc gcgagctgga gcgcgtcctg aacttctccc agtccaacct gtgcctgaag      540
cgcgagaagc aggacgagtc ctgctccctg acccaggccc tgccctccga gctgaaggtc      600
tccgccgaca acgtctccct gaccggtgcc gtctccctgg cctccatgct gaccgagatc      660
ttcctgctgc agcaggccca gggtatgccc gagcccggtt ggggtcgcat caccgactcc      720
caccagtgga acaccctgct gtccctgcac aacgcccagt tcgacctgct gcagcgcacc      780
cccgaggtcg cccgctcccg cgccaccccc ctgctggacc tgatcaagac cgccctgacc      840
cccaacggta cccagaagca ggcctacggt gtcaccctgc ccacctccgt cctgttcatc      900
gccggtcacg acaccaacct ggccaacctg gtggtgccc tgtgcctgaa ctggaccctg      960
cccggtcagc ccgacaacac cccccccggt ggtgagctgg tcttcgagcg ctggcgccgc     1020
```

```
ctgtccgaca actcctgctg gatccaggtc tccctggtct tccagaccct gcagcagatg    1080
cgcgacaaga ccccctgtc cctgaacacc ccccggtg aggtcaagct gaccctgtgc       1140
ggttgcgagg agcgcaacgc ccagggtatg tgctcctgcg ccggtttcac ccagatcgtc    1200
aacgaggccc gcatccccgc ctgctccctg taa                                  1233
```

<210> SEQ ID NO 98
<211> LENGTH: 1233
<212> TYPE: DNA
<213> ORGANISM: Artificial Sequence
<220> FEATURE:
<223> OTHER INFORMATION: AAPA-M2-CO

<400> SEQUENCE: 98

```
cagtccgagc ccgagctgaa gctggagtcc gtcgtcatcg tctcccgcca cggtgtccgc     60
gcccccacca aggccaccca gctgatgcag gacgtcaccc ccgacgcctg cccacctgg     120 cccgtcaagc tgggtgagct gaccccccgc ggtggtgagc tgatcgcctg cctgggtcac   180
tactggcgcc agcgcctggt cgccgacgag ctgctgccca accagacctg cccccagtcc   240
ggtcaggtcg ccatcatcgc cgacgtcgac gagcgcaccc gcaagaccgg tgaggccttc   300
gccgccggtc tggcccccga ctgcgccatc accgtccaca cccaggccga cacctcctcc   360
cccgaccccc tgttcaaccc cctgaagacc ggtgtctgcc agctggacaa cgccaacgtc   420
accgacgcca tcctggagcg cgccggtggt tccatcgccg acttcaccgg tcactaccag   480
accgccttcc gcgagctgga gcgcgtcctg aacttctccc agtccaacct gtgcctgaag   540
cgcgagaagc aggacgagtc ctgctccctg acccaggccc tgccctccga gctgaaggtc   600
tccgccgaca cgtctccct gaccggtgcc gtctccctgg cctccatgct gaccgagatc   660
ttcctgctgc agcaggccca gggtatgccc gagcccggtt ggggtcgcat caccgactcc   720
caccagtgga cacccctgct gtccctgcac aacgcccagt tcgacctgct gcagcgcacc   780
cccgaggtcg cccgctcccg cgccacccc ctgctggacc tgatcaagac cgccctgacc   840
cccaacggta cccagaagca ggcctacggt gtcaccctgc ccacctccgt cctgttcatc   900
gccggtcacg acaccaacct ggccaacctg gtggtgccc tggagctgaa ctggaccctg   960
cccggtcagc ccgacaacac ccccccggt ggtgagctgg tcttcgagcg ctggcgccgc  1020
ctgtccgaca ctcctgctg gatccaggtc tccctggtct tccagaccct gcagcagatg  1080
cgcgacaaga ccccctgctc cctgaacacc ccccggtg aggtcaagct gaccctggcc   1140
ggttgcgagg agcgcaacgc ccagggtatg tgctcctgcg ccggtttcac ccagatcgtc  1200
aacgaggccc gcatccccgc ctgctccctg taa                                1233
```

<210> SEQ ID NO 99
<211> LENGTH: 410
<212> TYPE: PRT
<213> ORGANISM: Artificial Sequence
<220> FEATURE:
<223> OTHER INFORMATION: APPA-M3

<400> SEQUENCE: 99

```
Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45
```

```
Pro Arg Gly Gly Glu Leu Ile Ala Tyr Leu Gly His Tyr Trp Arg Gln
    50                  55                  60

Arg Leu Val Ala Asp Glu Leu Leu Pro Asn Gln Thr Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His His Gln Ala Asp Thr Ser Ser Pro Asp Pro Leu Phe Asn Pro Leu
            115                 120                 125

Lys Thr Gly Val Cys Gln Leu Asp Val Ala Asn Val Thr Arg Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Ser Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro Asn Gly Thr Gln Lys Gln Ala
            275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 100
<211> LENGTH: 410
<212> TYPE: PRT
<213> ORGANISM: Artificial Sequence
<220> FEATURE:
<223> OTHER INFORMATION: APPA-M3-B

<400> SEQUENCE: 100
```

```
Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
            35                  40                  45

Pro Arg Gly Gly Glu Leu Ile Cys Tyr Leu Gly His Tyr Trp Arg Gln
50                  55                  60

Arg Leu Val Ala Asp Glu Leu Leu Pro Asn Gln Thr Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Cys Leu Ala Pro Asp Cys Ala Ile Thr Val
                100                 105                 110

His His Gln Ala Asp Thr Ser Ser Pro Asp Pro Leu Phe Asn Pro Leu
            115                 120                 125

Lys Thr Gly Val Cys Gln Leu Asp Val Ala Asn Val Thr Arg Ala Ile
            130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Ser Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
                195                 200                 205

Gly Ala Val Ser Leu Ala Ser Met Leu Thr Glu Ile Phe Leu Leu Gln
            210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro Asn Gly Thr Gln Lys Gln Ala
                275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410
```

```
<210> SEQ ID NO 101
<211> LENGTH: 410
<212> TYPE: PRT
<213> ORGANISM: Artificial Sequence
<220> FEATURE:
<223> OTHER INFORMATION: APPA-M3-D

<400> SEQUENCE: 101
```

| | | | | | | | | | | | | | | |
|---|---|---|---|---|---|---|---|---|---|---|---|---|---|---|
|Gln|Ser|Glu|Pro|Glu|Leu|Lys|Leu|Glu|Ser|Val|Val|Ile|Val|Ser|Arg|
|1| | | |5| | | | |10| | | | |15|
|His|Gly|Val|Arg|Ala|Pro|Thr|Lys|Phe|Thr|Gln|Leu|Met|Gln|Asp|Val|
| | | | |20| | | | |25| | | | |30| |
|Thr|Pro|Asp|Ala|Trp|Pro|Thr|Trp|Pro|Val|Lys|Leu|Gly|Glu|Leu|Thr|
| | | | |35| | | | |40| | | | |45| |
|Pro|Arg|Gly|Gly|Glu|Leu|Ile|Ala|Tyr|Leu|Gly|His|Cys|Trp|Arg|Gln|
| |50| | | | |55| | | | |60| | | | |
|Arg|Leu|Val|Ala|Asp|Glu|Leu|Leu|Pro|Asn|Gln|Thr|Cys|Pro|Gln|Ser|
|65| | | | |70| | | | |75| | | | |80|
|Gly|Gln|Val|Ala|Ile|Ile|Ala|Asp|Val|Asp|Glu|Arg|Thr|Arg|Lys|Thr|
| | | | |85| | | | |90| | | | |95| |
|Gly|Glu|Ala|Phe|Ala|Ala|Gly|Leu|Ala|Pro|Asp|Cys|Ala|Ile|Thr|Val|
| | | | |100| | | | |105| | | | |110| |
|His|His|Gln|Ala|Asp|Thr|Ser|Ser|Pro|Asp|Pro|Leu|Phe|Asn|Pro|Leu|
| | | | |115| | | | |120| | | | |125| |
|Lys|Thr|Gly|Val|Cys|Gln|Leu|Asp|Val|Ala|Asn|Val|Thr|Arg|Ala|Ile|
| |130| | | | |135| | | | |140| | | | |
|Leu|Glu|Arg|Ala|Gly|Gly|Ser|Ile|Ala|Asp|Phe|Thr|Gly|His|Tyr|Gln|
|145| | | | |150| | | | |155| | | | |160|
|Thr|Ala|Phe|Arg|Glu|Leu|Glu|Arg|Val|Leu|Asn|Phe|Ser|Gln|Ser|Asn|
| | | | |165| | | | |170| | | | |175| |
|Leu|Cys|Leu|Lys|Arg|Glu|Lys|Gln|Asp|Glu|Ser|Cys|Ser|Leu|Thr|Gln|
| | | | |180| | | | |185| | | | |190| |
|Ala|Leu|Pro|Ser|Glu|Leu|Lys|Val|Ser|Ala|Asp|Asn|Val|Ser|Leu|Thr|
| | | | |195| | | | |200| | | | |205| |
|Gly|Ala|Val|Ser|Leu|Ala|Ser|Met|Leu|Thr|Glu|Ile|Phe|Leu|Leu|Gln|
| |210| | | | |215| | | | |220| | | | |
|Gln|Ala|Gln|Gly|Met|Pro|Glu|Pro|Gly|Trp|Gly|Arg|Ile|Thr|Asp|Ser|
|225| | | | |230| | | | |235| | | | |240|
|His|Gln|Trp|Asn|Thr|Leu|Leu|Ser|Leu|His|Asn|Ala|Gln|Phe|Asp|Leu|
| | | | |245| | | | |250| | | | |255| |
|Leu|Gln|Arg|Thr|Pro|Glu|Val|Ala|Arg|Ser|Arg|Ala|Thr|Pro|Leu|Leu|
| | | | |260| | | | |265| | | | |270| |
|Asp|Leu|Ile|Lys|Thr|Ala|Leu|Thr|Pro|Asn|Gly|Thr|Gln|Lys|Gln|Ala|
| | | | |275| | | | |280| | | | |285| |
|Tyr|Gly|Val|Thr|Leu|Pro|Thr|Ser|Val|Leu|Phe|Ile|Ala|Gly|His|Asp|
| |290| | | | |295| | | | |300| | | | |
|Thr|Asn|Leu|Ala|Asn|Leu|Gly|Gly|Ala|Leu|Glu|Leu|Asn|Trp|Thr|Leu|
|305| | | | |310| | | | |315| | | | |320|
|Pro|Gly|Gln|Pro|Asp|Asn|Thr|Pro|Pro|Gly|Gly|Glu|Leu|Val|Phe|Glu|
| | | | |325| | | | |330| | | | |335| |
|Arg|Trp|Arg|Arg|Leu|Ser|Asp|Asn|Ser|Gln|Trp|Ile|Gln|Val|Ser|Leu|
| | | | |340| | | | |345| | | | |350| |
|Val|Phe|Gln|Thr|Leu|Gln|Gln|Met|Arg|Asp|Lys|Thr|Pro|Cys|Ser|Leu|
| | | | |355| | | | |360| | | | |365| |
|Asn|Thr|Pro|Pro|Gly|Glu|Val|Lys|Leu|Thr|Leu|Ala|Gly|Cys|Glu|Glu|

```
                370                 375                 380
Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 102
<211> LENGTH: 410
<212> TYPE: PRT
<213> ORGANISM: Artificial Sequence
<220> FEATURE:
<223> OTHER INFORMATION: APPA-M3-M

<400> SEQUENCE: 102

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Tyr Leu Gly His Tyr Trp Arg Gln
50                  55                  60

Arg Leu Val Ala Asp Glu Leu Leu Pro Asn Gln Thr Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Ser Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro Asn Gly Thr Gln Lys Gln Ala
        275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Cys Leu Asn Trp Thr Leu
305                 310                 315                 320

Pro Gly Gln Pro Asp Asn Thr Pro Pro Gly Gly Glu Leu Val Phe Glu
```

```
            325                 330                 335
Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Cys Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 103
<211> LENGTH: 410
<212> TYPE: PRT
<213> ORGANISM: Artificial Sequence
<220> FEATURE:
<223> OTHER INFORMATION: APPA-M3-O

<400> SEQUENCE: 103

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Asn Gln Thr Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Ser Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro Asn Gly Thr Gln Lys Gln Ala
```

```
                275                 280                 285
Tyr Gly Val Thr Leu Pro Thr Ser Val Leu Phe Ile Ala Gly His Asp
            290                 295                 300
Thr Asn Leu Ala Asn Leu Gly Gly Ala Leu Glu Leu Asn Trp Thr Leu
305                 310                 315                 320
Pro Gly Gln Pro Asp Asn Thr Pro Pro Gly Gly Leu Val Phe Glu
                325                 330                 335
Arg Trp Arg Arg Leu Ser Asp Asn Ser Cys Trp Ile Gln Val Ser Leu
            340                 345                 350
Val Phe Gln Thr Leu Gln Gln Met Arg Asp Lys Thr Pro Leu Ser Leu
            355                 360                 365
Asn Thr Pro Pro Gly Glu Val Lys Leu Thr Leu Ala Gly Cys Glu Glu
        370                 375                 380
Arg Asn Ala Gln Gly Met Cys Ser Cys Ala Gly Phe Thr Gln Ile Val
385                 390                 395                 400
Asn Glu Ala Arg Ile Pro Ala Cys Ser Leu
                405                 410

<210> SEQ ID NO 104
<211> LENGTH: 410
<212> TYPE: PRT
<213> ORGANISM: Artificial Sequence
<220> FEATURE:
<223> OTHER INFORMATION: APPA-M3-C

<400> SEQUENCE: 104

Gln Ser Glu Pro Glu Leu Lys Leu Glu Ser Val Val Ile Val Ser Arg
1               5                   10                  15
His Gly Val Arg Ala Pro Thr Lys Phe Thr Gln Leu Met Gln Asp Val
            20                  25                  30
Thr Pro Asp Ala Trp Pro Thr Trp Pro Val Lys Leu Gly Glu Leu Thr
        35                  40                  45
Pro Arg Gly Gly Glu Leu Ile Ala Cys Leu Gly His Tyr Trp Arg Gln
    50                  55                  60
Arg Leu Val Ala Asp Glu Leu Leu Pro Asn Gln Thr Cys Pro Gln Ser
65                  70                  75                  80
Gly Gln Val Ala Ile Ile Ala Asp Val Asp Glu Arg Thr Arg Lys Thr
                85                  90                  95
Gly Glu Ala Phe Ala Ala Gly Leu Ala Pro Asp Cys Ala Ile Thr Val
            100                 105                 110
His His Gln Ala Asp Thr Ser Ser Pro Asp Pro Leu Phe Asn Pro Leu
        115                 120                 125
Lys Thr Gly Val Cys Gln Leu Asp Val Ala Asn Val Thr Arg Ala Ile
    130                 135                 140
Leu Glu Arg Ala Gly Gly Ser Ile Ala Asp Phe Thr Gly His Tyr Gln
145                 150                 155                 160
Thr Ala Phe Arg Glu Leu Glu Arg Val Leu Asn Phe Ser Gln Ser Asn
                165                 170                 175
Leu Cys Leu Lys Arg Glu Lys Gln Asp Glu Ser Cys Ser Leu Thr Gln
            180                 185                 190
Ala Leu Pro Ser Glu Leu Lys Val Ser Ala Asp Asn Val Ser Leu Thr
        195                 200                 205
Gly Ala Val Ser Leu Ala Ser Met Leu Thr Glu Ile Phe Leu Leu Gln
    210                 215                 220
Gln Ala Gln Gly Met Pro Glu Pro Gly Trp Gly Arg Ile Thr Asp Ser
```

```
                225                 230                 235                 240
His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro Asn Gly Thr Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Cys Ser Leu
            355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 105
<211> LENGTH: 410
<212> TYPE: PRT
<213> ORGANISM: Artificial Sequence
<220> FEATURE:
<223> OTHER INFORMATION: APPA-M3-BO

<400> SEQUENCE: 105

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Cys Tyr Leu Gly His Tyr Trp Arg Gln
    50                  55                  60

Arg Leu Val Ala Asp Glu Leu Leu Pro Asn Gln Thr Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Cys Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Ser Gln Ser Asn
                165                 170                 175

Leu Cys Leu Lys Arg Glu Lys Gln Asp Glu Ser Cys Ser Leu Thr Gln
```

```
                180              185              190
Ala Leu Pro Ser Glu Leu Lys Val Ser Ala Asp Asn Val Ser Leu Thr
            195                 200                 205
Gly Ala Val Ser Leu Ala Ser Met Leu Thr Glu Ile Phe Leu Leu Gln
            210                 215                 220
Gln Ala Gln Gly Met Pro Glu Pro Gly Trp Gly Arg Ile Thr Asp Ser
225                 230                 235                 240
His Gln Trp Asn Thr Leu Leu Ser Leu His Asn Ala Gln Phe Asp Leu
                245                 250                 255
Leu Gln Arg Thr Pro Glu Val Ala Arg Ser Arg Ala Thr Pro Leu Leu
                260                 265                 270
Asp Leu Ile Lys Thr Ala Leu Thr Pro Asn Gly Thr Gln Lys Gln Ala
            275                 280                 285
Tyr Gly Val Thr Leu Pro Thr Ser Val Leu Phe Ile Ala Gly His Asp
            290                 295                 300
Thr Asn Leu Ala Asn Leu Gly Gly Ala Leu Glu Leu Asn Trp Thr Leu
305                 310                 315                 320
Pro Gly Gln Pro Asp Asn Thr Pro Pro Gly Gly Glu Leu Val Phe Glu
                325                 330                 335
Arg Trp Arg Arg Leu Ser Asp Asn Ser Cys Trp Ile Gln Val Ser Leu
                340                 345                 350
Val Phe Gln Thr Leu Gln Gln Met Arg Asp Lys Thr Pro Leu Ser Leu
            355                 360                 365
Asn Thr Pro Pro Gly Glu Val Lys Leu Thr Leu Ala Gly Cys Glu Glu
370                 375                 380
Arg Asn Ala Gln Gly Met Cys Ser Cys Ala Gly Phe Thr Gln Ile Val
385                 390                 395                 400
Asn Glu Ala Arg Ile Pro Ala Cys Ser Leu
                405                 410

<210> SEQ ID NO 106
<211> LENGTH: 410
<212> TYPE: PRT
<213> ORGANISM: Artificial Sequence
<220> FEATURE:
<223> OTHER INFORMATION: APPA-M3-D0

<400> SEQUENCE: 106

Gln Ser Glu Pro Glu Leu Lys Leu Glu Ser Val Val Ile Val Ser Arg
1               5                   10                  15
His Gly Val Arg Ala Pro Thr Lys Phe Thr Gln Leu Met Gln Asp Val
                20                  25                  30
Thr Pro Asp Ala Trp Pro Thr Trp Pro Val Lys Leu Gly Glu Leu Thr
            35                  40                  45
Pro Arg Gly Gly Glu Leu Ile Ala Tyr Leu Gly His Cys Trp Arg Gln
        50                  55                  60
Arg Leu Val Ala Asp Glu Leu Leu Pro Asn Gln Thr Cys Pro Gln Ser
65                  70                  75                  80
Gly Gln Val Ala Ile Ile Ala Asp Val Asp Glu Arg Thr Arg Lys Thr
                85                  90                  95
Gly Glu Ala Phe Ala Ala Gly Leu Ala Pro Asp Cys Ala Ile Thr Val
                100                 105                 110
His His Gln Ala Asp Thr Ser Ser Pro Asp Pro Leu Phe Asn Pro Leu
            115                 120                 125
Lys Thr Gly Val Cys Gln Leu Asp Val Ala Asn Val Thr Arg Ala Ile
```

```
                130               135                 140
Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Ser Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
                195                 200                 205

Gly Ala Val Ser Leu Ala Ser Met Leu Thr Glu Ile Phe Leu Leu Gln
                210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro Asn Gly Thr Gln Lys Gln Ala
                275                 280                 285

Tyr Gly Val Thr Leu Pro Thr Ser Val Leu Phe Ile Ala Gly His Asp
                290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Cys Trp Ile Gln Val Ser Leu
                340                 345                 350

Val Phe Gln Thr Leu Gln Gln Met Arg Asp Lys Thr Pro Cys Ser Leu
                355                 360                 365

Asn Thr Pro Pro Gly Glu Val Lys Leu Thr Leu Ala Gly Cys Glu Glu
                370                 375                 380

Arg Asn Ala Gln Gly Met Cys Ser Cys Ala Gly Phe Thr Gln Ile Val
385                 390                 395                 400

Asn Glu Ala Arg Ile Pro Ala Cys Ser Leu
                405                 410

<210> SEQ ID NO 107
<211> LENGTH: 410
<212> TYPE: PRT
<213> ORGANISM: Artificial Sequence
<220> FEATURE:
<223> OTHER INFORMATION: APPA-M3-MO

<400> SEQUENCE: 107

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
                20                  25                  30

Thr Pro Asp Ala Trp Pro Thr Trp Pro Val Lys Leu Gly Glu Leu Thr
                35                  40                  45

Pro Arg Gly Gly Glu Leu Ile Ala Tyr Leu Gly His Tyr Trp Arg Gln
                50                  55                  60

Arg Leu Val Ala Asp Glu Leu Leu Pro Asn Gln Thr Cys Pro Gln Ser
65                  70                  75                  80

Gly Gln Val Ala Ile Ile Ala Asp Val Asp Glu Arg Thr Arg Lys Thr
```

```
            85                  90                  95
Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Ser Gln Ser Asn
                165                 170                 175

Leu Cys Leu Lys Arg Glu Lys Gln Asp Glu Ser Cys Ser Leu Thr Gln
                    180                 185                 190

Ala Leu Pro Ser Glu Leu Lys Val Ser Ala Asp Asn Val Ser Leu Thr
                        195                 200                 205

Gly Ala Val Ser Leu Ala Ser Met Leu Thr Glu Ile Phe Leu Leu Gln
            210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                    260                 265                 270

Asp Leu Ile Lys Thr Ala Leu Thr Pro Asn Gly Thr Gln Lys Gln Ala
                        275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Cys Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Cys Trp Ile Gln Val Ser Leu
                    340                 345                 350

Val Phe Gln Thr Leu Gln Gln Met Arg Asp Lys Thr Pro Leu Ser Leu
                        355                 360                 365

Asn Thr Pro Pro Gly Glu Val Lys Leu Thr Leu Cys Gly Cys Glu Glu
            370                 375                 380

Arg Asn Ala Gln Gly Met Cys Ser Cys Ala Gly Phe Thr Gln Ile Val
385                 390                 395                 400

Asn Glu Ala Arg Ile Pro Ala Cys Ser Leu
                405                 410

<210> SEQ ID NO 108
<211> LENGTH: 410
<212> TYPE: PRT
<213> ORGANISM: Artificial Sequence
<220> FEATURE:
<223> OTHER INFORMATION: APPA-M3-CO

<400> SEQUENCE: 108

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
```

```
                35                  40                  45
Pro Arg Gly Gly Glu Leu Ile Ala Cys Leu Gly His Tyr Trp Arg Gln
 50                  55                  60
Arg Leu Val Ala Asp Glu Leu Leu Pro Asn Gln Thr Cys Pro Gln Ser
 65                  70                  75                  80
Gly Gln Val Ala Ile Ala Asp Val Asp Glu Arg Thr Arg Lys Thr
                 85                  90                  95
Gly Glu Ala Phe Ala Ala Gly Leu Ala Pro Asp Cys Ala Ile Thr Val
                100                 105                 110
His His Gln Ala Asp Thr Ser Ser Pro Asp Pro Leu Phe Asn Pro Leu
                115                 120                 125
Lys Thr Gly Val Cys Gln Leu Asp Val Ala Asn Val Thr Arg Ala Ile
                130                 135                 140
Leu Glu Arg Ala Gly Gly Ser Ile Ala Asp Phe Thr Gly His Tyr Gln
145                 150                 155                 160
Thr Ala Phe Arg Glu Leu Glu Arg Val Leu Asn Phe Ser Gln Ser Asn
                165                 170                 175
Leu Cys Leu Lys Arg Glu Lys Gln Asp Glu Ser Cys Ser Leu Thr Gln
                180                 185                 190
Ala Leu Pro Ser Glu Leu Lys Val Ser Ala Asp Asn Val Ser Leu Thr
                195                 200                 205
Gly Ala Val Ser Leu Ala Ser Met Leu Thr Glu Ile Phe Leu Leu Gln
                210                 215                 220
Gln Ala Gln Gly Met Pro Glu Pro Gly Trp Gly Arg Ile Thr Asp Ser
225                 230                 235                 240
His Gln Trp Asn Thr Leu Leu Ser Leu His Asn Ala Gln Phe Asp Leu
                245                 250                 255
Leu Gln Arg Thr Pro Glu Val Ala Arg Ser Arg Ala Thr Pro Leu Leu
                260                 265                 270
Asp Leu Ile Lys Thr Ala Leu Thr Pro Asn Gly Thr Gln Lys Gln Ala
                275                 280                 285
Tyr Gly Val Thr Leu Pro Thr Ser Val Leu Phe Ile Ala Gly His Asp
                290                 295                 300
Thr Asn Leu Ala Asn Leu Gly Gly Ala Leu Glu Leu Asn Trp Thr Leu
305                 310                 315                 320
Pro Gly Gln Pro Asp Asn Thr Pro Gly Gly Glu Leu Val Phe Glu
                325                 330                 335
Arg Trp Arg Arg Leu Ser Asp Asn Ser Cys Trp Ile Gln Val Ser Leu
                340                 345                 350
Val Phe Gln Thr Leu Gln Gln Met Arg Asp Lys Thr Pro Cys Ser Leu
                355                 360                 365
Asn Thr Pro Pro Gly Glu Val Lys Leu Thr Leu Ala Gly Cys Glu Glu
                370                 375                 380
Arg Asn Ala Gln Gly Met Cys Ser Cys Ala Gly Phe Thr Gln Ile Val
385                 390                 395                 400
Asn Glu Ala Arg Ile Pro Ala Cys Ser Leu
                405                 410
```

<210> SEQ ID NO 109
<211> LENGTH: 1233
<212> TYPE: DNA
<213> ORGANISM: Artificial Sequence
<220> FEATURE:
<223> OTHER INFORMATION: APPA-M3

<400> SEQUENCE: 109

```
cagtccgagc ccgagctcaa gctcgagtcc gtcgtcatcg tctcccgcca cggtgtccgc      60
gcccccacca agttcaccca gctcatgcag gacgtcaccc ccgacgcctg gcccacctgg     120
cccgtcaagc tcggtgagct caccccccgc ggtggtgagc tcatcgccta cctcggtcac     180
tactggcgcc agcgcctcgt cgccgacgag ctcctcccca accagacctg cccccagtcc     240
ggtcaggtcg ccatcatcgc cgacgtcgac gagcgcaccc gcaagaccgg tgaggccttc     300
gccgccggtc tcgcccccga ctgcgccatc accgtccacc accaggccga cacctcctcc     360
cccgaccccc tcttcaaccc cctcaagacc ggtgtctgcc agctcgacgt cgccaacgtc     420
acccgcgcca tcctcgagcg cgccggtggt tccatcgccg acttcaccgg tcactaccag     480
accgccttcc gcgagctcga gcgcgtcctc aacttctccc agtccaacct ctgcctcaag     540
cgcgagaagc aggacgagtc ctgctccctc acccaggccc tcccctccga gctcaaggtc     600
tccgccgaca cgtctccct caccggtgcc gtctccctcg cctccatgct caccgagatc     660
ttcctcctcc agcaggccca gggtatgccc gagcccggtt ggggtcgcat caccgactcc     720
caccagtgga acaccctcct ctccctccac aacgcccagt tcgacctcct ccagcgcacc     780
cccgaggtcg cccgctcccg cgccacccccc ctcctcgacc tcatcaagac cgccctcacc     840
cccaacggta cccagaagca ggcctacggt gtcaccctcc ccacctccgt cctcttcatc     900
gccggtcacg acaccaacct cgccaacctc ggtggtgccc tcgagctcaa ctggaccctc     960
cccggtcagc ccgacaacac ccccccccggt ggtgagctcg tcttcgagcg ctggcgccgc    1020
ctctccgaca ctcccagtg gatccaggtc tccctcgtct ccagaccct ccagcagatg    1080
cgcgacaaga ccccctctc cctcaacacc ccccccggtg aggtcaagct cacccctcgcc    1140
ggttgcgagg agcgcaacgc ccagggtatg tgctcccctcg ccggtttcac ccagatcgtc    1200
aacgaggccc gcatccccgc ctgctccctc taa                                 1233
```

<210> SEQ ID NO 110
<211> LENGTH: 1233
<212> TYPE: DNA
<213> ORGANISM: Artificial Sequence
<220> FEATURE:
<223> OTHER INFORMATION: APPA-M3-B

<400> SEQUENCE: 110

```
cagtccgagc ccgagctcaa gctcgagtcc gtcgtcatcg tctcccgcca cggtgtccgc      60
gcccccacca agttcaccca gctcatgcag gacgtcaccc ccgacgcctg gcccacctgg     120
cccgtcaagc tcggtgagct caccccccgc ggtggtgagc tcatctgcta cctcggtcac     180
tactggcgcc agcgcctcgt cgccgacgag ctcctcccca accagacctg cccccagtcc     240
ggtcaggtcg ccatcatcgc cgacgtcgac gagcgcaccc gcaagaccgg tgaggccttc     300
gccgcctgcc tcgcccccga ctgcgccatc accgtccacc accaggccga cacctcctcc     360
cccgaccccc tcttcaaccc cctcaagacc ggtgtctgcc agctcgacgt cgccaacgtc     420
acccgcgcca tcctcgagcg cgccggtggt tccatcgccg acttcaccgg tcactaccag     480
accgccttcc gcgagctcga gcgcgtcctc aacttctccc agtccaacct ctgcctcaag     540
cgcgagaagc aggacgagtc ctgctccctc acccaggccc tcccctccga gctcaaggtc     600
tccgccgaca cgtctccct caccggtgcc gtctccctcg cctccatgct caccgagatc     660
ttcctcctcc agcaggccca gggtatgccc gagcccggtt ggggtcgcat caccgactcc     720
caccagtgga acaccctcct ctccctccac aacgcccagt tcgacctcct ccagcgcacc     780
```

```
cccgaggtcg cccgctcccg cgccacccce ctcctcgacc tcatcaagac cgccctcacc      840
cccaacggta cccagaagca ggcctacggt gtcaccctcc ccacctccgt cctcttcatc      900
gccggtcacg acaccaacct cgccaacctc ggtggtgccc tcgagctcaa ctggaccctc      960
cccggtcagc ccgacaacac cccccccggt ggtgagctcg tcttcgagcg ctggcgccgc     1020
ctctccgaca actcccagtg gatccaggtc tccctcgtct tccagaccct ccagcagatg     1080
cgcgacaaga ccccctctc cctcaacacc ccccccggtg aggtcaagct caccctcgcc      1140
ggttgcgagg agcgcaacgc ccagggtatg tgctccctcg ccggtttcac ccagatcgtc     1200
aacgaggccc gcatccccgc ctgctccctc taa                                  1233
```

<210> SEQ ID NO 111
<211> LENGTH: 1233
<212> TYPE: DNA
<213> ORGANISM: Artificial Sequence
<220> FEATURE:
<223> OTHER INFORMATION: APPA-M3-D

<400> SEQUENCE: 111

```
cagtccgagc ccgagctcaa gctcgagtcc gtcgtcatcg tctcccgcca cggtgtccgc       60
gcccccacca agttcaccca gctcatgcag gacgtcaccc ccgacgcctg cccacctgg       120 cccgtcaagc tcggtgagct caccccccgc ggtggtgagc tcatcgccta cctcggtcac      180
tgctggcgcc agcgcctcgt cgccgacgag ctcctcccca accagacctg cccccagtcc      240
ggtcaggtcg ccatcatcgc cgacgtcgac gagcgcaccc gcaagaccgg tgaggccttc      300
gccgccggtc tcgcccccga ctgcgccatc accgtccacc accaggccga cacctcctcc      360
cccgaccccc tcttcaaccc cctcaagacc ggtgtctgcc agctcgacgt cgccaacgtc      420
acccgcgcca tcctcgagcg cgccggtggt tccatcgccg acttcaccgg tcactaccag      480
accgccttcc gcgagctcga gcgcgtcctc aacttctccc agtccaacct ctgcctcaag      540
cgcgagaagc aggacgagtc ctgctccctc acccaggccc tcccctccga gctcaaggtc      600
tccgccgaca acgtctccct caccggtgcc gtctccctcg cctccatgct caccgagatc      660
ttcctcctcc agcaggccca gggtatgccc gagcccggtt ggggtcgcat caccgactcc      720
caccagtgga acaccctcct ctcccctccac aacgcccagt tcgacctcct ccagcgcacc      780
cccgaggtcg cccgctcccg cgccacccce ctcctcgacc tcatcaagac cgccctcacc      840
cccaacggta cccagaagca ggcctacggt gtcaccctcc ccacctccgt cctcttcatc      900
gccggtcacg acaccaacct cgccaacctc ggtggtgccc tcgagctcaa ctggaccctc      960
cccggtcagc ccgacaacac cccccccggt ggtgagctcg tcttcgagcg ctggcgccgc     1020
ctctccgaca actcccagtg gatccaggtc tccctcgtct tccagaccct ccagcagatg     1080
cgcgacaaga ccccctgctc cctcaacacc ccccccggtg aggtcaagct caccctcgcc     1140
ggttgcgagg agcgcaacgc ccagggtatg tgctccctcg ccggtttcac ccagatcgtc     1200
aacgaggccc gcatccccgc ctgctccctc taa                                  1233
```

<210> SEQ ID NO 112
<211> LENGTH: 1233
<212> TYPE: DNA
<213> ORGANISM: Artificial Sequence
<220> FEATURE:
<223> OTHER INFORMATION: APPA-M3-M

<400> SEQUENCE: 112

```
cagtccgagc ccgagctcaa gctcgagtcc gtcgtcatcg tctcccgcca cggtgtccgc    60
gcccccacca agttcaccca gctcatgcag gacgtcaccc ccgacgcctg gcccacctgg   120
cccgtcaagc tcggtgagct caccccccgc ggtggtgagc tcatcgccta cctcggtcac   180
tactggcgcc agcgcctcgt cgccgacgag ctcctcccca accagacctg cccccagtcc   240
ggtcaggtcg ccatcatcgc cgacgtcgac gagcgcaccc gcaagaccgg tgaggccttc   300
gccgccggtc tcgcccccga ctgcgccatc accgtccacc accaggccga cacctcctcc   360
cccgaccccc tcttcaaccc cctcaagacc ggtgtctgcc agctcgacgt cgccaacgtc   420
acccgcgcca cctcgagcg cgccggtggt tccatcgccg acttcaccgg tcactaccag   480
accgccttcc gcgagctcga gcgcgtcctc aacttctccc agtccaacct ctgcctcaag   540
cgcgagaagc aggacgagtc ctgctccctc acccaggccc tcccctccga gctcaaggtc   600
tccgccgaca cgtctccct caccggtgcc gtctccctcg cctccatgct caccgagatc   660
ttcctcctcc agcaggccca gggtatgccc gagcccggtt ggggtcgcat caccgactcc   720
caccagtgga acaccctcct ctccctccac aacgcccagt cgacctcct ccagcgcacc   780 cccgaggtcg cccgctcccg cgccaccccc ctcctcgacc tcatcaagac cgccctcacc   840
cccaacggta cccagaagca ggcctacggt gtcaccctcc ccacctccgt cctcttcatc   900
gccggtcacg acaccaacct cgccaacctc ggtggtgccc tctgcctcaa ctggaccctc   960 cccgtcagc ccgacaacac ccccccggt ggtgagctcg tcttcgagcg ctggcgccgc  1020
ctctccgaca actcccagtg gatccaggtc tccctcgtct tccagaccct ccagcagatg  1080
cgcgacaaga cccccctctc cctcaacacc ccccccggtg aggtcaagct cacccctctgc  1140 ggttgcgagg agcgcaacgc ccagggtatg tgctccctcg ccggtttcac ccagatcgtc  1200
aacgaggccc gcatccccgc ctgctccctc taa                              1233
```

<210> SEQ ID NO 113
<211> LENGTH: 1233
<212> TYPE: DNA
<213> ORGANISM: Artificial Sequence
<220> FEATURE:
<223> OTHER INFORMATION: APPA-M3-O

<400> SEQUENCE: 113

```
cagtccgagc ccgagctcaa gctcgagtcc gtcgtcatcg tctcccgcca cggtgtccgc    60
gcccccacca agttcaccca gctcatgcag gacgtcaccc ccgacgcctg gcccacctgg   120
cccgtcaagc tcggtgagct caccccccgc ggtggtgagc tcatcgccta cctcggtcac   180
tactggcgcc agcgcctcgt cgccgacgag ctcctcccca accagacctg cccccagtcc   240
ggtcaggtcg ccatcatcgc cgacgtcgac gagcgcaccc gcaagaccgg tgaggccttc   300
gccgccggtc tcgcccccga ctgcgccatc accgtccacc accaggccga cacctcctcc   360
cccgaccccc tcttcaaccc cctcaagacc ggtgtctgcc agctcgacgt cgccaacgtc   420
acccgcgcca cctcgagcg cgccggtggt tccatcgccg acttcaccgg tcactaccag   480
accgccttcc gcgagctcga gcgcgtcctc aacttctccc agtccaacct ctgcctcaag   540
cgcgagaagc aggacgagtc ctgctccctc acccaggccc tcccctccga gctcaaggtc   600
tccgccgaca cgtctccct caccggtgcc gtctccctcg cctccatgct caccgagatc   660
ttcctcctcc agcaggccca gggtatgccc gagcccggtt ggggtcgcat caccgactcc   720
caccagtgga acaccctcct ctccctccac aacgcccagt cgacctcct ccagcgcacc   780 cccgaggtcg cccgctcccg cgccaccccc ctcctcgacc tcatcaagac cgccctcacc   840
```

```
cccaacggta cccagaagca ggcctacggt gtcaccctcc ccacctccgt cctcttcatc    900
gccggtcacg acaccaacct cgccaacctc ggtggtgccc tcgagctcaa ctggaccctc    960
cccggtcagc ccgacaacac ccccccggt ggtgagctcg tcttcgagcg ctggcgccgc    1020
ctctccgaca actcctgctg gatccaggtc tccctcgtct tccagaccct ccagcagatg    1080
cgcgacaaga ccccctctc cctcaacacc ccccggtg aggtcaagct caccctcgcc    1140
ggttgcgagg agcgcaacgc ccagggtatg tgctcctgcg ccggtttcac ccagatcgtc    1200
aacgaggccc gcatccccgc ctgctccctc taa                                 1233
```

<210> SEQ ID NO 114
<211> LENGTH: 1233
<212> TYPE: DNA
<213> ORGANISM: Artificial Sequence
<220> FEATURE:
<223> OTHER INFORMATION: APPA-M3-C

<400> SEQUENCE: 114

```
cagtccgagc ccgagctcaa gctcgagtcc gtcgtcatcg tctcccgcca cggtgtccgc     60
gcccccacca agttcaccca gctcatgcag gacgtcaccc ccgacgcctg gcccacctgg    120
cccgtcaagc tcggtgagct caccccccgc ggtggtgagc tcatcgcctg cctcggtcac    180
tactggcgcc agcgcctcgt cgccgacgag ctcctcccca accagacctg cccccagtcc    240
ggtcaggtcg ccatcatcgc cgacgtcgac gagcgcaccc gcaagaccgg tgaggccttc    300
gccgccggtc tcgcccccga ctgcgccatc accgtccacc accaggccga cacctcctcc    360
cccgaccccc tcttcaaccc cctcaagacc ggtgtctgcc agctcgacgt cgccaacgtc    420
acccgcgcca cctcgagcg cgccggtggt tccatcgccg acttcaccgg tcactaccag    480
accgccttcc gcgagctcga gcgcgtcctc aacttctccc agtccaacct ctgcctcaag    540
cgcgagaagc aggacgagtc ctgctccctc acccaggccc tcccctcga gtcaaggtc    600 tccgccgaca acgtctccct caccggtgcc gtctccctcg cctccatgct caccgagatc    660
ttcctcctcc agcaggccca gggtatgccc gagcccggtt ggggtcgcat caccgactcc    720
caccagtgga cacccctcct ctccctccac aacgcccagt cgacctcct ccagcgcacc    780 cccgaggtcg cccgctcccg cgccacccc ctcctcgacc tcatcaagac cgccctcacc    840
cccaacggta cccagaagca ggcctacggt gtcaccctcc ccacctccgt cctcttcatc    900
gccggtcacg acaccaacct cgccaacctc ggtggtgccc tcgagctcaa ctggaccctc    960
cccggtcagc ccgacaacac ccccccggt ggtgagctcg tcttcgagcg ctggcgccgc    1020
ctctccgaca actcccagtg gatccaggtc tccctcgtct tccagaccct ccagcagatg    1080
cgcgacaaga cccctgctc cctcaacacc ccccggtg aggtcaagct caccctcgcc    1140
ggttgcgagg agcgcaacgc ccagggtatg tgctcctcg ccggtttcac ccagatcgtc    1200
aacgaggccc gcatccccgc ctgctccctc taa                                 1233
```

<210> SEQ ID NO 115
<211> LENGTH: 1233
<212> TYPE: DNA
<213> ORGANISM: Artificial Sequence
<220> FEATURE:
<223> OTHER INFORMATION: APPA-M3-BO

<400> SEQUENCE: 115

```
cagtccgagc ccgagctcaa gctcgagtcc gtcgtcatcg tctcccgcca cggtgtccgc     60
```

```
gcccccacca agttcaccca gctcatgcag gacgtcaccc ccgacgcctg gcccacctgg    120
cccgtcaagc tcggtgagct cacccccgc ggtggtgagc tcatctgcta cctcggtcac    180
tactggcgcc agcgcctcgt cgccgacgag ctcctcccca accagacctg ccccagtcc    240 ggtcaggtcg ccatcatcgc cgacgtcgac gagcgcaccc gcaagaccgg tgaggccttc    300
gccgcctgcc tcgcccccga ctgcgccatc accgtccacc accaggccga cacctcctcc    360
cccgaccccc tcttcaaccc cctcaagacc ggtgtctgcc agctcgacgt cgccaacgtc    420
acccgcgcca tcctcgagcg cgccggtggt tccatcgccg acttcaccgg tcactaccag    480
accgccttcc gcgagctcga gcgcgtcctc aacttctccc agtccaacct ctgcctcaag    540
cgcgagaagc aggacgagtc ctgctccctc acccaggccc tcccctccga gctcaaggtc    600
tccgccgaca acgtctccct caccggtgcc gtctccctcg cctccatgct caccgagatc    660
ttcctcctcc agcaggccca gggtatgccc gagcccggtt ggggtcgcat caccgactcc    720
caccagtgga acaccctcct ctccctccac aacgcccagt tcgacctcct ccagcgcacc    780
cccgaggtcg cccgctcccg cgccaccccc ctcctcgacc tcatcaagac cgccctcacc    840
cccaacggta cccagaagca ggcctacggt gtcaccctcc ccacctccgt cctcttcatc    900
gccggtcacg acaccaacct cgccaacctc ggtggtgccc tcgagctcaa ctggaccctc    960
cccggtcagc ccgacaacac ccccccggt ggtgagctcg tcttcgagcg ctggcgccgc   1020
ctctccgaca actcctgctg gatccaggtc tccctcgtct ccagaccct ccagcagatg   1080 cgcgacaaga cccccctctc cctcaacacc ccccggtg aggtcaagct caccctcgcc   1140
ggttgcgagg agcgcaacgc ccagggtatg tgctcctgcg ccggtttcac ccagatcgtc   1200
aacgaggccc gcatccccgc ctgctccctc taa                                1233
```

<210> SEQ ID NO 116
<211> LENGTH: 1233
<212> TYPE: DNA
<213> ORGANISM: Artificial Sequence
<220> FEATURE:
<223> OTHER INFORMATION: APPA-M3-DO

<400> SEQUENCE: 116

```
cagtccgagc ccgagctcaa gctcgagtcc gtcgtcatcg tctcccgcca cggtgtccgc     60
gcccccacca agttcaccca gctcatgcag gacgtcaccc ccgacgcctg gcccacctgg    120
cccgtcaagc tcggtgagct cacccccgc ggtggtgagc tcatcgccta cctcggtcac    180
tgctggcgcc agcgcctcgt cgccgacgag ctcctcccca accagacctg ccccagtcc    240 ggtcaggtcg ccatcatcgc cgacgtcgac gagcgcaccc gcaagaccgg tgaggccttc    300
gccgccggtc tcgcccccga ctgcgccatc accgtccacc accaggccga cacctcctcc    360
cccgaccccc tcttcaaccc cctcaagacc ggtgtctgcc agctcgacgt cgccaacgtc    420
acccgcgcca tcctcgagcg cgccggtggt tccatcgccg acttcaccgg tcactaccag    480
accgccttcc gcgagctcga gcgcgtcctc aacttctccc agtccaacct ctgcctcaag    540
cgcgagaagc aggacgagtc ctgctccctc acccaggccc tcccctccga gctcaaggtc    600
tccgccgaca acgtctccct caccggtgcc gtctccctcg cctccatgct caccgagatc    660
ttcctcctcc agcaggccca gggtatgccc gagcccggtt ggggtcgcat caccgactcc    720
caccagtgga acaccctcct ctccctccac aacgcccagt tcgacctcct ccagcgcacc    780
cccgaggtcg cccgctcccg cgccaccccc ctcctcgacc tcatcaagac cgccctcacc    840
cccaacggta cccagaagca ggcctacggt gtcaccctcc ccacctccgt cctcttcatc    900
```

```
gccggtcacg acaccaacct cgccaacctc ggtggtgccc tcgagctcaa ctggaccctc      960
cccggtcagc ccgacaacac ccccccggt ggtgagctcg tcttcgagcg ctggcgccgc      1020
ctctccgaca actcctgctg gatccaggtc tccctcgtct tccagaccct ccagcagatg     1080
cgcgacaaga cccctgctc cctcaacacc cccccggtg aggtcaagct caccctcgcc      1140
ggttgcgagg agcgcaacgc ccagggtatg tgctcctgcg ccggtttcac ccagatcgtc    1200
aacgaggccc gcatccccgc ctgctccctc taa                                 1233
```

<210> SEQ ID NO 117
<211> LENGTH: 1233
<212> TYPE: DNA
<213> ORGANISM: Artificial Sequence
<220> FEATURE:
<223> OTHER INFORMATION: APPA-M3-MO

<400> SEQUENCE: 117

```
cagtccgagc ccgagctcaa gctcgagtcc gtcgtcatcg tctcccgcca cggtgtccgc      60
gcccccacca agttcaccca gctcatgcag gacgtcaccc ccgacgcctg gcccacctgg     120
cccgtcaagc tcggtgagct caccccccgc ggtggtgagc tcatcgccta cctcggtcac     180
tactggcgcc agcgcctcgt cgccgacgag ctcctcccca accagacctg cccccagtcc    240
ggtcaggtcg ccatcatcgc cgacgtcgac gagcgcaccc gcaagaccgg tgaggccttc    300
gccgccggtc tcgcccccga ctgcgccatc accgtccacc accaggccga cacctcctcc    360
cccgaccccc tcttcaaccc cctcaagacc ggtgtctgcc agctcgacgt cgccaacgtc    420
acccgcgcca tcctcgagcg cgccggtggt tccatcgccg acttcaccgg tcactaccag   480
accgccttcc gcgagctcga gcgcgtcctc aacttctccc agtccaacct ctgcctcaag    540
cgcgagaagc aggacgagtc ctgctccctc acccaggccc tccctccga gctcaaggtc    600 tccgccgaca acgtctccct caccggtgcc gtctccctcg cctccatgct caccgagatc   660
ttcctcctcc agcaggccca gggtatgccc gagcccggtt ggggtcgcat caccgactcc   720
caccagtgga cacccctcct ctcccctccac aacgcccagt cgacctcct ccagcgcacc    780 cccgaggtcg cccgctcccg cgccaccccc ctcctcgacc tcatcaagac cgccctcacc    840
cccaacggta cccagaagca ggcctacggt gtcaccctcc ccacctccgt cctcttcatc    900
gccggtcacg acaccaacct cgccaacctc ggtggtgccc tctgcctcaa ctggaccctc   960
cccggtcagc ccgacaacac ccccccggt ggtgagctcg tcttcgagcg ctggcgccgc    1020
ctctccgaca actcctgctg gatccaggtc tccctcgtct tccagaccct ccagcagatg   1080
cgcgacaaga cccccctctc cctcaacacc cccccggtg aggtcaagct caccctctgc    1140
ggttgcgagg agcgcaacgc ccagggtatg tgctcctgcg ccggtttcac ccagatcgtc   1200
aacgaggccc gcatccccgc ctgctccctc taa                                1233
```

<210> SEQ ID NO 118
<211> LENGTH: 1233
<212> TYPE: DNA
<213> ORGANISM: Artificial Sequence
<220> FEATURE:
<223> OTHER INFORMATION: APPA-M3-CO

<400> SEQUENCE: 118

```
cagtccgagc ccgagctcaa gctcgagtcc gtcgtcatcg tctcccgcca cggtgtccgc     60
gcccccacca agttcaccca gctcatgcag gacgtcaccc ccgacgcctg gcccacctgg   120
```

-continued

```
cccgtcaagc tcggtgagct cacccccgc ggtggtgagc tcatcgcctg cctcggtcac    180
tactggcgcc agcgcctcgt cgccgacgag ctcctcccca accagacctg cccccagtcc    240
ggtcaggtcg ccatcatcgc cgacgtcgac gagcgcaccc gcaagaccgg tgaggccttc    300
gccgccggtc tcgccccga ctgcgccatc accgtccacc accaggccga cacctcctcc    360 cccgacccc tcttcaaccc cctcaagacc ggtgtctgcc agctcgacgt cgccaacgtc    420
acccgcgcca tcctcgagcg cgccggtggt tccatcgccg acttcaccgg tcactaccag    480
accgccttcc gcgagctcga gcgcgtcctc aacttctccc agtccaacct ctgcctcaag    540
cgcgagaagc aggacgagtc ctgctccctc acccaggccc tcccctccga gctcaaggtc    600
tccgccgaca acgtctccct caccggtgcc gtctccctcg cctccatgct caccgagatc    660
ttcctcctcc agcaggccca gggtatgccc gagcccggtt ggggtcgcat caccgactcc    720
caccagtgga acaccctcct ctccctccac aacgccagt tcgacctcct ccagcgcacc    780
cccgaggtcg cccgctcccg cgccaccccc ctcctcgacc tcatcaagac cgccctcacc    840
cccaacggta cccagaagca ggcctacggt gtcaccctcc ccacctccgt cctcttcatc    900
gccggtcacg acaccaacct cgccaacctc ggtggtgccc tcgagctcaa ctggaccctc    960 cccgtcagc ccgacaacac ccccccggt ggtgagctcg tcttcgagcg ctggcgccgc    1020
ctctccgaca actcctgctg gatccaggtc tccctcgtct tccagaccct ccagcagatg    1080
cgcgacaaga ccccctgctc cctcaacacc cccccggtg aggtcaagct caccctcgcc    1140
ggttgcgagg agcgcaacgc ccagggtatg tgctcctgcg ccggtttcac ccagatcgtc    1200
aacgaggccc gcatccccgc ctgctccctc taa                                 1233
```